US009932399B2

(12) United States Patent
Heider et al.

(10) Patent No.: US 9,932,399 B2
(45) Date of Patent: *Apr. 3, 2018

(54) ANTI CD37 ANTIBODIES

(71) Applicant: Boehringer Ingelheim International GmbH, Ingelheim am Rhein (DE)

(72) Inventors: Karl-Heinz Heider, Stockerau (AT); Eric Borges, Moedling (AT); Elinborg Ostermann, Mauerbach (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/693,047

(22) Filed: Apr. 22, 2015

(65) Prior Publication Data

US 2016/0137729 A1    May 19, 2016

Related U.S. Application Data

(63) Continuation of application No. 13/974,230, filed on Aug. 23, 2013, now abandoned, which is a continuation of application No. 12/672,378, filed as application No. PCT/EP2008/060464 on Aug. 8, 2008, now abandoned.

(30) Foreign Application Priority Data

Aug. 9, 2007 (EP) ..................................... 07114128

(51) Int. Cl.
| | | |
|---|---|---|
| C07K 16/28 | (2006.01) | |
| A01K 67/027 | (2006.01) | |
| A61K 39/395 | (2006.01) | |
| A61K 45/06 | (2006.01) | |
| C07K 16/30 | (2006.01) | |
| A61K 39/00 | (2006.01) | |

(52) U.S. Cl.
CPC .......... *C07K 16/28* (2013.01); *A01K 67/0275* (2013.01); *A61K 39/39558* (2013.01); *A61K 45/06* (2013.01); *C07K 16/2896* (2013.01); *C07K 16/3061* (2013.01); *A01K 2207/15* (2013.01); *A01K 2217/072* (2013.01); *A01K 2227/105* (2013.01); *A61K 2039/505* (2013.01); *C07K 2317/24* (2013.01); *C07K 2317/72* (2013.01); *C07K 2317/73* (2013.01); *C07K 2317/732* (2013.01); *C07K 2317/76* (2013.01); *C07K 2317/92* (2013.01)

(58) Field of Classification Search
CPC ............ C07K 16/2896; C07K 16/3061; A61K 2039/505; A61K 39/39558
See application file for complete search history.

(56) References Cited

U.S. PATENT DOCUMENTS

| | | |
|---|---|---|
| 5,500,362 A | 3/1996 | Robinson et al. |
| 6,020,153 A | 2/2000 | Hardman et al. |
| 6,461,824 B1 | 10/2002 | Better et al. |
| 6,548,640 B1 | 4/2003 | Winter |
| 8,333,966 B2 | 12/2012 | Tan et al. |
| 8,992,915 B2* | 3/2015 | Heider ............... A61K 39/3955 424/133.1 |
| 9,078,879 B2* | 7/2015 | Heider ............... A01K 67/0275 |
| 2003/0133939 A1 | 7/2003 | Ledbetter et al. |
| 2007/0020259 A1 | 1/2007 | Hansen et al. |
| 2007/0059306 A1 | 3/2007 | Grosmaire et al. |
| 2007/0237779 A1 | 10/2007 | Ledbetter et al. |
| 2008/0279850 A1 | 11/2008 | Brady et al. |
| 2009/0274692 A1 | 11/2009 | Tan et al. |
| 2010/0135900 A1 | 6/2010 | Cerveny et al. |
| 2010/0189722 A1 | 7/2010 | Heider et al. |
| 2011/0165153 A1 | 7/2011 | Heider et al. |
| 2012/0189618 A1 | 7/2012 | Stilgenbauer et al. |
| 2013/0236454 A1 | 9/2013 | Stilgenbauer et al. |
| 2013/0287797 A1 | 10/2013 | Heider et al. |
| 2013/0309224 A1 | 11/2013 | Heider et al. |
| 2013/0309225 A1 | 11/2013 | Heider et al. |
| 2014/0004110 A1 | 1/2014 | Heider et al. |
| 2014/0010808 A1 | 1/2014 | Heider et al. |
| 2015/0231242 A1* | 8/2015 | Heider ............. A61K 39/39558 424/174.1 |
| 2015/0266967 A1* | 9/2015 | Stilgenbauer ...... C07K 16/2896 424/133.1 |
| 2016/0106837 A1 | 4/2016 | Heider et al. |

FOREIGN PATENT DOCUMENTS

| | | |
|---|---|---|
| EP | 2295080 A2 | 3/2011 |
| WO | 2003074679 A2 | 9/2003 |
| WO | 2004016753 A2 | 2/2004 |

(Continued)

OTHER PUBLICATIONS

Andristos, L. et al., "A Phase 1 Trial of TRU-016, an Anti-CD37; Small Modular Immunopharmaceutical (SMIP TM) Protein in Relapsed and Refractory CLL: Early Promising Clinical Activity". Blood (ASH Annual Meeting Abstracts), 2009, 114, Abstract 3424 [retrieved from the internet: www.truemergent.com/wp-content/uploads/a_phase_1_trial_of_tru-016-ppt-final.pdf).

Andristos, L. et al., "A phase I trial of TRU-016, an anti-CD37 smaller modular immunopharmaceutical (SMIP) in relapsed and refractory CLL". 2009 ASCO Annual Meeting, Abstract No. 3017, Journal of Clinical Oncology, American Society of Clinical Oncology, U.S. vol. 27, No. 15s, Jan. 1, 2009.

Andritsos, L. et al., A Phase 1 Trial of TRU-016, An Anti-CD37 Small Modular Immunopharmaceutical (SMIP TM) Protein in Relapsed and Refractory CLL: Early Promising Clinical Activity. Bllod (ASH Annual Meeting Abstracts) 2009, 114: Abstract 3424 American Society of Hematology, vol. 114, No. 2, Dec. 8, 2009, p. 1330.

(Continued)

*Primary Examiner* — Jessica H Roark
(74) *Attorney, Agent, or Firm* — Edouard G. Lebel; David J. Kershner; Gabriel J. McCool

(57) ABSTRACT

Chimeric and humanized anti-CD37 antibodies and pharmaceutical compositions containing them are useful for the treatment of B cell malignancies and autoimmune and inflammatory diseases that involve B cells in their pathology.

10 Claims, 19 Drawing Sheets

(56) References Cited

FOREIGN PATENT DOCUMENTS

| WO | 200517148 A1 | 2/2005 |
|---|---|---|
| WO | 2007014278 A2 | 2/2007 |
| WO | 2007041635 A2 | 4/2007 |
| WO | 2009019312 A2 | 2/2009 |
| WO | 2009023386 A2 | 2/2009 |
| WO | 2009126944 A1 | 10/2009 |
| WO | 2010011697 A1 | 1/2010 |
| WO | 2010057047 A1 | 5/2010 |
| WO | 2012007576 A1 | 1/2012 |
| WO | 2014198330 A1 | 12/2014 |

OTHER PUBLICATIONS

Awan, F.T. et al. "A Phase Ib/II Open-Label Study to Evaluate the Safety and Efficacy of TRU-016 in Combination with Bendamustine Versus Bendamustine Alone in Patients With Relapsed Chronic Lymphocytic Leukemia" J Clinc Oncol. 29: 2011 (Abstract e13053) 2 pgs.

Bendig, Mary M. "Humanization of Rodent Monoclonal Antibodies by CDR Grafting" Methods: A Companion to Methods in Enzymology (1995) 8, pp. 83-93.

Boulianne, Gabrielle L., et al; Production of Functional Chimaeric Mouse/Human Antibody; Database Biosis (Online) Biosciences Information Service, Philadelphia, PA, US; (1984) vol. 312, No. 5995, pp. 643-646.

Braslawsky, Gary R. et al. "Adriamycin (hydrazone)-antibody conjugates require internalization and intracellular acid hydrolysis for antitumor activity" Cancer Immunology Immunotherapy (1991) 33: pp. 367-374.

Butler, T. et al., "Biologic and clinical significance of molecular profiling in Chronic Lymphocytic Leukemia". Blood Reviews, 24, 2010, p. 135-141.

Byrd, J.C. et al., "Chronic Lymphocytic Leukemia", Hematology, American Socienty of Hematology, Washington, DC, Jan. 1, 2004, p. 163-183.

Cerri, M. et al. Abstract 0410 "TP53 Mutations and Del17P13 Predict Similar Outcome and Chemorefractoriness in Chronic Lymphocytic Leukemia." Haematologica, 2008, 93(s1):163.

Chang, H. et al., "Aberrant Nuclear p53 Expression Predicts Hemizygous 17p (TP53) Deletion in Chronic Lymphocytic Leukemia." Am J Clin Pathol, 2010, vol. 133, pp. 70-74.

Cheson, Bruce D. et al. "Optimal Use of Bendamustine in Chronic Lymphocytic Leukemia, Non-Hodgkin Lymphomas and Multiple Myeloma: Treatment Recommendations From an International Consensus Panel" Clincal Lymphoma, Myeloma & Leukemia (2010) vol. 10(1): pp. 21-27.

Dall'acqua, William F. et al. "Antibody humanization by framework shuffling" Methods 36 (2005) pp. 43-60.

Fischer, Kirsten et al. "Bendamustine in Combination with Rituximab (BR) for Patients with Relapsed Chronic Lymphocytic Leukemia (CLL): A Multicentre Phase II Trials of the German CLL Study Group (GCLLSG)" Blood (ASH Annual Meeting Abstracts) 2008; 112 Abstract 330, 2 pgs.

Furman, R.R. et al., "Phase 1 Dose Escalation Study of TRU-016, An Anti-CD37 SMIP (TM) Protein in Relapsed and Refractory CLL", Blood, American Society of Hematology, US, vol. 116, No. 21, Dec. 7, 2010, p. 31-32.

GenBank Accession ABJ97713, Anti-human CD37 mAb G28-1 immunoglobulin heavy chain variable region [Mus musculus], Aug. 1, 2007.

Gribben, J. G. "blood—How I treat CLL up front". Blood Journal, vol. 115, No. 2, Jan. 14, 2010, p. 186-197.

Hallek, M. et al., "Guidelines for the Diagnosis and Treatment of Chronic Lymphocytic Leukemia: A Report from the International Workshop on Chronic Lymphocytic Leukemia Updating the National Cancer Institute—Working Group 1996 Guidelines." Blood, 2008, vol. 111, No. 12, pp. 5446-5456.

Heider, Karl-Heinz et al. "A novel Fc-engineered monclonal antibody to CD37 with enhanced ADCC and high proapoptotic activity for treatment of B-cell malignancies" Blood (2011) 118, pp. 4159-4168.

International Search Report for PCT/EP2008/060464 dated Feb. 26, 2009.

Kienle, D. et al., "Gene expression factors as predictors of genetic risk and survival in chronic lymphocytic leukemia". Haematologica—The Hematology Journal, vol. 95, No. 1, Jan. 2010, p. 102-109.

Laurenti, L. et al., "New and Old Monoclonal Antibodies for the Treatment of Chronic Lymphocytic Leukemia". Mini Reviews in Medicinal Chemistry, Bentham Science Publishers, Hilversum, NL, vol. 11. No. 6, Jan. 1, 2011, p. 508-518.

Maddipatia, S. et al., "Augmented Anti-tumor Activity agaisnt B-Cell Lymphoma by a Combination of Monoclonal Antibodies Targeting TRAIL-R1 and CD20", Clinical Cancer Research, 2007, 13, p. 4556-4564.

Mohr, J. et al., Abstract 3119 "The Response to DNA Damage in CLL Cells is Partly Determined by the Type of TP53 Mutation and Genomic Aberrations." 2008, 112.

Montserrat, E. et al., "How I Treat Refractory CLL." Blood, 2006, vol. 107, No. 4, pp. 1276-1283.

NCBI GenBank Accession: AAB17008, Hu, W.X et al., "Comparison of NPC Transforming Gene Tx to Ig Kappa Constant Region Gene and Their Expresion in Different Cell Lines". Oct. 14, 1996.

NCBI GenBank Accession: CAC20454. McLean, G.R. et al., "Human and murine immunoglobulin expression vector cassettes", Feb. 9, 2001.

NCBI, GenBank Accession: ABJ97712. Ledbetter, J.A., et al., "Monoclonal antibodies to a new gp40-45 (CD37) B cell associated cluster group modulate B cell proliferation". Aug. 1, 2007.

Office Action—Final Rejection dated Mar. 6, 2013. U.S. Appl. No. 12/672,378, filed Apr. 14, 2010.

Office Action dated Mar. 6, 2013; U.S. Appl. No. 12/884,563, filed Sep. 17, 2010.

Office Action dated May 31, 2012; U.S. Appl. No. 12/672,378, filed Apr. 14, 2010.

Office Action dated Oct. 30, 2012; U.S. Appl. No. 12/672,378, filed Apr. 14, 2010.

Paul, W.E., Fundamental Immunology, 3rd Edition, 1993, pp. 292-295.

Presta, Leonard G. "Engineering of therapeutic antibodies to minimize immunogenicity and optimize function" Advanced Drug Delivery Reviews 58 (2006) pp. 640-656.

Qu, Q. et al., "Construction and Expression of Human-Mouse Chimeric Antibody against Human CD40", Journal of Cellular and Molecular Immunology (Chin J. Cell Mol Immunolo), 2006, 22(2), 189-192.

Rossi, D. et al., Abstract 3137 "The Prognostic Value of TP53 Mutations in Chronic Lymphocytic Leukemia (CLL) is Independent of del17p13: Implications for Overall Survival and Chemorefractoriness." 2008, vol. 112.

Rudikoff, Stuart et al. "Single amino acid substitution altering antigen-binding specificity" Proc., Natl. Acad. Sci. (1982) vol. 79, pp. 1979-1983.

Rummel, Mathias J. "German Experience with Bendamustine Treating Relapsed/Refractory Indolent B-Cell and Mantle Cell Lymphomas" (2007) Seminars in Hematology, pp. S22-S26.

Rummel, Mathias J. et al. "Bendamustine Plus Rituximab Versus CHOP Plus Rituximab in the First-Line Treatment of Patients with Indolent and Mantle Cell Lymphomas—First Interim Results of a Randomized Phase III Study of the StiL (Study Group Indolent Lymphomas, Germany)" Blood (ASH Annual Meeting Abstracts) 2007: 110: Abstract 385, 2 pgs.

Tsurushita, Naoya et al. "Design of humanized antibodies: From anti-Tac to Zenapax" Methods 36 (2005) pp. 69-83.

WO2005/017148-A1—Part 1 of 2—"Binding Constructs and Methods for Use Thereof". Applicant: Trubion Pharmaceuticals, Inc. International Publication date: Feb. 24, 2005. This is a large document that has been broken down into two parts for EFS validation.

(56) References Cited

OTHER PUBLICATIONS

WO2005/017148-A1—Part 2 of 2—"Binding Constructs and Methods for Use Thereof". Applicant: Trubion Pharmaceuticals, Inc. International Publication date: Feb. 24, 2005. This is a large document that has been broken down into two parts for EFS validation.

Zenz, T, et al., "Detailed analysis of p53 pathway defects in fludarabine-refractory chronic lymphocytic leukemia (CLL): dissecting the contribution of 17p deletion, TP53 mutation, P53-p21 dysfunction, and miR34a in a prospective clinical trial". Blood, vol. 114, No. 13, Sep. 2009, p. 2589-2597.

Zenz, T. et al. "In Vitro Activity of Type II anti-CD20 Anitbody GA101 in Refractory, Genetic High-Risk CLL". Blood (ASH Annual Meeting Abstracts), 2009, 114: Abstract 2379.

Zenz, T. et al., "Exceptional In Vitro Activity of CD37 Antibodies in CLL". Blood (ASH Annual Meeting Abstracts), Abstract 2460, vol. 116, No. 21, Dec. 7, 2010, p. 1021-1022.

Zenz, T. et al., "From pathogenesis to treatment of chronic lymphocytic leukemia". Nature Reviews/Cancer, vol. 10, Jan. 2010, p. 37-50.

Zenz, T. et al., "Monoallelic TP53 Inactivation is Associated with Poor Prognosis in Chronic Lymphocytic Leukemia: Results from a Detailed Genetic Characterization with Long-term Follow-up." Blood, 2008, vol. 112, No. 8, pp. 3322-3329.

Zenz, T. et al., Abstract 782 "17p Deletion in CLL: Detailed Analysis of TP53 Mutations, Alternative Mechanisms of p53 Inactivation, Clone Size and Clonal Evolution." 2008, 112.

Zhao, Z. et al., "Targeting CD37-positive lymphoid malignancies with a novel engineered small modular immunopharmaceutical". Blood, Oct. 1, 2007, LNKD-Pubmed:17440052, vol. 110, No. 7, p. 2569-2577.

Zucca, Emanuele et al. "Addition of rituximab to chlorambucil produces superior event-free survival in the treatment of patients iwth extranodal marginal-zone-B-cell lymphoma: 5 year analysis of the IELSG-19 Randonmized Study" AN: NLM23295789, Database Medline (2013) 2 pgs.

Cerveny, C.G. et al., "In vitro and in vivo anti-B cell lymphoma activities of TRU-016." Journal of Clinical Oncology, 2008 ASCO Annual Meeting Proceedings, 2008, vol. 26, No. 15S, 3074.

Heider, K-H. et al., "A novel Fc-engineered monoclonal antibody to CD37 with enhanced ADCC and high proapoptotic activity for treatment of B-cell malignancies." Blood, 2011, vol. 118, No. 15, pp. 4159-4168.

Krause, G. et al., "Action of novel CD37 antibodies on chronic lymphocytic leukemia cells." Leukemia, 2011, pp. 1-5.

Robak, T. et al., "TRU-016, a humanized anti-CD37 IgG fusion protein for the potential treatment of B-cell malignancies." Current Opinion in Investigational Drugs, 2009, vol. 10, No. 12, pp. 1383-1390.

Zucca, E et al., "Addition of Rituximab to Chlorambucil Produces Superior Event-Free Survival in the Treatment of Patients With Extranodal Marginal-Zone B-Cell Lymphoma: 5-Year Analysis of the IELSG-19 Randomized Study." Journal of Clinical Oncology, 2013, vol. 31, No. 5, pp. 565-572.

Carovsky, Chlorabucil-Still not Bad: A Reappraisal, Chronic Lymphocytic Leukemia, 2011, vol. 11.

Lazar, Greg A. et al. "Engineered antibody Fc variants with enhanced effector function" PNAS, Mar. 14, 2006, vol. 103, No. 11, pp. 4005-4010.

Smolej, How I treat Elderly or Cormorbid Patients with Chronic Lymphocytic Leukemia, Dept. of Hematology, University Hospital, Czech Republic, 2010, vol. 53, p. 201-220.

Andristos, L. et al., "A phase I trial of TRU-016, an anti-CD37 smaller modular immunopharmaceutical (SMIP) in relapsed and refractory CLL". 2009 ASCO Annual Meeting, Abstract No. 3017, Poster Discussion, Journal of Clinical Oncology, American Society of Clinical Oncology, U.S. vol. 27, No. 15s, Jan. 1, 2009.

Jin, Lei et al. "SMIP-016 in Action: CD37 as a Death Receptor" (2012) Cancer Cell, 21, 597-598.

Kroschinsky, F. et al. "Phase I Dose-Escalation Study of BI 836826 in Patients (PTS) with Relapsed or Refractory Non-Hodgkin Lymphoma (NHL) of B Cell Origin" (2015) Hematological Oncology, Supp 1, 243, Abstract 286, P15-06950, 1 pg.

Kroschinsky, Frank et al. "Phase I Dose-Escalation Study of BI 836826 (CD37 Antibody) in Patients with Relapsed or Refractory Non-Hodgkin Lymphoma of B Cell Origin" (Jun. 17, 2015) Poster, Presented at the 13th International Conference on Malignant Lymphoma, Lugano Switzerland.

Quintero-Hernandez, Veronica, et al. "Evaluation of three different formats of a neutralizing single chain human antibody against toxin Cn2: Neutralization capacity versus thermodynamic stability" (2012) Immunology Letters, 143, 152-160.

Robak, Tadeusz et al. "Randomized phase 2 study of otlertuzumab and bendamustine versus bendamustine in patients with relapsed chronic lymphocytic leukaemia" (2017) British Journal of Haematology, 176. 618-628.

Rossi, D. et al., "The Prognostic Value of TP53 Mutations in Chronic Lymphocytic Leukemia (CLL) is Independent of Del17p13: Implications for Overall Survival and Chemorefractoriness." (2008) Clinical Cancer Research, vol. 15, 995-1004 (entire article).

Smolewski, Piotr et al. "Pro-apoptotic effect of an anti-CD37 scFv-Fc fusion protein, in combination with the anti-CD20 antibody, ofatumumab, on tumour cells from B-cell malignancies" (2014) European Journal of Cancer, 50, 2677-2684.

Stilgenbauer, S. et al. "Phase I, First-In-Human Trial of BI 836826 (An Anti-CD37 Antibody) in Patients (PTS) with Relapsed/Refractory (R/R) Chronic Lymphocytic Leukemia (CLL)", (2015) Heamatolgica, Supp 1, 225, Abstract P589, P15-08941, 2 pgs.

Stilgenbauer, S. et al. "Phase I, First-in-Human Trial of BI 836826 (CD37 Antibody) in Patients with Relapsed/Refractory Chronic Lymphocytic Leukaemia" (2015) Poster. Presented at the 20th Congress of the European Hematology Association, Vienna, Austria, 1 pg.

\* cited by examiner

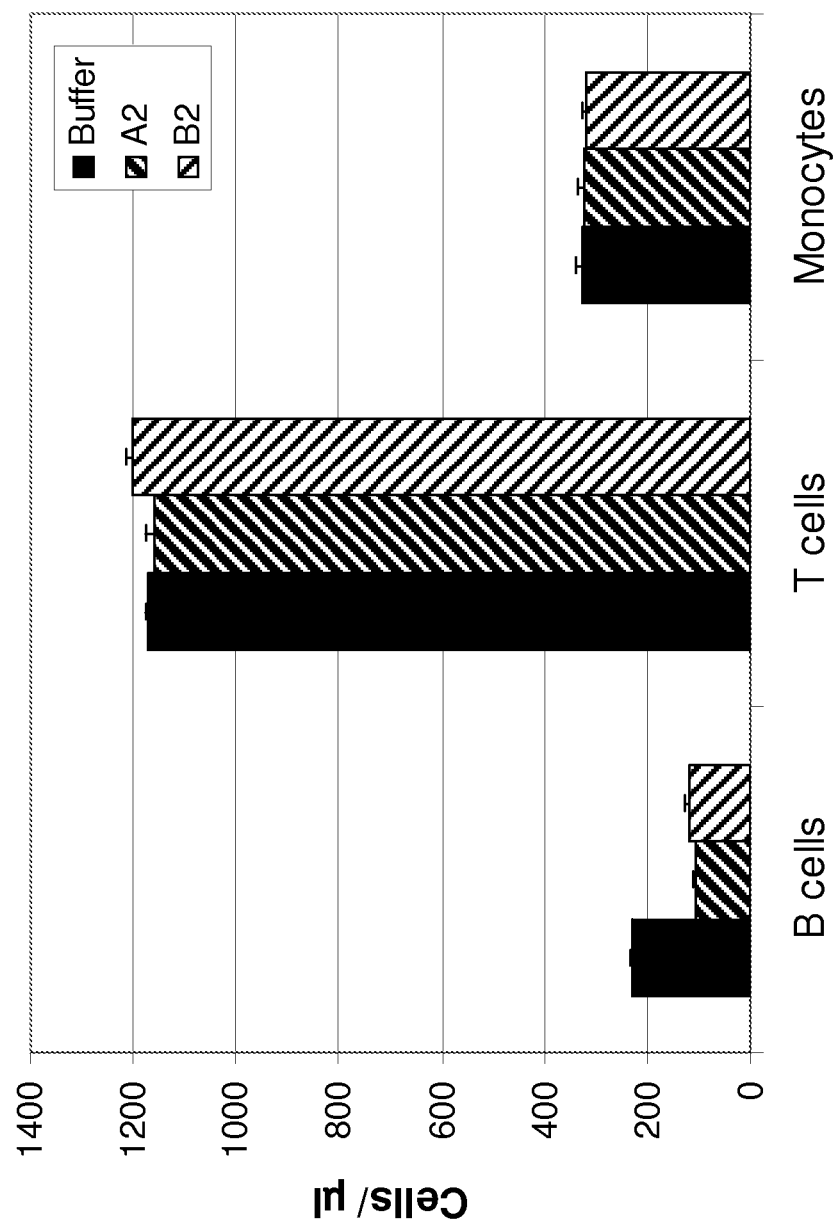

ANTI CD37 ANTIBODIES

INTRODUCTION

The present invention relates to immunotherapies that are based on B cell depletion. In particular, the present invention relates to anti-CD37 antibody molecules for use in such therapies, e.g. in the treatment of B cell malignancies and autoimmune conditions.

Immunotherapy using monoclonal antibodies (mAbs) has been emerging as a safe and selective method for the treatment of cancer and other diseases. In particular, the role of monoclonal antibodies in therapies that are based on B cell depletion, e.g. in the treatment of B cell malignancies, has expanded since the introduction of rituximab (Rituxan®), an antibody that is directed against the CD20 antigen on the B cell surface. Numerous studies have confirmed the efficacy of rituximab as a single agent and in combination therapy in low-grade NHL (Hiddemann et al., 2005a; Hiddemann et al., 2005b; Hainsworth 2004; McLaughlin et al., 1998), mantle cell lymphoma (Forstpointner et al., 2004; Kahl et al., 2006; Foran et al., 2000; Howard et al., 2002; Romaguera et al., 2005), diffuse large cell lymphoma (DLCL) (Coiffier et al., 1998; Feugier et al., 2005), and Burkitt leukemia/lymphoma (Thomas et al., 2006). However, only a subset of patients respond to therapy and the majority of those eventually relapse following rituximab treatment. Therefore, new therapeutic targets on B cells have been sought that are potentially more effective than CD20 for therapy of B cell malignancies (Zhao et al., 2007). The CD37 antigen is a cell surface antigen that has, to date, not been considered as a target for B cell malignancies to the same extent as the B cell antigen CD20.

CD37, a member of the tetraspanin superfamily, is a heavily glycosylated cell surface molecule with four transmembrane domains and two extracellular loops. CD37 is almost exclusively expressed on mature B cells, with highest expression levels on peripheral blood B cells, reduced levels on plasma cells and non-detectable levels on CD10+ precursor B cells in the bone marrow. Low level expression of CD37 has also been reported on resting and activated T cells, granulocytes, and monocytes. In B cell neoplasm, CD37 expression is mainly observed in aggressive non-Hodgkin's lymphoma (NHL) and chronic lymphoid leukemia (CLL). High level of CD37 expression is also found on mantle cell lymphoma (MCL). This expression pattern makes CD37 an attractive target for antibody-mediated cancer therapy.

CD37 was first described in 1986 and characterized by the murine monoclonal antibody MB-1 (Link et al., 1986).

The physiological role of CD37 is unknown. Mice deficient for CD37 display no changes in development and cellular composition of lymphoid organs, but have reduced levels of IgG1 and attenuated T cell mediated immune reactions (Knobeloch et al., 2000). Studies with CD37$^{-/-}$ T cells suggest a role for CD37 in T cell proliferation (van Spriel et al., 2004).

CD37 expression on malignant B cells of various diseases has been reported. CD37 is expressed in the majority of mature B cell malignancies like Burkitt lymphoma, follicular lymphoma and lymphocytic lymphoma (Link et al., 1986). High levels of CD37 expression have been observed in hairy cell leukemia and in samples of patients with chronic lymphocytic leukemia (CLL) and different subtypes of non-Hodgkin's lymphoma (NHL) including mantle cell lymphoma (MCL) (Schwartz-Albiez et al., 1988; Barrena et al., 2005). One report utilizing antibody micro array for immunophenotyping claims CD37 to be a good discriminator between malignant CLL cells (high CD37 expression) versus normal peripheral blood (PB) lymphocytes (low CD37 expression) (Belov et al., 2001).

Binding of a CD37-specific mAb to cancer cells may trigger various mechanisms of action: First, after the antibody binds to the extracellular domain of the CD37 antigen, it may activate the complement cascade and lyse the targeted cell. Second, an anti-CD37 antibody may mediate antibody-dependent cell-mediated cytotoxicity (ADCC) to the target cell, which occurs after the Fc portion of the bound antibody is recognized by appropriate receptors on cytotoxic cells of the immune system.

Third, the antibody may alter the ability of B cells to respond to antigen or other stimuli. Finally, anti-CD37 antibody may initiate programmed cell death (apoptosis).

Anti-CD37 mAb MB-1 was evaluated in two radioimmunotherapy trials in B-NHL patients (B-cell non-Hodgkin's lymphoma; Press et al., 1989; Kaminski et al., 1992). Therapeutic doses of $^{131}$I-MB-1 were administered to 6 relapsed NHL patients in one trial and all 6 patients achieved a clinical complete remission (CR) with a median duration of 7 months. Of note, two of the six patients showed clinical regressions already after administration of only the tracer dose of MB-1 suggesting a direct anti-tumor effect of the antibody itself. In the second trial radiolabeled MB-1 was applied for the treatment of refractory NHL patients and resulted in 3 out of 9 evaluable patients with objective responses of limited duration (Kaminski et al., 1992). In both trials a rapid and transient depletion of peripheral B cells after injection of the trace labeled MB-1 antibody dose was reported. These observations support the conclusion that MB-1 exerts a cytotoxic activity on its own. In summary, these clinical trials underscore the feasibility of CD37-targeting for B-cell malignancies and point to a potential clinical relevance of anti-CD37 therapy.

There is experimental evidence with a CD37 specific antibody-like single chain molecule ("Small Modular ImmunoPharmaceutical", SMIP) that treatment with that molecule induces apoptosis in vitro and delays Burkitt lymphoma growth in a xenograft model in vivo. Antiapoptotic activity of the recombinant anti-CD37 SMIP Tru16.4 from Trubion was described recently (Zhao et al., 2004). Tru 16.4 induced caspase-independent apoptosis on primary CLL cells from tumor patients. Induction of apoptosis on these cells was greater than that of Rituximab and comparable to that of Alemtuzumab, a CD52 antagonist. The degree of apoptosis induction was directly proportionate to CD37 cell surface expression and could be further enhanced by cross-linking with an anti-human IgG antibody. A correlation of CD37 expression and ADCC was demonstrated on cell lines in vitro. In a Burkitt lymphoma mouse model (Raji) treatment with anti-CD37 scFv revealed therapeutic efficacy (Zhao et al., 2007). These data provide first evidence that CD37-targeting is a promising approach for targeted anti-tumor therapy by induction of apoptosis and ADCC.

In conclusion, it has been shown that the CD37 antigen is frequently expressed on tumor cells in several human B cell malignancies and on mature normal B lymphocytes and that anti-CD37-based therapy may be a promising approach for treating B cell malignancies. The depletion of CD37-positive normal B cells is not considered critical since clinical data from numerous patients show that even prolonged depletion of B cells up to 6 months with an anti-CD20 mAb does not significantly reduce IgG serum levels or increases the risk of infections (Van der Kolk et al., 2002).

Although the anti-CD37 antibodies or antibody-like molecules described above (MB-1 and SMIP Tru16.4) have shown anti-tumor efficacy in B-cell malignancies and the potential to target CD37, there is a need for alternate anti-CD37 inhibitors to improve therapies based on B-cell depletion.

SUMMARY OF INVENTION

It was an object of the invention to provide novel CD37 antagonists for the treatment of B cell malignancies and other disorders which respond to the depletion of CD37 positive B cells.

Furthermore, it was an object of the invention to provide anti-CD37 antibodies with improved effector functions. In particular, the inventors sought to provide anti-CD37 mABs with antibody-dependent cell-mediated cytotoxicity (ADCC).

To solve the problem underlying the invention, a murine monoclonal anti-CD37 antibody was used as a starting antibody for generating chimeric and humanized anti-CD37 antibodies that are useful in human therapy.

In a first aspect, the present invention provides an antibody molecule that binds to human CD37 and that is derived from
 a) a murine monoclonal antibody that is defined by
  i. a variable heavy chain comprising the amino acid sequence shown in SEQ ID NO: 2; and
  ii. a variable light chain comprising the amino acid sequence shown in SEQ ID NO:4, or from
 b) a non-human antibody recognizing the same epitope of human CD37 as the antibody defined in a) or recognizing an epitope that is close to or overlaps with said epitope;
wherein said antibody molecule is a chimeric or a humanized antibody.

As will be understood from the following, an antibody that is "derived" from another antibody, i.e. the starting antibody, means that said antibody has been generated by modification of the starting antibody as described below.

In a preferred embodiment, the antibody molecule is a chimeric or humanized antibody molecule derived from the starting antibody defined in a). An antibody with a related sequence was designated G28.1 and described in WO 2005/017148.

The starting antibody of category b) may, for example, be selected from the CD37-specific antibodies that characterized, like G28.1, the CD37 antigen in the Third HLDA Workshop; these antibodies were designated HD28, HH1, BI14, F97-3G6 (Ling and MacLennan, 1987). Other CD37-specific antibodies that have been described include RFB-7, Y29/55, MB-1, M-B371, M-B372 and IPO-24. According to Moldenhauer, 2000, and Schwartz-Albiez et al., 1988, all these antibodies (including G28.1) recognize the same or an overlapping or close CD37 epitope. Schwartz-Albiez et al., 1988, indicates that the epitope is situated in the carbohydrate moiety of CD37. A number of the above antibodies is commercially available, e.g. HH1 (SantaCruz), RFB-7 (Biodesign), Y29/55 (Biogenesis), M-B371 (BD Biosciences), M-B372 (SantaCruz) and IPO-24 (AbCam).

Other CD37– specific antibodies are S-B3 (Biosys), NMN46 (Chemicon), and ICO-66 (Bioprobe). Whether an antibody recognizes the same epitope as G28.1 can be determined by competitive binding assays or by cross inhibition radioimmunoassays as described by Moldenhauer et al., 1987, and Moldenhauer, 2000.

By way of example, competitive binding may be determined in an ELISA, using plates coated with CD37 protein or CD37 peptides or with CD37 positive cells (Cell ELISA) and measuring binding of biotinylated antibody in the presence of a competitor candidate antibody. In the presence of a competing antibody or antibody-derived fragment, the binding of biotinylated G28.1 (or another antibody known to recognize the same epitope) is reduced in the case that the antibodies recognize a shared epitope. To identify the G28.1 epitope peptide, fragments or short polypeptides or recombinant proteins derived from the CD37 sequence can be synthesized or produced and the binding of G28.1 to said peptides/polypeptides measured in an ELISA assay. Competitive binding can also be determined by FACS analysis, as described in the Examples.

An antibody defined in b) may be used in an analogous manner as G28.1 as a starting antibody for the generation of chimeric or humanized antibody molecules.

A starting antibody of category b) may also be generated de novo by using peptides or protein fragments containing the relevant epitope, or DNA molecules encoding such peptides/fragments, respectively for immunization to obtain antibodies reactive with the same epitope as G28.1.

A starting antibody b) may also be obtained by immunization with whole cells carrying the relevant epitope; the thus obtained hybridoma cells are then screened for competitive binding of the secreted antibodies.

The term "anti-CD37 antibody molecule" encompasses anti-CD37 antibodies and anti-CD37 antibody fragments as well as conjugates with antibody molecules. Antibodies include, in the meaning of the present invention, chimeric monoclonal and humanized monoclonal antibodies. The term "antibody", which may interchangeably be used with "antibody molecule", shall encompass complete immunoglobulins (as they are produced by lymphocytes and for example present in blood sera), monoclonal antibodies secreted by hybridoma cell lines, polypeptides produced by recombinant expression in host cells, which have the binding specificity of immunoglobulins or monoclonal antibodies, and molecules which have been derived from such antibodies by modification or further processing while retaining their binding specificity.

In an embodiment of the invention, the anti-CD37 antibody molecule is a chimeric antibody defined by
 i) a variable heavy chain comprising the amino acid sequence shown in SEQ ID NO: 2;
 ii) a variable light chain comprising the amino acid sequence shown in SEQ ID NO:4;
 iii) constant heavy and light chains that are of human origin.

The construction and production of chimeric mouse/human antibodies is well known in the art (Boulianne et al., 1984). The variable regions of the non-human antibody are typically linked to at least a portion ($F_C$) of the immunoglobulin constant region of a human immunoglobulin. Human constant region DNA sequences can be isolated in accordance with well-known procedures from a variety of human cells, preferably from immortalized B cells (see Kabat et al., 1991; and WO 87/02671). The antibody molecules may contain all or only a portion of the constant region as long as they exhibit specific binding to the CD37 antigen and the Fc receptors. The choice of the type and length of the constant region depends on whether effector functions like complement fixation or antibody-dependent cell-mediated toxicity are desired, and on the desired pharmacological properties of the antibody molecule.

In certain embodiments, the antibody molecule of the invention is a chimeric CD37-specific antibody that has the heavy chain variable region of a non-human antibody defined in a) or b) fused to the human heavy chain constant region IgG1 and the light chain variable region of a non-human antibody defined in a) or b) fused to the human light chain constant region kappa.

In yet another embodiment, the antibody molecule is a chimeric CD37-specific antibody that has the heavy chain variable region shown in SEQ ID NO:2 fused to the human heavy chain constant region IgG1 which is an IgG1 molecule with the sequence shown in SEQ ID NO:24 (coding DNA sequence: SEQ ID NO: 23) or a mutated IgG1 molecule derived therefrom and that has the light chain variable region shown in SEQ ID NO:4 fused to the human light chain constant region kappa shown in SEQ ID NO:26 (coding DNA sequence: SEQ ID NO: 25).

Other human constant regions for chimerizing a non-human starting antibody defined in a) or b) are available to the person skilled in the art, e.g. IgG2, IgG3, IgG4, IgA, IgE or IgM (instead of IgG1) or lambda (instead of kappa). The constant regions may also be chimeric, for example, a heavy chain IgG1/IgG2 or IgG1/IgG3 chimera.

In certain embodiments of the invention, the anti-CD37 antibody molecule is a humanized antibody that is defined by i. CDRs contained within the variable heavy chain as shown in SEQ ID NO:2 and by
ii. CDRs contained within the variable light chain as shown in SEQ ID NO:4,
iii. frameworks supporting said CDRs that are derived from a human antibody,
iv. constant heavy and light chains that are from a human antibody.

Humanized forms of non-human (e.g. murine, rat or rabbit antibodies) antibodies are immunoglobulins, immunoglobulin chains or fragments thereof (such as Fv, Fab, Fab', F(ab')$_2$ or other antigen-binding molecules with subsequences of antibodies) that contain minimal sequences derived from non-human immunoglobulin.

Humanized antibodies include human immunoglobulins (from the recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues.

In the humanized antibodies of the invention, the sequences encoding CDRs of a non-human starting antibody defined in a) or b) have been grafted into the respective genes of human immunoglobulin heavy and light chains.

"Complementarity determining regions" (CDRs) of a monoclonal antibody are understood to be those amino acid sequences involved in specific antigen binding according to Kabat et al., 1991, in connection with Chothia and Lesk (1987). From the sequences of the variable regions as shown in SEQ ID NO:2 and SEQ ID NO:4, the CDR sequence can be routinely determined by searching the Kabat sequence database for sequence features.

Techniques for obtaining humanized antibodies are routinely available to the skilled person, they have been described, inter alia, in U.S. Pat. No. 5,225,539; U.S. Pat. No. 6,548,640; and U.S. Pat. No. 6,982,321.

Appropriate framework residues of the CDR-grafted antibody may be reverted to murine residues to improve binding affinity. As described above, from methods pertinent to the art, the expert knows how to obtain the CDRs from a given non-human antibody, to choose and obtain appropriate human immunoglobulin genes, to graft the CDRs into these genes, to modify selected framework residues, to express the CDR-grafted antibody in appropriate host cells, e.g. Chinese hamster ovary (CHO) cells, and to test the resulting recombinant antibodies for binding affinity and specificity.

To obtain a humanized antibody, the antigen binding sites, which are formed by the CDRs of the heavy chain and CDRs of the light chain, are excised from the DNA of cells secreting the rodent (murine) monoclonal antibody and grafted into the DNA coding for the framework of the human antibody.

Alternatively to CDR grafting, non-human, in particular murine, anti-CD37 antibodies can be humanized by the so-called "resurfacing" technology, whereby the rodent frameworks are left unchanged with the exception of surface-exposed residues, as described in U.S. Pat. No. 5,639,641.

In a further aspect, the invention relates to humanized antibodies having a variable heavy chain with a sequence shown in SEQ ID NO:6 and a variable light chain with a sequence selected from the sequences shown in SEQ ID NO:12, SEQ ID NO:14, SEQ ID NO:16, SEQ ID NO:18, SEQ ID NO:20 and SEQ ID NO:22.

In another aspect, the invention relates to humanized antibodies having a variable heavy chain with a sequence shown in SEQ ID NO:8 and a variable light chain with a sequence selected from the sequences shown in SEQ ID NO:12, SEQ ID NO:14, SEQ ID NO:16, SEQ ID NO:18, SEQ ID NO:20 and SEQ ID NO:22.

In another aspect, the invention relates to humanized antibodies having a variable heavy chain with a sequence shown in SEQ ID NO:10 and a variable light chain with a sequence selected from the sequences shown in SEQ ID NO:12, SEQ ID NO:14, SEQ ID NO:16, SEQ ID NO:18, SEQ ID NO:20 and SEQ ID NO:22.

The above defined humanized antibodies are shown in Table 1.

In certain embodiments, the humanized antibody has a human heavy chain constant region IgG1 and a human light chain constant region kappa. As described above for the chimeric antibodies, the constant regions may be selected from other classes and subclasses.

In certain embodiments, in humanized antibodies of the invention, the human constant heavy chain IgG1 is an IgG1 molecule with the sequence shown in SEQ ID NO:24 or a mutated IgG1 molecule derived therefrom and the human light chain constant region kappa has the sequence shown in SEQ ID NO:26.

Anti-CD37 antibody molecules of the invention may also be variants of the antibodies that are defined by the amino acid sequences shown in the sequence listing. Using routinely available technologies, the person skilled in the art will be able to prepare, test and utilize functional variants of the above-defined antibodies. Examples are variant antibodies with at least one position in a CDR and/or framework altered, variant antibodies with single amino acid substitutions in the framework region where there is a deviation from the germline sequence, antibodies with conservative amino substitutions, antibodies that are encoded by DNA molecules that hybridize, under stringent conditions, with the DNA molecules presented in the sequence listing encoding antibody variable chains.

Given the properties of individual amino acids, rational substitutions can be performed to obtain antibody variants that conserve the overall molecular structure of the starting antibody. Amino acid substitutions, i.e., "conservative substitutions", may be made, for instance, on the basis of similarity in polarity, charge, solubility, hydrophobicity, hydrophilicity, and/or the amphipathic nature of the respective amino acid. The skilled person is familiar with commonly practiced amino acid substitutions, as described e.g. in WO 2007/042309, and methods for obtaining thus modified antibodies. Given the genetic code and recombinant and synthetic DNA techniques, DNA molecules encoding variant antibodies with one or more conservative amino acid exchanges can be routinely designed and the respective antibodies readily obtained.

In comparison with an antibody as defined by its variable chains shown in the sequence listing, antibody variants encompassed by the invention have a sequence identity in the CDR regions of at least 60%, more preferably, at least 70% or 80%, still more preferably at least 90% and most preferably at least 95%. Preferred antibodies also have a sequence similarity in the CDR regions of at least 80%, more preferably 90% and most preferably 95%. Preferred antibody variants have a sequence identity in the variable regions of at least 60%, more preferably, at least 70% or 80%, still more preferably at least 90% and most preferably at least 95%. Preferred antibodies also have a sequence similarity in the variable regions of at least 80%, more preferably 90% and most preferably 95%.

"Sequence identity" between two polypeptide sequences indicates the percentage of amino acids that are identical between the sequences. "Sequence similarity" indicates the percentage of amino acids that either are identical or that represent conservative amino acid substitutions.

A variant may also be obtained by using an antibody with a defined sequence as shown in the sequence listing as a starting point for optimization and diversifying one or more amino acid residues, preferably amino acid residues in one or more CDRs, and by screening the resulting collection of antibody variants for variants with improved properties. Diversification of one or more amino acid residues in CDR3 of the variable light chain, CDR3 of the variable heavy chain, CDR1 of the variable light and/or CDR2 of the variable heavy chain has been proven useful. Diversification can be done by methods known in the art, e.g. the so-called TRIM technology referred to in WO 2007/042309.

In a further embodiment, the anti-CD37 antibody molecule of the invention is an "affinity matured" antibody.

An "affinity matured" anti-CD37 antibody is an anti-CD37 antibody derived from an antibody with the sequences shown in the sequence listing, that has one or more alterations in one or more CDRs which result in an improvement in the affinity for the antigens, compared to the respective original non-matured antibody. One of the procedures for generating such antibody mutants involves phage display (Hawkins et al., 1992; and Lowman et al., 1991). Briefly, several hypervariable region sites (e.g. 6-7 sites) are mutated to generate all possible amino acid substitutions at each site. The antibody mutants thus generated are displayed in a monovalent fashion from filamentous phage particles as fusions to the gene III product of M13 packaged within each particle. The phage-displayed mutants are then screened for their biological activity (e.g. binding affinity) as herein disclosed.

Affinity matured antibodies may also be produced by methods as described, for example, by Marks et al., 1992, (affinity maturation by variable heavy chain (VH) and variable light chain (VL) domain shuffling), or Barbas, et al., 1994; Shier et al., 1995; Yelton et al., 1995; Jackson et al., 1995; and Hawkins et al., 1992 (random mutagenesis of CDR and/or framework residues). Preferred affinity matured antibodies will have nanomolar or even picomolar affinities for the target antigen. In a further embodiment, the anti-CD37 antibody molecule of the invention is a "de-immunized" antibody.

A "de-immunized" anti-CD37 antibody is an antibody derived from a humanized or chimeric antibody with a sequence shown in the sequence listing, that has one or more alterations in its amino acid sequence which result in a reduction of immunogenicity of the antibody, compared to the respective original non-dehumanized antibody. One of the procedures for generating such antibody mutants involves the identification and removal of T-cell epitopes of the antibody molecule (Baker and Jones, 2007). In a first step, the immunogenicity of the antibody molecule can be determined by several methods, e.g. by in vitro determination of T-cell epitopes or in silico prediction of such epitopes, as has been described in the literature (Jones et al., 2004; Jones et al., 2005; Reche et al., 2004; Hertz et al., 2006). Once the critical residues for T-cell epitope function have been identified, mutations can be made to remove immunogenicity and retain antibody activity (Jones et al., 2005; Tangri et al., 2005). Methods for introduction of mutations in proteins are well-known in the art, e.g. by overlapping PCR techniques.

Since the Fc region of an antibody interacts with a number of Fc receptors, which results in a number of important functional capabilities (which are referred to as "effector functions"), the antibody is, in certain embodiments, a full length antibody or an antibody that contains a portion of the Fc region, the latter as long as the antibody exhibits specific binding both to the relevant portion of the antigen and to Fc receptors. The choice of the type and length of the constant region depends on whether effector functions like complement fixation or antibody-dependent cell-mediated cytotoxicity are desirable features, and on the desired pharmacological properties of the antibody protein.

In an embodiment of the invention, the anti-CD37 antibody is a chimeric or humanized antibody with an Fc region, or the relevant section thereof, that has been engineered to modulate effector functions, in particular to enhance binding of the antibody to one or more Fc receptors, thereby enhancing the effector function ADDC. Engineering of the Fc region mediates the antibody's effector function in the presence of effector cells more effectively than that of the non-Fc-engineered parent antibody. In one embodiment, such antibody variant mediates ADCC that is greater than that mediated by the parent antibody. (In the following, if not otherwise stated, the term "parent" in the context of an antibody molecule, or in the context of IgG or the Fc region, refers to the non-engineered antibody molecule, Fc region or IgG, respectively, from which the mutated (engineered) molecule is derived.)

A variety of modifications of the Fc region have been suggested in the art, both in the scientific literature and in patent documents, e.g. in EP 0307434, WO 9304173, WO 9734631, WO 9744362, WO 9805787, WO 9943713, WO 9951642, WO 9958572, WO 02060919, WO 03074679, WO 2004016750, WO 2004029207, WO 2004063351, WO 2004074455, WO 2004035752, WO 2004099249, WO 2005077981, WO 2005092925, WO 2006019447, WO 2006031994, WO 2006047350, WO 2006053301, WO 2006088494 and WO 2007041635.

In preferred embodiments, the antibodies of the invention are Fc variants with amino acid substitutions at positions 332 and/or 239 and/or 236. In preferred embodiments, the antibodies of the invention have mutations in the Fc domain selected from the group of i) a single substitution at position 332, preferably I332E;
ii) a combination of substitutions at positions 239 and 332, preferably S239D/I332E;
iii) a combination of substitutions at positions 236 and 332, preferably G236A/I332E;
iv) a combination of substitutions at positions 236, 239 and, 332, preferably G236A/S239D/I332E.

The above defined substitutions have, for example, been described by Lazar et al., 2006, in WO 2004029207 and WO 2007041635.

The Fc variants in the antibodies of the present invention are defined according to the amino acid modifications that compose them. Thus, for example, I332E is an Fc variant with the substitution I332E relative to the parent Fc polypeptide. Likewise, S239D/I332E defines an Fc variant with the substitutions S239D and I332E and S239D/I332E/G236A defines an Fc variant with the substitutions S239D, I332E, and G236A relative to the parent Fc polypeptide.

Numbering is according to the EU numbering scheme (Kabat et al., 1991), which refers to the numbering of the EU antibody (Edelman et al., 1969). The person skilled in the art will appreciate that these conventions consist of nonsequential numbering in specific regions of an immunoglobulin sequence, enabling a normalized reference to conserved positions in immunoglobulin families.

In the above defined antibodies, the substituted positions 236, 239 and 332 correspond to positions 119, 122 and 215, respectively, of the IgG1 heavy chain depicted in SEQ ID NO:24. (In the full-length sequences of the heavy chains of antibodies A2, A4, B2 and B4 shown in SEQ ID NOs: 28, 32, 36 and 40, the substituted amino acids are at positions 235, 238 and 331).

In certain embodiments, the Fc variants of the invention are based on human IgG sequences, and thus human IgG sequences are used as the "base" sequences against which other sequences are compared. For the antibodies of the present invention, the engineered Fc region is preferably IgG, in particular IgG1, but it may also be IgG2 or variant sequences from other immunoglobulin classes such as IgA, IgE, IgGD, IgM or chimeric versions of two or more immunoglobulin classes (e.g. IgG2/IgG1) and the like. Although the Fc variants of the present invention are engineered in the context of one parent IgG, the variants may be engineered in or "transferred" to the context of another, second parent IgG. This is done by determining the "equivalent" or "corresponding" residues and substitutions between the first and second IgG, typically based on sequence or structural homology between the sequences of the first and second IgGs. In order to establish homology, the amino acid sequence of a first IgG outlined herein is directly compared to the sequence of a second IgG. After aligning the sequences, using one or more of the homology alignment programs known in the art, allowing for necessary insertions and deletions in order to maintain alignment (i.e., avoiding the elimination of conserved residues through arbitrary deletion and insertion), the residues equivalent to particular amino acids in the primary sequence of the first Fc variant are defined. Regardless of how equivalent or corresponding residues are determined, and regardless of the identity of the parent IgG in which the IgGs are made, what is meant to be conveyed is that the Fc variants used in the present invention may be engineered into any second parent IgG that has significant sequence or structural homology with the Fc variant. Thus for example, if a variant antibody is generated wherein the parent antibody is human IgG1, by using the methods described above or other methods for determining equivalent residues, the variant antibody may be engineered, for example, in a human IgG2 parent antibody, a human IgA parent antibody (see WO 2007041635).

The antibodies of the invention target the antigen CD37, which may be advantageous over targeting CD20 in diseases in which the level of CD37 expression is higher than that of CD20, as e.g. in chronic lymphocytic leukemia, where samples have shown high levels of CD37 mRNA expression compared to low level expression of CD20 mRNA.

It has been shown that antibodies of the invention are superior to rituximab, a registered anti-CD20 antibody, with respect to ADCC activity on Ramos cells, normal B cell depletion in whole blood and Ramos Burkitt's lymphoma cell depletion. As could be shown in the experiments of the invention, the antibodies of the invention (both the non-Fc engineered and the Fc-engineered ones) have a B cell depleting activity that is superior to that of rituximab. The antibodies with the mutated Fc region show a ca. 10 fold increase of B cell depletion activity as compared to rituximab (FIG. 11B).

Representatives of CD37 antibodies of the invention show potent pro-apoptotic activity without cross-linking; in this respect, antibodies with this property are superior to the anti-CD37 SMIP Tru16.4, which does not show apoptosis without cross-linking (Zhao et al., 2007). Induction of apoptosis without cross-linking, which could be shown for antibodies of the invention both with and without Fc engineering, is advantageous in the absence of a cross-linking agent in vivo (e.g. effector cells harboring Fcγ receptors) or at low density of the target antigen CD37 (e.g. tumor cells with low level expression of CD37). An antibody which induces apoptosis without cross-linking may still cause cell death, whereas an antibody dependent on cross-linking does not.

In a further aspect, an anti-CD37 antibody molecule of the invention is an antibody fragment that is derived from a humanized or chimeric CD37 specific antibody according to the present invention. To obtain antibody fragments, e.g. Fab fragments, digestion can be accomplished by means of routine techniques, e.g. using papain. Examples of papain digestion are described in WO 94/29348 and U.S. Pat. No. 4,342,566. Papain digestion of antibodies typically produces two identical antigen binding fragments, so-called Fab fragments, each with a single antigen binding site, and a residual Fc fragment. Pepsin treatment yields an F(ab')$_2$ fragment that has two antigen combining sites and is still capable of cross-linking the antigen.

The Fab fragments obtained by digestion of the antibody also contain the constant domains of the light chain and the first constant domain (CH$_1$) of the heavy chain. Fab' fragments differ from Fab fragments in that they contain additional residues at the carboxy terminus of the heavy chain CH$_1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Antibody fragments can also be generated by molecular biology methods producing the respective coding DNA fragments.

The antibody molecule will typically be a tetramer consisting of two light chain/heavy chain pairs, but may also be dimeric, i.e. consist of a light chain/heavy chain pair, e.g. a Fab or Fv fragment, or it may be a monomeric single chain antibody (scFv; Johnson and Bird, 1991), a minibody, or a diabody.

The anti-CD37 antibody molecule may also be in the form of a conjugate, i.e. an antibody molecule that is chemically coupled to a cytotoxic agent, particularly a cytotoxic agent that induces cytotoxicity (e.g. apoptosis or mitotic arrest) of tumor cells. As a result of normal pharmacologic clearance mechanisms, an antibody employed in a drug conjugate (an "immunoconjugate") contacts and binds to target cells only in limited amounts. Therefore, the cytotoxic agent employed in the conjugate must be highly cytotoxic such that sufficient cell killing occurs to elicit a therapeutic effect. As described in US 2004/0241174, examples of such cytotoxic agents include taxanes (see, e.g. WO 01/38318 and WO 03/097625), DNA-alkylating agents (e.g., CC-1065 analogs), anthracyclines, tubulysin analogs, duocarmycin analogs, doxorubicin, auristatin E, ricin A toxin, and cytotoxic agents comprising a reactive polyethylene glycol moiety (see, e.g., Sasse et al., 2000; Suzawa et al., 2000; Ichimura et al., 1991; Francisco et al., 2003; U.S. Pat. No. 5,475,092; U.S. Pat. No. 6,340,701; U.S. Pat. No. 6,372,738; and U.S. Pat. No. 6,436,931; US 2001/0036923; US 2004/0001838; US 2003/0199519; and WO 01/49698).

In a preferred embodiment, the cytotoxic agent is a maytansinoid, i.e. a derivative of maytansine (CAS 35846538), maytansinoids being known in the art to include maytansine, maytansinol, C-3 esters of maytansinol, and other maytansinol analogues and derivatives (see, e.g., U.S. Pat. No. 5,208,020; and U.S. Pat. No. 6,441,163).

Anti-CD37 antibody immunoconjugates may be designed and synthesized as described in WO 2007/077173 for anti-FAP immunoconjugates.

In a further embodiment, the anti-CD37 molecule of the invention may be radioactively labeled to form an radioimmunoconjugate, an approach suggested for the anti-CD37 antibody MB-1 (Buchsbaum et al., 1992, see above). Radionuclides with advantageous radiation properties are known in the art, examples are Phosphorus-32, Strontium-89, Yttrium-90, Iodine-131, Samarium-153, Erbium-169, Ytterbium-175, Rhenium-188, that have been successfully and stably coupled to MAbs. The anti-CD37 antibody molecules of the invention may be labeled with various radionuclides using direct labeling or indirect labeling methods known in the art, as described in U.S. Pat. No. 6,241,961. A review on technologies for generating and applying novel radiolabed antibody conjugates that are useful in the present invention, is given by Goldenberg and Sharkey, 2007.

An antibody molecule of the invention, whether Fc-engineered or not, may also be bispecific, i.e. an antibody molecule that binds to two different targets, one of them being CD37, the other one being selected from e.g. surface antigens expressed by T cells, e.g. CD3, CD16 and CD56.

The present invention also relates to DNA molecules that encode the chimeric or humanized anti-CD37 antibody molecules of the invention. The sequences encoding variable heavy chains of the antibody molecules of the invention are shown in SEQ ID NO:1, SEQ ID NO:5, SEQ ID NO:7 and SEQ ID NO:9. The sequences encoding variable light chains of the antibody molecules of the invention are shown in SEQ ID NO:3, SEQ ID NO:11, SEQ ID NO:13, SEQ ID NO:15, SEQ ID NO:17, SEQ ID NO:19, SEQ ID NO: 21.

Nucleic acid molecules coding for the light chain and the heavy chain may be synthesized chemically and enzymatically (PCR amplification) by standard methods. First, suitable oligonucleotides can be synthesized with methods known in the art (e.g. Gait, 1984), which can be used to produce a synthetic gene. Methods to generate synthetic genes from oligonucleotides are known in the art (e.g. Stemmer et al., 1995; Ye et al., 1992; Hayden et Mandecki, 1988; Frank et al., 1987).

The DNA molecules of the invention include, but are not limited to, the DNA molecules shown in the sequence listing. Accordingly, the present invention also relates to nucleic acid molecules that hybridize to the DNA molecules set forth in the sequence listing under high stringency binding and washing conditions, as defined in WO 2007/042309, where such nucleic molecules encode an antibody or functional fragment thereof that has properties equivalent or superior to an antibody encoded by a sequence shown in the sequence listing. Preferred molecules (from an mRNA perspective) are those that have at least 75% or 80% (preferably at least 85%, more preferably at least 90% and most preferably at least 95%) homology or sequence identity with one of the DNA molecules described herein.

Yet another class of DNA variants that are within the scope of the invention may be defined with reference to the polypeptide they encode. These DNA molecules deviate with respect to their sequence from those depicted in the sequence listing, but encode, due to the degeneracy of the genetic code, antibodies with the identical amino acid sequences. By way of example, in view of expressing the antibodies in eukaryotic cells, the DNA sequences shown in the sequence listing have been designed to match codon usage in eukaryotic cells. If it is desired to express the antibodies in *E. coli*, these sequences can be changed to match *E. coli* codon usage. Variants of DNA molecules of the invention can be constructed in several different ways, as described e.g. in WO 2007/042309.

For producing the recombinant anti-CD37 antibody molecules of the invention, the DNA molecules encoding full-length light and heavy chains or fragments thereof are inserted into an expression vector such that the sequences are operatively linked to transcriptional and translational control sequences.

For manufacturing the antibodies of the invention, the skilled artisan may choose from a great variety of expression systems well known in the art, e.g. those reviewed by Kipriyanow and Le Gall, 2004.

Expression vectors include plasmids, retroviruses, cosmids, EBV-derived episomes, and the like. The expression vector and expression control sequences are selected to be compatible with the host cell. The antibody light chain gene and the antibody heavy chain gene can be inserted into separate vectors. In certain embodiments, both DNA sequences are inserted into the same expression vector. Convenient vectors are those that encode a functionally complete human CH or CL immunoglobulin sequence, with appropriate restriction sites engineered so that any VH or VL sequence can be easily inserted and expressed, as described above. The constant chain is usually kappa or lambda for the antibody light chain, for the antibody heavy chain, it can be, without limitation, any IgG isotype (IgG1, IgG2, IgG3, IgG4) or other immunoglobulins, including allelic variants.

The recombinant expression vector may also encode a signal peptide that facilitates secretion of the antibody chain from a host cell. The DNA encoding the antibody chain may be cloned into the vector such that the signal peptide is linked in-frame to the amino terminus of the mature antibody chain DNA. The signal peptide may be an immunoglobulin signal peptide or a heterologous peptide from a non-immunoglobulin protein. Alternatively, the DNA sequence encoding the antibody chain may already contain a signal peptide sequence.

In addition to the DNA sequences encoding the antibody chains, the recombinant expression vectors carry regulatory sequences including promoters, enhancers, termination and polyadenylation signals and other expression control elements that control the expression of the antibody chains in a host cell. Examples for promoter sequences (exemplified for expression in mammalian cells) are promoters and/or enhancers derived from (CMV) (such as the CMV Simian Virus 40 (SV40) (such as the SV40 promoter/enhancer), adenovirus, (e. g., the adenovirus major late promoter (Ad-MLP)), polyoma and strong mammalian promoters such as native immunoglobulin and actin promoters. Examples for polyadenylation signals are BGH polyA, SV40 late or early polyA; alternatively, 3'UTRs of immunoglobulin genes etc. can be used.

The recombinant expression vectors may also carry sequences that regulate replication of the vector in host cells (e. g. origins of replication) and selectable marker genes. Nucleic acid molecules encoding the heavy chain or an antigen-binding portion thereof and/or the light chain or an antigen-binding portion thereof of an anti-CD37 antibody, and vectors comprising these DNA molecules can be introduced into host cells, e.g. bacterial cells or higher eukaryotic cells, e.g. mammalian cells, according to transfection methods well known in the art, including liposome-mediated transfection, polycation-mediated transfection, protoplast fusion, microinjections, calcium phosphate precipitation, electroporation or transfer by viral vectors.

Preferably, the DNA molecules encoding the heavy chain and the light chain are present on two vectors which are co-transfected into the host cell, preferably a mammalian cell.

Mammalian cell lines available as hosts for expression are well known in the art and include, inter alia, Chinese hamster ovary (CHO, CHO-DG44) cells, NSO, SP2/0 cells, HeLa cells, baby hamster kidney (BHK) cells, monkey kidney cells (COS), human carcinoma cells (e. g., Hep G2), A549 cells, 3T3 cells or the derivatives/progenies of any such cell line. Other mammalian cells, including but not limited to human, mice, rat, monkey and rodent cells lines, or other eukaryotic cells, including but not limited to yeast, insect and plant cells, or prokaryotic cells such as bacteria may be used. The anti-CD37 antibody molecules of the invention are produced by culturing the host cells for a period of time sufficient to allow for expression of the antibody molecule in the host cells.

Antibody molecules are preferably recovered from the culture medium as a secreted polypeptide or it can be recovered from host cell lysates if for example expressed without a secretory signal. It is necessary to purify the antibody molecules using standard protein purification methods used for recombinant proteins and host cell proteins in a way that substantially homogenous preparations of the antibody are obtained. By way of example, state-of-the art purification methods useful for obtaining the anti-CD37 antibody molecule of the invention include, as a first step, removal of cells and/or particulate cell debris from the culture medium or lysate. The antibody is then purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin. As a final step in the process for obtaining an anti-CD37 antibody molecule preparation, the purified antibody molecule may be dried, e.g. lyophilized, as described below for therapeutic applications.

In a further aspect, the present invention relates to a pharmaceutical composition containing, as the active ingredient, the anti-CD37 antibody molecule of the invention.

To be used in therapy, the anti-CD37 antibody is included into pharmaceutical compositions appropriate to facilitate administration to animals or humans. Typical formulations of the anti-CD37 antibody molecule can be prepared by mixing the anti-CD37 antibody molecule with physiologically acceptable carriers, excipients or stabilizers, in the form of lyophilized or otherwise dried formulations or aqueous solutions or aqueous or non-aqueous suspensions. Carriers, excipients, modifiers or stabilizers are nontoxic at the dosages and concentrations employed. They include buffer systems such as phosphate, citrate, acetate and other anorganic or organic acids and their salts; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone or polyethylene glycol (PEG); amino acids such as glycine, glutamine, asparagine, histidine, arginine, or lysine; monosaccharides, disaccharides, oligosaccharides or polysaccharides and other carbohydrates including glucose, mannose, sucrose, trehalose, dextrins or dextrans; chelating agents such as EDTA; sugar alcohols such as, mannitol or sorbitol; salt-forming counter-ions such as sodium; metal complexes (e.g. Zn-protein complexes); and/or ionic or non-ionic surfactants such as TWEEN™ (polysorbates), PLURONICS™ or fatty acid esters, fatty acid ethers or sugar esters. Also organic solvents can be contained in the antibody formulation such as ethanol or isopropanol. The excipients may also have a release-modifying or absorption-modifying function.

The anti-CD37 antibody molecules may also be dried (freeze-dried, spray-dried, spray-freeze dried, dried by near or supercritical gases, vacuum dried, air-dried), precipitated or crystallized or entrapped in microcapsules that are prepared, for example, by coacervation techniques or by interfacial polymerization using, for example, hydroxymethylcellulose or gelatin and poly-(methylmethacylate), respectively, in colloidal drug delivery systems (for example, liposomes, albumin microspheres, microemulsions, nano-particles and nanocapsules), in macroemulsions or precipitated or immobilized onto carriers or surfaces, for example by pcmc technology (protein coated microcrystals). Such techniques are disclosed in Remington: The Science and Practice of Pharmacy, 21$^{st}$ edition, Hendrickson R. Ed.

Naturally, the formulations to be used for in vivo administration must be sterile; sterilization may be accomplished be conventional techniques, e.g. by filtration through sterile filtration membranes.

It may be useful to increase the concentration of the anti-CD37 antibody to come to a so-called high concentration liquid formulation (HCLF); various ways to generate such HCLFs have been described.

The anti-CD37 antibody molecule may also be contained in a sustained-release preparation. Such preparations include solid, semi-solid or liquid matrices of hydrophobic or hydrophilic polymers, and may be in the form of shaped articles, e.g. films, sticks or microcapsules and may be applied via an application device. Examples of sustained-release matrices include polyesters, hydrogels (for example, poly(2-hydroxyethyl-methacrylate) or sucrose acetate butyrate), or poly (vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilization (e.g. as described in WO 89/011297) from acidic solutions, controlling moisture content, using appropriate additives, and developing specific polymer matrix compositions.

Formulations that may also be used for the anti-CD37 antibody molecule of the invention are described in U.S. Pat. No. 7,060,268 and U.S. Pat. No. 6,991,790.

The CD37 antibody molecule can be incorporated also in other application forms, such as dispersions, suspensions or liposomes, tablets, capsules, powders, sprays, transdermal or intradermal patches or creams with or without permeation enhancing devices, wafers, nasal, buccal or pulmonary formulations, or may be produced by implanted cells or—after gene therapy—by the individual's own cells.

An anti-CD37 antibody molecule may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

The preferred mode of application is parenteral, by infusion or injection (intraveneous, intramuscular, subcutaneous, intraperitoneal, intradermal), but other modes of application such as by inhalation, transdermal, intranasal, buccal, oral, may also be applicable.

For the prevention or treatment of disease, the appropriate dosage of antibody will depend on the type of disease to be treated, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 0.01 µg/kg to 40 mg/kg (e.g. 0.1-20 mg/kg) of antibody is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays, e.g. by determining the extent of B cell depletion (e.g. using flow cytometry).

The "therapeutically effective amount" of the antibody to be administered is the minimum amount necessary to prevent, ameliorate, or treat a disease or disorder.

The anti-CD37 antibody molecule of the invention and pharmaceutical compositions containing it are useful to deplete B cells that express CD37 on their surface and that cause cancerous or autoimmune/inflammatory disease.

In a first aspect, the pharmaceutical composition of the invention is useful for the treatment of cancers, in particular any CD37-positive malignancies.

B cell malignancies include, without limitation, B cell lymphomas (e.g. various forms of Hodgkin's disease, B cell non-Hodgkin's lymphoma (NHL) and related lymphomas (e.g. Waldenström's macroglobulinaemia (also called lymphoplasmacytic lymphoma or immunocytoma) or central nervous system lymphomas), leukemias (e.g. acute lymphoblastic leukemia (ALL), chronic lymphocytic leukemia (CLL; also termed B cell chronic lymphocytic leukemia BCLL), hairy cell leukemia and chronic myoblastic leukemia) and myelomas (e.g. multiple myeloma). Additional B cell malignancies include small lymphocytic lymphoma, B cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B cell lymphoma of mucosa-associated (MALT) lymphoid tissue, nodal marginal zone B cell lymphoma, follicular lymphoma, mantle cell lymphoma, diffuse large B cell lymphoma, mediastinal (thymic) large B cell lymphoma, intravascular large B cell lymphoma, primary effusion lymphoma, Burkitt's lymphoma/leukemia, grey zone lymphoma, B cell proliferations of uncertain malignant potential, lymphomatoid granulomatosis, and post-transplant lymphoproliferative disorder.

In a further aspect, a pharmaceutical composition containing anti-CD37 antibodies is useful for the treatment of autoimmune and inflammatory diseases that involve B cells in their pathology.

Such diseases include, but are not limited to: arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, myasthenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic thrombocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, familial Mediterranean fever, microscopic polyangiitis, Cogan's syndrome, Whiskott-Aldrich syndrome and thromboangiitis obliterans (see WO 2007/014278).

Depending on the disorder to be treated, the anti-CD37 antibody molecule of the invention may be used on its own or in combination with one or more additional therapeutic agents, in particular selected from DNA damaging or tubulin binding agents or therapeutically active compounds that inhibit angiogenesis, signal transduction pathways or mitotic checkpoints in cancer cells.

The additional therapeutic agent may be administered simultaneously with, optionally as a component of the same pharmaceutical preparation, or before or after administration of the anti-CD37 antibody molecule.

In certain embodiments, the additional therapeutic agent may be, without limitation, one or more inhibitors selected from the group of inhibitors of EGFR family, VEGFR family, IGF-1R, Insulin receptors, AuroraA, AuroraB, PLK and PI3 kinase, FGFR, PDGFR, Raf, KSP or PDK1.

Further examples of additional therapeutic agents are inhibitors of CDKs, Akt, Src, Bcr-Abl, cKit, cMet/HGF, c-Myc, Flt3, HSP90, hedgehog antagonists, inhibitors of JAK/STAT, Mek, mTor, NFkappaB, the proteasome, Rho, an inhibitor of Wnt signaling or Notch signaling or an ubiquitination pathway inhibitor.

Examples for Aurora inhibitors are, without limitation, PHA-739358, AZD-1152, AT-9283, CYC-116, R-763, VX-667, MLN-8045, PF-3814735, SNS-314, VX-689, GSK-1070916, TTP-607, PHA-680626, MLN-8237 and ENMD-2076.

An example for a PLK inhibitor is GSK-461364.

Examples for raf inhibitors are BAY-73-4506 (also a VEGFR inhibitor), PLX-4032, RAF-265 (also a VEGFR inhibitor), sorafenib (also a VEGFR inhibitor), XL-281, and Nevavar (also an inhibitor of the VEGFR).

Examples for KSP inhibitors are ispinesib, ARRY-520, AZD-4877, CK-1122697, GSK-246053A, GSK-923295, MK-0731, SB-743921, LY-2523355, and EMD-534085.

Examples for a src and/or bcr-abl inhibitors are dasatinib, AZD-0530, bosutinib, XL-228 (also an IGF-1R inhibitor), nilotinib (also a PDGFR and cKit inhibitor), imatinib (also a cKit inhibitor), NS-187, KX2-391, AP-24534 (also an inhibitor of EGFR, FGFR, Tie2, Flt3), KM-80 and LS-104 (also an inhibitor of Flt3, Jak2).

An example for a PDK1 inhibitor is AR-12.

An example for a Rho inhibitor is BA-210.

Examples for PI3 kinase inhibitors are PX-866, PX-867, BEZ-235 (also an mTor inhibitor), XL-147, and XL-765 (also an mTor inhibitor), BGT-226, CDC-0941.

Examples for inhibitors of cMet or HGF are XL-184 (also an inhibitor of VEGFR, cKit, Flt3), PF-2341066, MK-2461, XL-880 (also an inhibitor of VEGFR), MGCD-265 (also an inhibitor of VEGFR, Ron, Tie2), SU-11274, PHA-665752, AMG-102, AV-299, ARQ-197, MetMAb, CGEN-241, BMS-777607, JNJ-38877605, PF-4217903, SGX-126, CEP-17940, AMG-458, INCB-028060, and E-7050.

An example for a c-Myc inhibitor is CX-3543.

Examples for Flt3 inhibitors are AC-220 (also an inhibitor of cKit and PDGFR), KW-2449, LS-104 (also an inhibitor of bcr-abl and Jak2), MC-2002, SB-1317, lestaurtinib (also an inhibitor of VEGFR, PDGFR, PKC), TG-101348 (also an inhibitor of JAK2), XL-999 (also an inhibitor of cKit, FGFR, PDGFR and VEGFR), sunitinib (also an inhibitor of PDGFR, VEGFR and cKit), and tandutinib (also an inhibitor of PDGFR, and cKit).

Examples for HSP90 inhibitors are, tanespimycin, alvespimycin, IPI-504, STA-9090, MEDI-561, AUY-922, CNF-2024, and SNX-5422.

Examples for JAK/STAT inhibitors are CYT-997 (also interacting with tubulin), TG-101348 (also an inhibitor of Flt3), and XL-019.

Examples for Mek inhibitors are ARRY-142886, AS-703026, PD-325901, AZD-8330, ARRY-704, RDEA-119, and XL-518.

Examples for mTor inhibitors are temsirolimus, deforolimus (which also acts as a VEGF inhibitor), everolimus (a VEGF inhibitor in addition). XL-765 (also a PI3 kinase inhibitor), and BEZ-235 (also a PI3 kinase inhibitor).

Examples for Akt inhibitors are perifosine, GSK-690693, RX-0201, and triciribine.

Examples for cKit inhibitors are masitinib, OSI-930 (also acts as a VEGFR inhibitor), AC-220 (also an inhibitor of Flt3 and PDGFR), tandutinib (also an inhibitor of Flt3 and PDGFR), axitinib (also an inhibitor of VEGFR and PDGFR), sunitinib (also an inhibitor of Flt3, PDGFR, VEGFR), and XL-820 (also acts as a VEGFR- and PDGFR inhibitor), imatinib (also a bcr-abl inhibitor), nilotinib (also an inhibitor of bcr-abl and PDGFR).

Examples for hedgehog antagonists are IPI-609, CUR-61414, GDC-0449, IPI-926, and XL-139.

Examples for CDK inhibitors are seliciclib, AT-7519, P-276, ZK-CDK (also inhibiting VEGFR2 and PDGFR), PD-332991, R-547, SNS-032, PHA-690509, PHA-848125, and SCH-727965.

Examples for proteasome inhibitors are bortezomib, carfilzomib, and NPI-0052 (also an inhibitor of NFkappaB).

Examples for proteasome inhibitors/NFkappaB pathway inhibitors are bortezomib, carfilzomib, NPI-0052, CEP-18770, MLN-2238, PR-047, PR-957, AVE-8680, and SPC-839.

An example for an inhibitor of the ubiquitination pathway is HBX-41108.

Examples for anti-angiogenic agents are inhibitors of the FGFR, PDGFR and VEGF(R), and thalidomides, such agents being selected from, without limitation, bevacizumab, motesanib, CDP-791, SU-14813, telatinib, KRN-951, ZK-CDK (also an inhibitor of CDK), ABT-869, BMS- 690514, RAF-265, IMC-KDR, IMC-18F1, IMiDs, thalidomide, CC-4047, lenalidomide, ENMD-0995, IMC-D11, Ki-23057, brivanib, cediranib, 1B3, CP-868596, IMC-3G3, R-1530 (also an inhibitor of Flt3), sunitinib (also an inhibitor of cKit and Flt3), axitinib (also an inhibitor of cKit), lestaurtinib (also an inhibitor of Flt3 and PKC), vatalanib, tandutinib (also an inhibitor of Flt3 and cKit), pazopanib, PF-337210, aflibercept, E-7080, CHIR-258, sorafenib tosylate (also an inhibitor of Raf), vandetanib, CP-547632, OSI-930, AEE-788 (also an inhibitor of EGFR and Her2), BAY-57-9352 (also an inhibitor of Raf), BAY-73-4506 (also an inhibitor of Raf), XL-880 (also an inhibitor of cMet), XL-647 (also an inhibitor of EGFR and EphB4), XL-820 (also an inhibitor of cKit), nilotinib (also an inhibitor of cKit and brc-abl), CYT-116, PTC-299, BMS-584622, CEP-11981, dovitinib, CY-2401401, and ENMD-2976.

The additional therapeutic agent may also be selected from EGFR inhibitors, it may be a small molecule EGFR inhibitor or an anti-EGFR antibody. Examples for anti-EGFR antibodies, without limitation, are cetuximab, panitumumab, nimotuzumab, zalutumumab; examples for small molecule EGFR inhibitors are gefitinib, erlotinib and vandetanib (also an inhibitor of the VEGFR). Another example for an EGFR modulator is the EGF fusion toxin.

Further EGFR and/or Her2 inhibitors useful for combination with an anti-CD37 antibody molecule of the invention are lapatinib, trastuzumab, pertuzumab, XL-647, neratinib, BMS-599626 ARRY-334543, AV-412, mAB-806, BMS-690514, JNJ-26483327, AEE-788 (also an inhibitor of VEGFR), AZD-8931, ARRY-380 ARRY-333786, IMC-11F8, Zemab, TAK-285, AZD-4769.

The additional drug may also be selected from agents that target the IGF-1R and insulin receptor pathways. Such agents include antibodies that bind to IGF-1R (e.g. CP-751871, AMG-479, IMC-A12, MK-0646, AVE-1642, R-1507, BIIB-022, SCH-717454, rhu Mab IGFR and novel chemical entities that target the kinase domain of the IGF1-R (e.g. OSI-906 or BMS-554417, XL-228, BMS-754807).

Other agents that may be advantageously combined in a therapy with the anti-CD37 antibody molecule of the invention are molecules targeting CD20, including CD20 specific antibodies like rituximab, LY-2469298, ocrelizumab, MEDI-552, IMMU-106, GA-101 (=R7159), XmAb-0367, ofatumumab, radiolabeled CD20 antibodies, like tositumumab and ibritumomab tiuxetan or other CD20 directed proteins, like the SMIP Tru015, PRO-131921, FBT-A05, veltuzumab, R-7159.

CD37 antibodies may be combined with inhibitors of other surface antigens expressed on leukocytes, in particular antibodies or antibody-like molecules, e.g. anti-CD2 (siplizumab), anti-CD4 (zanolimumab), anti-CD19 (MT-103, MDX-1342, SAR-3419, XmAb-5574), anti-CD22 (epratuzumab), anti-CD23 (lumiliximab), anti-CD30 (iratumumab), anti-CD32B (MGA-321), anti-CD38 (HuMax-CD38), anti-CD40 (SGN40), anti-CD52 (alemtuzumab), anti-CD80 (galiximab). An antibody of the invention may also be combined with another CD37 antagonist, e.g. TRU-016.

Other agents to be combined with CD37 antibodies are immunotoxins like BL-22 (an anti-CD22 immunotoxin), inotuzumab ozogamicin (an anti-CD23 antibody-calicheamicin conjugate), RFT5.dgA (anti-CD25 Ricin toxin A-chain), SGN-35 (an anti-CD30-auristatin E conjugate), and gemtuzumab ozogamicin (an anti-CD33 calicheamicin conjugate), MDX-1411 (anti-CD70 conjugate), or radiolabelled antibodies like $^{90}$Y-epratuzumab (anti-CD22 radioimmunoconjugate).

In addition, anti-CD37 antibodies may be combined with immunomodulators, agents, e.g. antibodies, that induce apoptosis or modify signal transduction pathways like the TRAIL receptor modulators mapatumumab (a TRAIL-1 receptor agonist), lexatumumab (a TRAIL-2 receptor agonist), tigatuzumab, Apomab, AMG-951 and AMG-655; an anti-HLA-DR antibody (like 1D09C3), an anti-CD74, an osteoclast differentiation factor ligand inhibitor (like denosumab), a BAFF antagonist (like AMG-623a) or an agonist of a Toll-like receptor (e.g. TLR-4 or TLR-9).

Other drugs that may be used in combination with the anti-CD37 antibody molecules of the present invention are selected from, but not limited to hormones, hormonal analogues and antihormonals (e.g. tamoxifen, toremifene, raloxifene, fulvestrant, megestrol acetate, flutamide, nilutamide, bicalutamide, cyproterone acetate, finasteride, buserelin acetate, fludrocortinsone, fluoxymesterone, medroxyprogesterone, hydroxyprogesterone caproate, diethylstilbestrol, testosterone propionate, fluoxymesterone/equivalents, octreotide, arzoxifene, pasireotide, vapreotide, adrenocorticosteroids/antagonists, prednisone, dexamethasone, ainoglutethimide), aromatase inhibitors (e.g. anastrozole, letrozole, liarozole, exemestane, atamestane, formestane), LHRH agonists and antagonists (e.g. goserelin acetate, leuprolide, abarelix, cetrorelix, deslorelin, histrelin, triptorelin), antimetabolites (e.g. antifolates like methotrexate, trimetrexate, pemetrexed, pyrimidine analogues like 5-fluorouracil, fluorodeoxyuridine, capecitabine, decitabine, nelarabine, 5-azacytidine, and gemcitabine, purine and adenosine analogues such as mercaptopurine, thioguanine, azathioprine, cladribine and pentostatin, cytarabine, fludarabine, clofarabine); antitumor antibiotics (e.g. anthracyclines like doxorubicin, daunorubicin, epirubicin and idarubicin, mitomycin-C, bleomycin dactinomycin, plicamycin, splicamycin, actimomycin D, mitoxantrone, mitoxantroneidarubicin, pixantrone, streptozocin, aphidicolin); platinum derivatives (e.g. cisplatin, oxaliplatin, carboplatin, lobaplatin, satraplatin); alkylating agents (e.g. estramustine, semustine, mechlorethamine, melphalan, chlorambucil, busulphan, dacarbazine, cyclophosphamide, ifosfamide, hydroxyurea, temozolomide, nitrosoureas such as carmustine and lomustine, thiotepa); antimitotic agents (e.g. vinca alkaloids like vinblastine, vindesine, vinorelbine, vinflunine and vincristine; and taxanes like paclitaxel, docetaxel and their formulations, larotaxel; simotaxel, and epothilones like ixabepilone, patupilone, ZK-EPO); topoisomerase inhibitors (e.g. epipodophyllotoxins like etoposide and etopophos, teniposide, amsacrine, topotecan, irinotecan, banoxantrone, camptothecin) and miscellaneous chemotherapeutics such as retinoic acid derivatives, amifostine, anagrelide, interferon alpha, interferon beta, interferon gamma, interleukin-2, procarbazine, N-methylhydrazine, mitotane, and porfimer, bexarotene, celecoxib, ethylenemine/methyl-melamine, thriethyienemelamine, triethylene thiophosphoramide, hexamethylmelamine, and enzymes L-asparaginase, L-arginase and metronidazole, misonidazole, desmethylmisonidazole, pimonidazole, etanidazole, nimorazole, RSU 1069, EO9, RB 6145, SR4233, nicotinamide, 5-bromodeozyuridine, 5-iododeoxyuridine, bromodeoxycytidine, erythrohydroxynonyl-adenine, anthracenedione, GRN-163L (a competitive telomerase template antagonist), SDX-101 (a PPAR agonist), talabostat (a DPP inhibitor), forodesine (a PNP inhibitor), atacicept (a soluble receptor targeting TNF family members BLyS and APRIL), TNF-alpha neutralizing agents (Enbrel, Humira, Remicade), XL-844 (a CHK1/2 inhibitor), VNP-40101M (a DNA alkylating agent), SPC-2996 (an antisense bcl2 inhibitor), obatoclax (a bcl2 inhibitor), enzastaurin (a PKC beta modulator), vorinistat (an HDAC inhibitor), romidepsin (an HDAC inhibitor), AT-101 (a Bcl-2/Bcl-xL inhibitor), plitidepsin (a multi-actioned depsipeptide), SL-11047 (a polyamine metabolism modulators).

In certain embodiments, the anti-CD37 antibody molecule is applied together with "CHOP" (a combination of cyclophosphamide, doxorubicin, vincristine and prednisone).

The anti-CD37 antibody molecule of the invention may also be used in combination with other therapies including surgery, radiotherapy, endocrine therapy, biologic response modifiers, hyperthermia and cryotherapy and agents to attenuate any adverse effect (e.g. antiemetics), G-CSF, GM-CSF, photosensitizers such as hematoporphyrin derivatives, Photofrin®, benzoporphyrin derivatives, Npe6, tin etioporphyrin, pheoboride-a bacteriochlorophyll-a, naphthalocyanines, phthalocyanines, zinc phthalocyanines.

Monoclonal antibodies show exquisite antigen specificity and frequently only react with the human target antigen, but not with homologue proteins from animal species. To support development of therapeutic antibodies, appropriate animal models for assessment of in vivo toxicity and pharmacodynamic behavior are desirable. One possibility for an in vivo model is a transgenic mouse in which the endogenous target antigen is replaced by its human homologue ("knockout/knock-in mouse"). In particular, for developing therapeutic anti-CD37 antibodies, the murine CD37 gene can be replaced by the human CD37 gene. This can be achieved by constructing a targeting vector which contains the coding genomic sequence of the human CD37 gene flanked by non-translated sequences. This targeting vector can be used for homologous recombination using mouse ES cells. Transgenic animals homozygous for human CD37 expression can be used to assess the pharmacodynamic effect of antibodies directed against human CD37, e.g. by monitoring the number of peripheral B cells after application of the antibodies. Alternatively, those mice can be used to investigate potential toxic effects of human CD37 specific antibodies, after i.v. application.

Another possibility in the case of lack of animal cross-reactivity of monoclonal antibodies is the generation of a so-called surrogate antibody. A surrogate antibody is an antibody which reacts with the homologous protein of an animal species which is relevant and useful for investigation of pharmacodynamic and toxic effects, e.g. the mouse or the cynomolgus monkey. In case of CD37, monoclonal antibodies are developed which are specific for macaque CD37 or mouse CD37, respectively Ideally, such a surrogate antibody should have similar binding and functional properties as the development antibody. This can be investigated by the use of assay systems which utilize macaque or mouse CD37 expressing cells as target cells, e.g. for binding, FACS Scatchard analysis, ADCC and apoptosis assays. Ultimately, the surrogate antibody can be selected by virtue of its B cell depleting activity in macaque or mouse blood in vitro.

EXAMPLE 1

Figure 1:
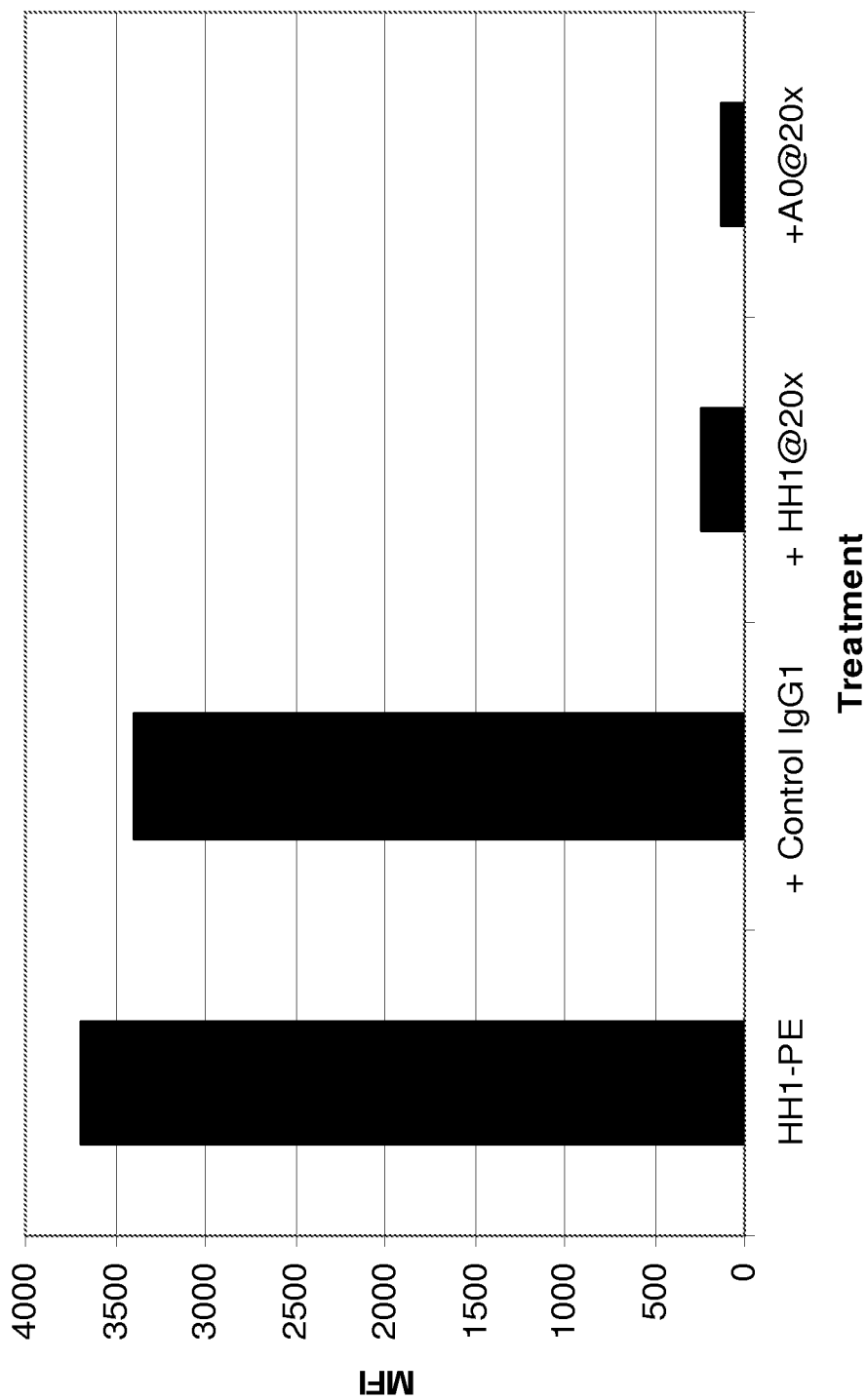
FIG. 1: Chimeric Antibody A0 specifically recognizes the CD37 antigen, determined by FACS competition assay

Generation of Chimeric and Humanized Anti-CD37 Antibodies a) Generation of Chimeric Antibody A0

Based on the variable heavy and light chain amino acid sequences shown in SEQ ID NO:2 and SEQ ID NO:4, the corresponding DNA sequences are synthesized applying codon usage optimized for mammalian cells (GeneArt, Regensburg, Germany), adding at the 5' end a HindIII and at the 3' end a BamH1 cloning site. The synthesized DNA molecules are digested with HindIII and BamHI and the resulting DNA fragments (SEQ ID NO:1 and SEQ ID NO:3 plus restriction sites) are cloned into pcDNA3.1 based expression vectors coding for human IgG1 constant region and human kappa light chain constant region, respectively (SEQ ID NO:24 and SEQ ID NO:26). EndoFree plasmid preparations (Qiagen) are prepared and the heavy and light chain plasmids are co-transfected into HEK293 freestyle cells (Invitrogen) at a concentration of 1 mg/L of each plasmid according to the supplier's protocol. After 72 hours the supernatant is harvested and the IgG concentration is determined by ELISA. The resulting chimeric anti-CD37 antibody (designated A0) is purified on a modified protein A column (GE Healthcare), eluted into a citrate buffer then dialyzed in PBS.

b) Generation of Humanized Versions of Chimeric Antibody A0

Humanization of chimeric mAb A0, as obtained in a), is performed using a CDR grafting approach, as described e.g. in U.S. Pat. No. 5,225,539; U.S. Pat. No. 6,548,640; U.S. Pat. No. 6,982,321.

To establish a structural model of the mAb A0 VL domain, a structural template is chosen from the Protein Data Bank (PDB) of Brookhaven National Laboratory. The VL domain from the murine monoclonal antibody entry "1KB5" is chosen with 88% sequence identity/81% similarity and 2.5 Å resolution. For the mAb A0 VH domain, the same mouse monoclonal antibody structure "1KB5" with 90% sequence identity and 91% similarity is chosen as the main modeling template. The best fit for human consensus framework is found to be of the type human Vkappa1 (hVK1) and human VH1 (hVH1). As an alternative design, a graft to the most stable human consensus domains hVK3 and hVH3 is chosen. For grafting, the mAb A0_VL and mAb A0_VH models are combined with human consensus domain models hVK1, hVK3, hVH1A and hVH3 and combined to produce to Fv-models. Loop grafting is performed by embedding the murine mAb A0 CDR regions into the human antibody frameworks and the DNA molecules of the humanized chain constructs are synthesized.

The respective humanized variable regions are synthesized and cloned into immunoglobulin expression vectors and transiently expressed in the HEK 293 freestyle expression system (Invitrogen), as described in a), in the combinations of heavy and light chain sequences as shown in Table 1, and purified on protein A columns.

TABLE 1

Sequences of heavy and light variable chains of the chimeric and humanized anti-CD37 antibodies used in the Examples.

| Antibody | Heavy Chain SEQ ID NO: aa/DNA | Light Chain SEQ ID NO: aa/DNA |
|---|---|---|
| A (=A0) | seq 2/1 | seq 4/3 |
| B | seq 6/5 | seq 12/11 |
| C | seq 6/5 | seq 14/13 |

TABLE 1-continued

Sequences of heavy and light variable chains of the chimeric and humanized anti-CD37 antibodies used in the Examples.

| Antibody | Heavy Chain SEQ ID NO: aa/DNA | Light Chain SEQ ID NO: aa/DNA |
|---|---|---|
| D | seq 6/5 | seq 16/15 |
| H | seq 8/7 | seq 18/17 |
| I | seq 8/7 | seq 20/19 |
| J | seq 8/7 | seq 22/21 |
| K | seq 10/9 | seq 18/17 |
| L | seq 10/9 | seq 20/19 |
| M | seq 10/9 | seq 22/21 | c) Generation of Fc-Engineered Chimeric and Humanized Anti-CD37 Antibodies

The generation of Fc mutants is performed as described by Lazar et al., 2006. The resulting Fc-engineered heavy chain sequence is introduced into the expression vector pAD-CMV1 (described in EP 393 438) and co-transfected together with a plasmid containing the light chain encoding sequence into CHO-DG44 cells. The antibody is harvested from cell culture media 5 to 7 days after transfection and purified via protein A chromatography, eluted into a citrate buffer then dialyzed in PBS. The protein content of the samples is determined via Protein A HPLC, the endotoxin content is determined via Kinetic-QCL Kinetic Chromogenic Assay (Lonza). The monomer content of the samples is determined by HP-SEC, all samples used for functional testing show a monomer content of >95%.

TABLE 2

Sequences of heavy and light variable chains (columns III and IV) and Fc mutations (coulum II) of the chimeric and humanized anti-CD37 antibodies (antibody A0, B0, C0 etc. is identical with antibody A and B, C etc. in Table 1).

| I Ab | II Fc substitution(s) (Kabat numbering) | III SEQ ID NO: v heavy chain aa/DNA | IV SEQ ID NO: v light chain aa/DNA | V SEQ ID NO: complete heavy chain aa/DNA | VI SEQ ID NO: complete light chain aa/DNA |
|---|---|---|---|---|---|
| A0 | — | seq 2/1 | seq 4/3 | 2/1 fused to 24/23 | 4/3 fused to 26/25 |
| A1 | I332E | seq 2/1 | seq 4/3 | 2/1 fused to 24*/23* | 4/3 fused to 26/25 |
| A2 | S239D/I332E | seq 2/1 | seq 4/3 | 28/27 | 30/29 |
| A3 | I332E/G236A | seq 2/1 | seq 4/3 | 2/1 fused to 24*/23* | 4/3 fused to 26/25 |
| A4 | S239D/I332E/G236A | seq 2/1 | seq 4/3 | 32/31 | 34/33 |
| B0 | — | seq 6/5 | seq 12/11 | 6/5 fused to 24/23 | 12/11 fused to 26/25 |
| B1 | I332E | seq 6/5 | seq 12/11 | 6/5 fused to 24*/23* | 12/11 fused to 26/25 |
| B2 | S239D/I332E | seq 6/5 | seq 12/11 | 36/35 | 38/37 |
| B3 | I332E/G236A | seq 6/5 | seq 12/11 | 6/5 fused to 24*/23* | 12/11 fused to 26/25 |
| B4 | S239D/I332E/G236A | seq 6/5 | seq 12/11 | 40/39 | 42/41 |
| C0 | — | seq 6/5 | seq 14/13 | 6/5 fused to 24/23 | 14/13 fused to 26/25 |
| C1 | I332E | seq 6/5 | seq 14/13 | 6/5 fused to 24*/23* | 14/13 fused to 26/25 |
| C2 | S239D/I332E | seq 6/5 | seq 14/13 | 6/5 fused to 24*/23* | 14/13 fused to 26/25 |
| C3 | I332E/G236A | seq 6/5 | seq 14/13 | 6/5 fused to 24*/23* | 14/13 fused to 26/25 |
| C4 | S239D/I332E/G236A | seq 6/5 | seq 14/13 | 6/5 fused to 24*/23* | 14/13 fused to 26/25 |
| D0 | — | seq 6/5 | seq 16/15 | 6/5 fused to 24/23 | 16/15 fused to 26/25 |
| D1 | I332E | seq 6/5 | seq 16/15 | 6/5 fused to 24*/23* | 16/15 fused to 26/25 |
| D2 | S239D/I332E | seq 6/5 | seq 16/15 | 6/5 fused to 24*/23* | 16/15 fused to 26/25 |

TABLE 2-continued

Sequences of heavy and light variable chains (columns III and IV) and Fc mutations (coulum II) of the chimeric and humanized anti-CD37 antibodies (antibody A0, B0, C0 etc. is identical with antibody A and B, C etc. in Table 1).

| I Ab | II Fc substitution(s) (Kabat numbering) | III SEQ ID NO: v heavy chain aa/DNA | IV SEQ ID NO: v light chain aa/DNA | V SEQ ID NO: complete heavy chain aa/DNA | VI SEQ ID NO: complete light chain aa/DNA |
|---|---|---|---|---|---|
| D3 | I332E/G236A | seq 6/5 | seq 16/15 | 6/5 fused to 24/*23* | 16/15 fused to 26/25 |
| D4 | S239D/I332E/G236A | seq 6/5 | seq 16/15 | 6/5 fused to 24/*23* | 16/15 fused to 26/25 |
| H0 | — | seq 8/7 | seq 18/17 | 8/7 fused to 24/23 | 18/17 fused to 26/25 |
| H1 | I332E | seq 8/7 | seq 18/17 | 8/7 fused to 24*/23* | 18/17 fused to 26/25 |
| H2 | S239D/I332E | seq 8/7 | seq 18/17 | 8/7 fused to 24*/23* | 18/17 fused to 26/25 |
| H3 | I332E/G236A | seq 8/7 | seq 18/17 | 8/7 fused to 24*/23* | 18/17 fused to 26/25 |
| H4 | S239D/I332E/G236A | seq 8/7 | seq 18/17 | 8/7 fused to 24*/23* | 18/17 fused to 26/25 |
| I-0 | — | seq 8/7 | seq 20/19 | 8/7 fused to 24/23 | 20/19 fused to 26/25 |
| I-1 | I332E | seq 8/7 | seq 20/19 | 8/7 fused to 24*/23* | 20/19 fused to 26/25 |
| I-2 | S239D/I332E | seq 8/7 | seq 20/19 | 8/7 fused to 24*/23* | 20/19 fused to 26/25 |
| I-3 | I332E/G236A | seq 8/7 | seq 20/19 | 8/7 fused to 24*/23* | 20/19 fused to 26/25 |
| I-4 | S239D/I332E/G236A | seq 8/7 | seq 20/19 | 8/7 fused to 24*/23* | 20/19 fused to 26/25 |
| J0 | — | seq 8/7 | seq 22/21 | 8/7 fused to 24/23 | 22/21 fused to 26/25 |
| J1 | I332E | seq 8/7 | seq 22/21 | 8/7 fused to 24*/23* | 22/21 fused to 26/25 |
| J2 | S239D/I332E | seq 8/7 | seq 22/21 | 8/7 fused to 24*/23* | 22/21 fused to 26/25 |
| J3 | I332E/G236A | seq 8/7 | seq 22/21 | 8/7 fused to 24*/23* | 22/21 fused to 26/25 |
| J4 | S239D/I332E/G236A | seq 8/7 | seq 22/21 | 8/7 fused to 24*/23* | 22/21 fused to 26/25 |
| K0 | — | seq 10/9 | seq 18/17 | 10/9 fused to 24/23 | 18/17 fused to 26/25 |
| K1 | I332E | seq 10/9 | seq 18/17 | 10/9 fused to 24*/23* | 18/17 fused to 26/25 |
| K2 | S239D/I332E | seq 10/9 | seq 18/17 | 10/9 fused to 24*/23* | 18/17 fused to 26/25 |
| K3 | I332E/G236A | seq 10/9 | seq 18/17 | 10/9 fused to 24*/23* | 18/17 fused to 26/25 |
| K4 | S239D/I332E/G236A | seq 10/9 | seq 18/17 | 10/9 fused to 24*/23* | 18/17 fused to 26/25 |
| L0 | — | seq 10/9 | seq 20/19 | 10/9 fused to 24/23 | 20/19 fused to 26/25 |
| L1 | I332E | seq 10/9 | seq 20/19 | 10/9 fused to 24*/23* | 20/19 fused to 26/25 |
| L2 | S239D/I332E | seq 10/9 | seq 20/19 | 10/9 fused to 24*/23* | 20/19 fused to 26/25 |
| L3 | I332E/G236A | seq 10/9 | seq 20/19 | 10/9 fused to 24*/23* | 20/19 fused to 26/25 |
| L4 | S239D/I332E/G236A | seq 10/9 | seq 20/19 | 10/9 fused to 24*/23* | 20/19 fused to 26/25 |
| M0 | — | seq 10/9 | seq 22/21 | 10/9 fused to 24/23 | 22/21 fused to 26/25 |
| M1 | I332E | seq 10/9 | seq 22/21 | 10/9 fused to 24*/23* | 22/21 fused to 26/25 |
| M2 | S239D/I332E | seq 10/9 | seq 22/21 | 10/9 fused to 24*/23* | 22/21 fused to 26/25 |
| M3 | I332E/G236A | seq 10/9 | seq 22/21 | 10/9 fused to 24*/23* | 22/21 fused to 26/25 |
| M4 | S239D/I332E/G236A | seq 10/9 | seq 22/21 | 10/9 fused to 24*/23* | 22/21 fused to 26/25 |

Full-length sequences of heavy and light chains are listed in colums V and VI. (The sequences in column V marked with * refer to the IgG1 sequence of SEQ ID NOs 24 and 23 (wild-type sequences) that have been modified to have the substitution(s) corresponding to column II, and the respective mutation(s) in the coding DNA).

EXAMPLE 2

Chimeric mAb A0 Specifically Recognizes the CD37 Antigen

The specificity of MAb A0 for cellular CD37 is tested in a FACS competition assay on Ramos Burkitt lymphoma cells (ATCC #CRL-1596). Cells are grown in tissue culture flasks (175 cm$^2$) using RPMI-1640+GlutaMAX supplemented with 10% heat-inactivated fetal bovine serum, 12.5 mM HEPES, 1 mM sodium pyruvat, 1% MEM non-essential amino acids as culture medium. Cells are cultivated with an initial density of 3×10$^5$ cells/ml at 37° C. and 5% $CO_2$ in a humidified atmosphere for three days. The cultures are maintained at a cell concentration between 3×10$^5$ and 1.8×10$^6$/ml by sub-cultivation in a ratio of 1:6 with fresh culture medium 2-3 times a week. For FACS competition analysis, the CD37-specific mAb HH1 (Santa Cruz) directly labeled with phycoerythrin (PE) is used at a concentration of 1 µg/ml. The antibody is preincubated with the unlabelled competitor antibody A0 for 10 min at 4° C. at the indicated molar ratio. Thereafter, 1×10$^5$ Ramos cells are incubated for 30 min with the antibody mixture on ice. Thereafter, cells are washed twice in phosphate buffered saline (PBS), resuspended in FACS buffer and measured on a BD FACS Canto. Results of such an assay are shown in FIG. 1. Addition of a control human IgG1 antibody (Sigma IgG1 kappa) at 20-fold molar excess does not significantly reduce the mean fluorescence intensity (MFI) of Ramos cells. Addition of either unlabelled HH1 antibody or A0 antibody at 20-fold molar excess almost completely abrogated binding of the directly labeled HH1 antibody. This indicates that A0 and HH1 antibodies recognize identical or similar epitopes on Ramos cells and compete for binding to cellular CD37 antigen.

EXAMPLE 3

Binding of Humanized Versions of mAb A0 to Cellular CD37 Antigen

Figure 2:
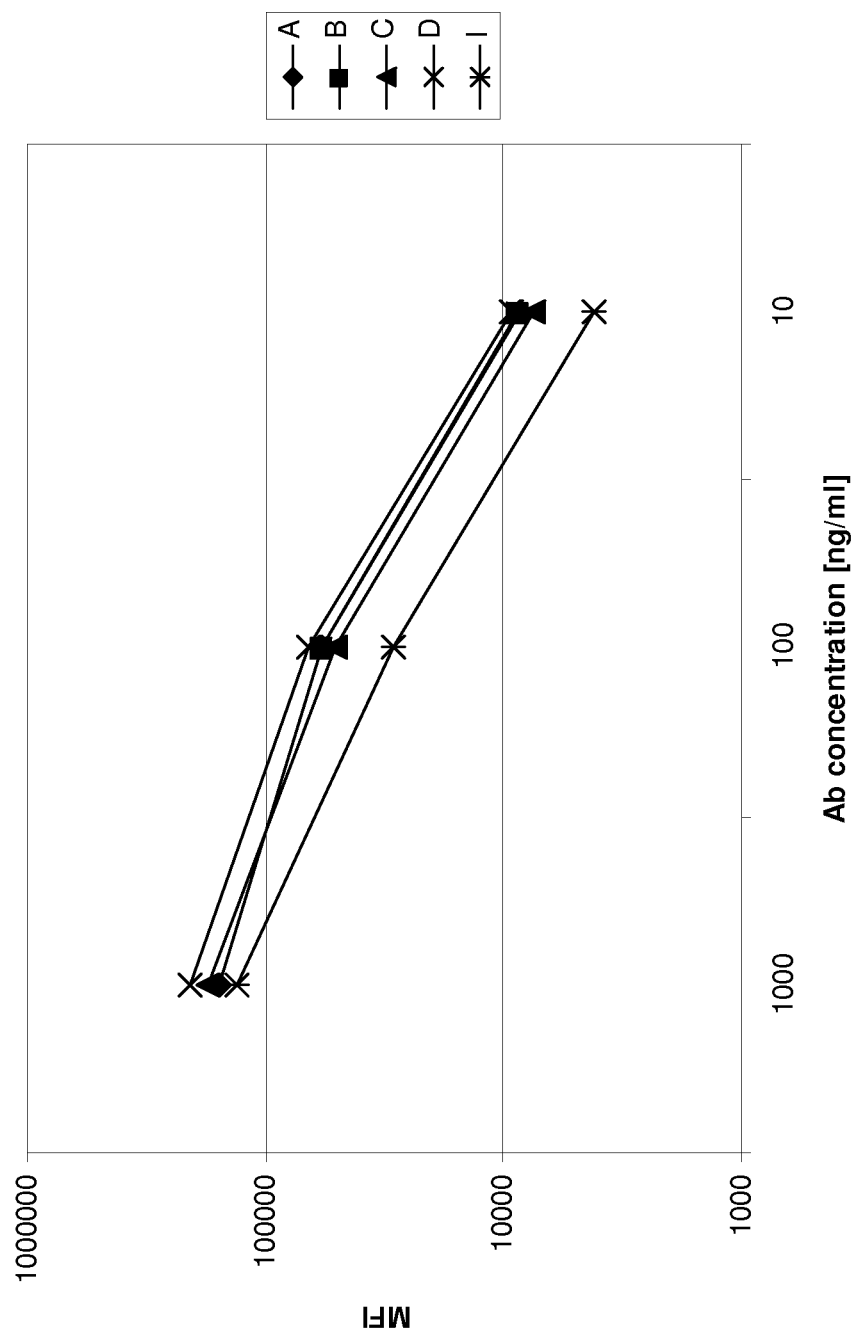
FIG. 2: Binding of humanized versions of A0 to cellular CD37 antigen, determined by FACS
Figure 3:
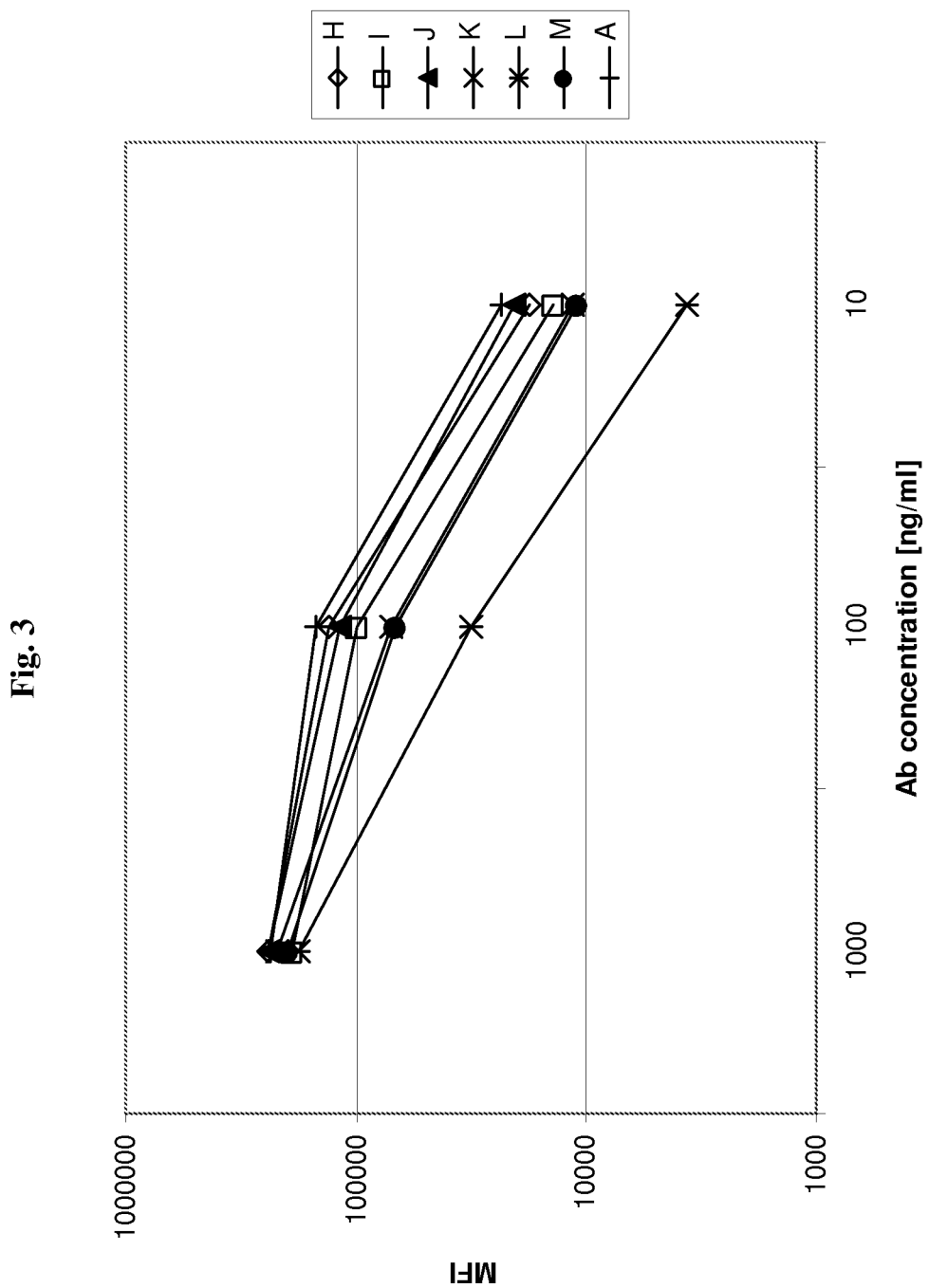
FIG. 3: Binding of humanized versions of A0 to cellular CD37 antigen, determined by FACS

Humanized versions of A0 are tested for their binding to cellular CD37 antigen by FACS analysis. Antibodies are added to Ramos cells at the indicated concentrations and allowed for binding for 30 min at 4° C. Thereafter, bound antibody is detected with PE-labelled goat-anti-human IgG antibody (Sigma), cells are washed twice with PBS, and thereafter cells are resuspended in FACS buffer and analyzed by FACS on a BD FACS Canto. Examples are shown in FIGS. 2 and 3 (antibodies A, B, C, D, I or A, H, I, J, K, L and M, respectively; see Table 1). Several of the humanized versions of A0 show similar binding to Ramos cells as the parental antibody A0, indicating that humanization does not reduce binding to cellular CD37 antigen.

EXAMPLE 4

FACS Scatchard Analysis of Humanized Versions of Chimeric mAb A0

Figure 4:
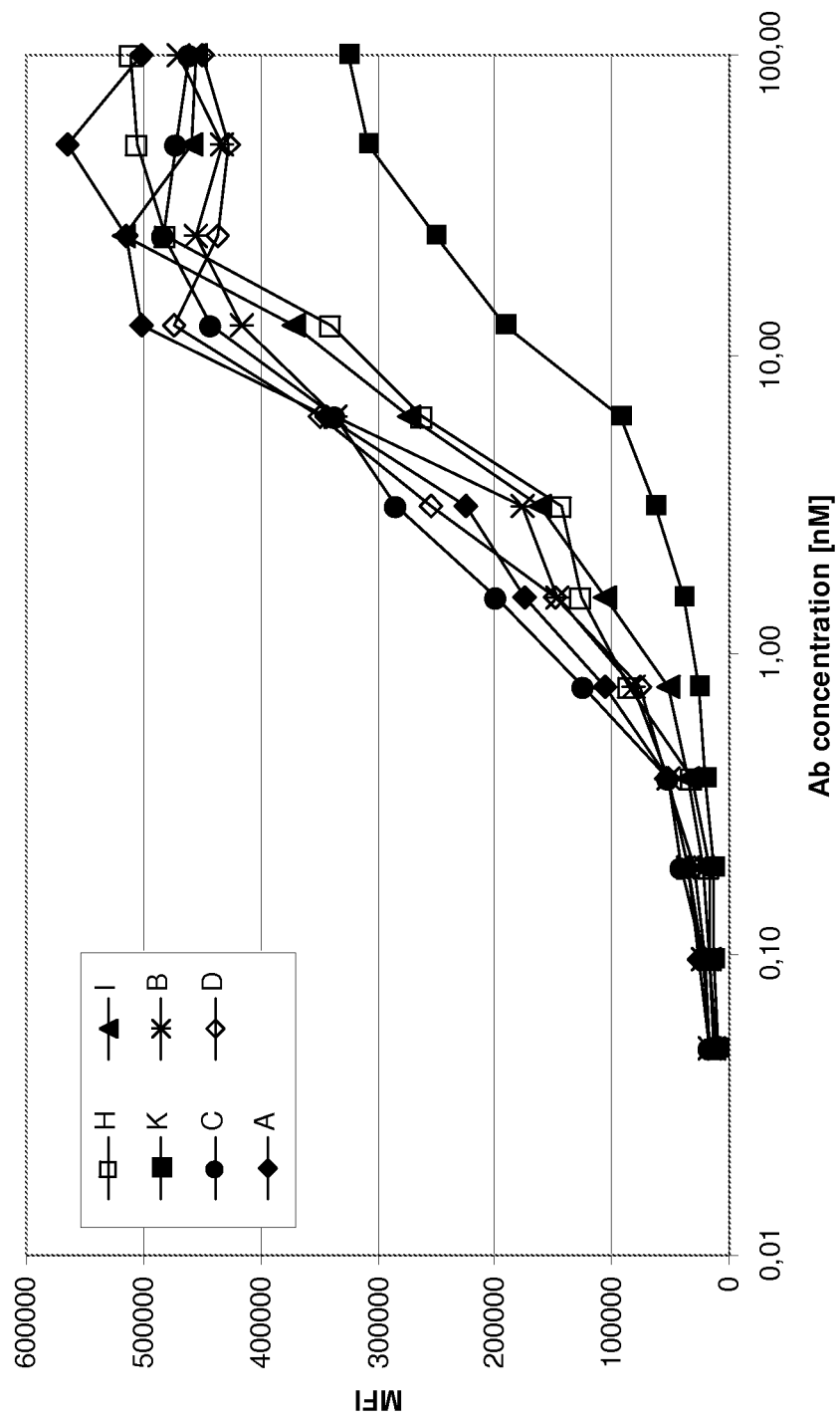
FIG. 4: Affinity of humanized versions of A0 to cellular CD37 antigen, determined by FACS scatchard analysis

The affinity of humanized versions of antibody A0 (designated B, C, D, H, I and K; see Table 1) to cellular CD37 antigen is determined by FACS scatchard analysis as described elsewhere (Brockhoff et al., 1994). Briefly, antibody dilutions are prepared in a 96 well plate starting with 100-400 nM in the first well (80 µl), followed by 11 dilution steps (1:2, 40+40 µl). 50 µl of mAb dilutions are added to FACS tubes, 150 µl cells (0.8×10$^6$/ml=1.2×10$^5$ cells/tube) are added to each FACS tube. Cells are gently mixed and incubated for 1 h on ice. Thereafter 50 µl FITC conjugated secondary antibody (conc. 15 µg/ml; mouse mAb anti-hu IgG all subclasses, Zymed 05-4211) is added, mixed, and incubated for 30 min on ice. 4 ml PBS ph7.2 containing 0.02% acid are added thereafter, cells are pelleted and resuspended in 300 µl PBS pH 7.2 and subjected to FACS analysis using a BD FACS Canto. All experimental steps are performed on wet ice, all antibody dilutions are made in PBS/0.5% BSA+0.02% acid. FACS calibration is performed using Quantum FITC MESF (Premix) High Level Beads (Bangs Laboratories). All samples are measured using the same FACS parameters. The ratio of bound IgG versus free IgG is calculated from MFI values at different antibody concentrations and displayed as scatchard blot. FIG. 4 shows the MFI/antibody concentration relationship of several humanized variants of A0. The results show similar binding to Ramos cells of some of the humanized versions as the starting antibody, with dissociation constants ($K_d$) ranging from 2.15 to 4.90 nanomoles/liter.

EXAMPLE 5

ADCC Activity of Humanized Versions of the Chimeric mAb A0

The ability of humanized versions of A0 (designated B, C, D, H, J, K; see Table 1) to mediate antibody-dependent cell-mediated cytotoxicity (ADCC) is assessed using Ramos cells as target cells and IL2-stimulated human PBMCs as effector cells. Ramos cells (Burkitt's lymphoma; ATCC #CRL-1596) were purchased from ATCC. Cells are grown in tissue culture flasks (175 cm$^2$) using RPMI-1640+GlutaMAX supplemented with 10% heat-inactivated fetal bovine serum, 12.5 mM HEPES, 1 mM sodium pyruvat, 1% MEM non-essential amino acids as culture medium. Cells are cultivated with an initial density of 3×10$^5$ cells/ml at 37° C. and 5% $CO_2$ in a humidified atmosphere for three days. The cultures are maintained at a cell concentration between 3×10$^5$ and 1.8×10$^6$/ml by sub-cultivation in a ratio of 1:6 with fresh culture medium 2-3 times a week. An aliquot of the cell culture at a cell density between 1.5×10$^6$/ml and 1.8×10$^6$/ml and growing in the log-phase is centrifuged (200×g, i.e. 1000 rpm) for 10 min. Cells are washed once with washing medium (RPMI 1640 w/o L-glutamine) and pelleted (200×g, i.e. 1000 rpm; 10 min) Cell pellet is resuspended in assay medium [1% BSA in RPMI w/o L-glutamine] and cell count is determined. Cell concentration is adjusted to 2×10$^5$/ml.

Approximately 50-80 ml whole blood drawn from healthy donors is used for the isolation of PBMC. 10 ml whole blood are diluted 1:3.6 with 26 ml HBSS (Hanks' Balanced Salt Solution w/o calcium and magnesium) in a 50 ml tube. 18 ml diluted whole blood is layered on top of 12 ml Lymphoprep (Nycomed Pharma) in a 50 ml tube and centrifuged at 370×g (1400 rpm) for 35 min. The mononuclear cells from the interface are aspirated and washed first with HBSS (750×g, i.e. 1900 rpm; 10 min), then a second time with HBSS (300×g, i.e. 1200 rpm; 10 min) and at last with HBSS (160×g, i.e. 900 rpm; 10 min) The pelleted cells are gently resuspended in culture medium/assay medium (10% heat-inactivated human AB serum in RPMI 1640 w/o L-glutamine) using a pipette and the cell count is determined in the cell counter. The PBMC concentration is adjusted to 1×10$^7$/ml. The freshly isolated PBMC (5×10$^5$/ml) are maintained in culture medium (RPMI 1640 w/o L-glutamine supplemented with 10% human AB serum) in a tissue culture flask (75 cm$^2$) at 37° C. in CO$_2$ incubator over night. On the following day cells are stimulated with hIL-2 at a final concentration of 1 U/ml for 3 further days. IL-2 stimulated PBMC are separated from cell debris on a Lymphoprep gradient. The purified IL-2 stimulated PBMC are suspended in culture medium/assay medium at a concentration of 1×10$^7$/ml.

The co-cultivation of effector cells with target cells in presence of specific or unspecific antibody is performed in duplicates or triplicates in 96-well round-bottom microtiter plates in a final volume of 200 µl assay medium per well consisting of 10% human AB serum and 1% BSA in RPMI in 1:1 ratio. First effector cells (freshly isolated PBMC cells in 100 µl 10% human AB serum in RPMI per well) are plated, followed by target cells and antibody solution diluted in 50 µl 1% BSA in RPMI. As a control, effector cells are cultivated in assay medium alone (effector cell control) and target cells are cultivated either in assay medium alone (spontaneous lysis) or in assay medium supplemented with 1% Triton X-100 (maximal lysis). The co-culture is incubated at 37° C. in a humid CO$_2$ incubator for 3 hours. At the end of the incubation cells are removed from the culture medium by centrifugation (200×g, i.e. 1000 rpm; 10 min) at room temperature. Cell free supernatants (100 µl/well) are transferred into corresponding wells of a 96-well flat-bottom plate. To determine the LDH activity in these supernatants 100 µl reaction mixture (freshly mixed 250 µl catalyst with 11.25 ml dye solution) are added to each well and incubated 30 min at room temperature in the dark. Then the absorbance is measured as described below.

Cytotoxicity Detection Kit (LDH; Roche) is used to measure ADCC activity. The detection of cytotoxicity is based on the measurement of LDH enzyme activity released from plasma membrane-damaged cells. LDH released into the culture supernatants reduces the tetrazolium salt from the kit to formazan. The absorption maximum of formazan dye is measured at 490 nm against a reference wavelength of 650 nm in an ELISA plate reader. To calculate percent cell mediated cytotoxicity five controls are performed in each experimental setup.

Background control I (1): LDH activity contained in the assay medium, which is subtracted from values (3) and (5).
Background control II (2): LDH activity contained in 1% Triton-X100 in assay medium, which is subtracted from maximal LDH release values (4).
Spontaneous LDH release (3): LDH activity released from target cells alone.
Maximal LDH release (4): Maximum releasable LDH activity in the target cells.
Effector cell control (5): LDH activity released from effector cells only.

Figure 5:
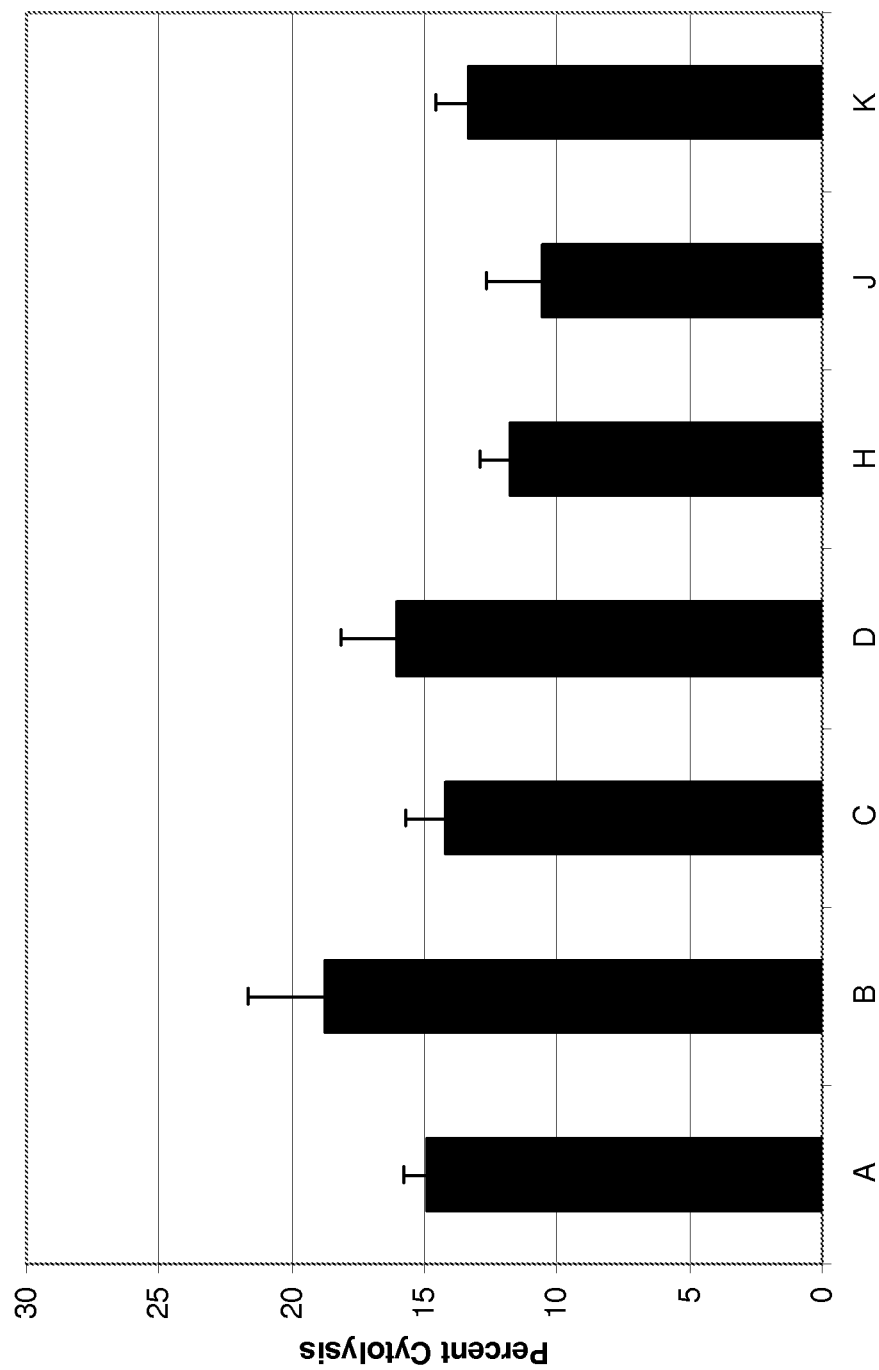
FIG. 5: ADCC activity of humanized versions of A0 on Ramos cells

To determine the percentage cell mediated cytotoxicity, the average absorbance of the triplicates or duplicates is calculated and the background is subtracted according to the manufacturer's instructions. In FIG. 5, the results from an ADCC assay using an E:T ratio of 25:1 and Ramos target cells are shown. Antibodies are added in a concentration of 30 ng/ml. Both the starting mAb and humanized versions thereof display similar ADCC activity against the Ramos cells. In conclusion, humanization of anti-CD37 mAb A does not significantly alter its ADCC inducing capacity.

EXAMPLE 6

Pro-Apoptotic Activity of Humanized Versions of the Chimeric mAb A0

The pro-apoptotic activity of mAb A0 (=A) and humanized versions thereof (B, C, D and I; see Table 1) is assessed by measurement of AnnexinV/PI positive cells after incubation of Ramos cells with mAbs. Ramos cells (Burkitt's lymphoma; ATCC #CRL-1596) are received from ATCC. Cells are grown in tissue culture flasks (175 cm$^2$) using RPMI-1640+GlutaMAX supplemented with 10% heat-inactivated fetal bovine serum, 12.5 mM HEPES, 1 mM sodium pyruvat, 1% MEM non-essential amino acids as culture medium. Cells are cultivated with an initial density of 3×10$^5$ cells/ml at 37° C. and 5% CO$_2$ in a humidified atmosphere for three days. The cultures are maintained at a cell concentration between 3×10$^5$ and 1.8×10$^6$/ml by sub-cultivation in a ratio of 1:6 with fresh culture medium 2-3 times a week. An aliquot of the cell culture at a cell density between 1.5×10$^6$/ml and 1.8×10$^6$/ml and growing in the log-phase is centrifuged (200×g, i.e. 1000 rpm) for 10 min. Cells are washed once with washing medium (RPMI 1640 w/o L-glutamine) and pelleted (200×g, i.e. 1000 rpm; 10 min) Cell pellet is resuspended in culture medium and cell count is determined Cell concentration is adjusted to 1×10$^6$/ml. 100 µl cell suspension per well are plated into 96-well round bottom plates. Antibodies are diluted in cell culture medium containing 10% FBS and 100 µl antibody solution are added per well. Cells are incubated for 20 to 24 hrs at 37° C. in CO$_2$ incubator and thereafter stained with Vybrant apoptosis assay kit #2. Alexa Fluor 488 labelled Annexin V and propidium iodide solution are added to the cells and incubated for 15 min in the dark. Thereafter cells are resuspended in 400 µl AnnexinV binding buffer and subjected to FACS analysis using a BD FACS Canto. The percentage of AnnexinV positive/PI negative cells and AnnexinV/PI positive cells is determined in two-dimensional dot blots using FL1/FL2 channels. An isotype matched non-binding antibody (Sigma human IgG1) is used as negative control.

Figure 6:
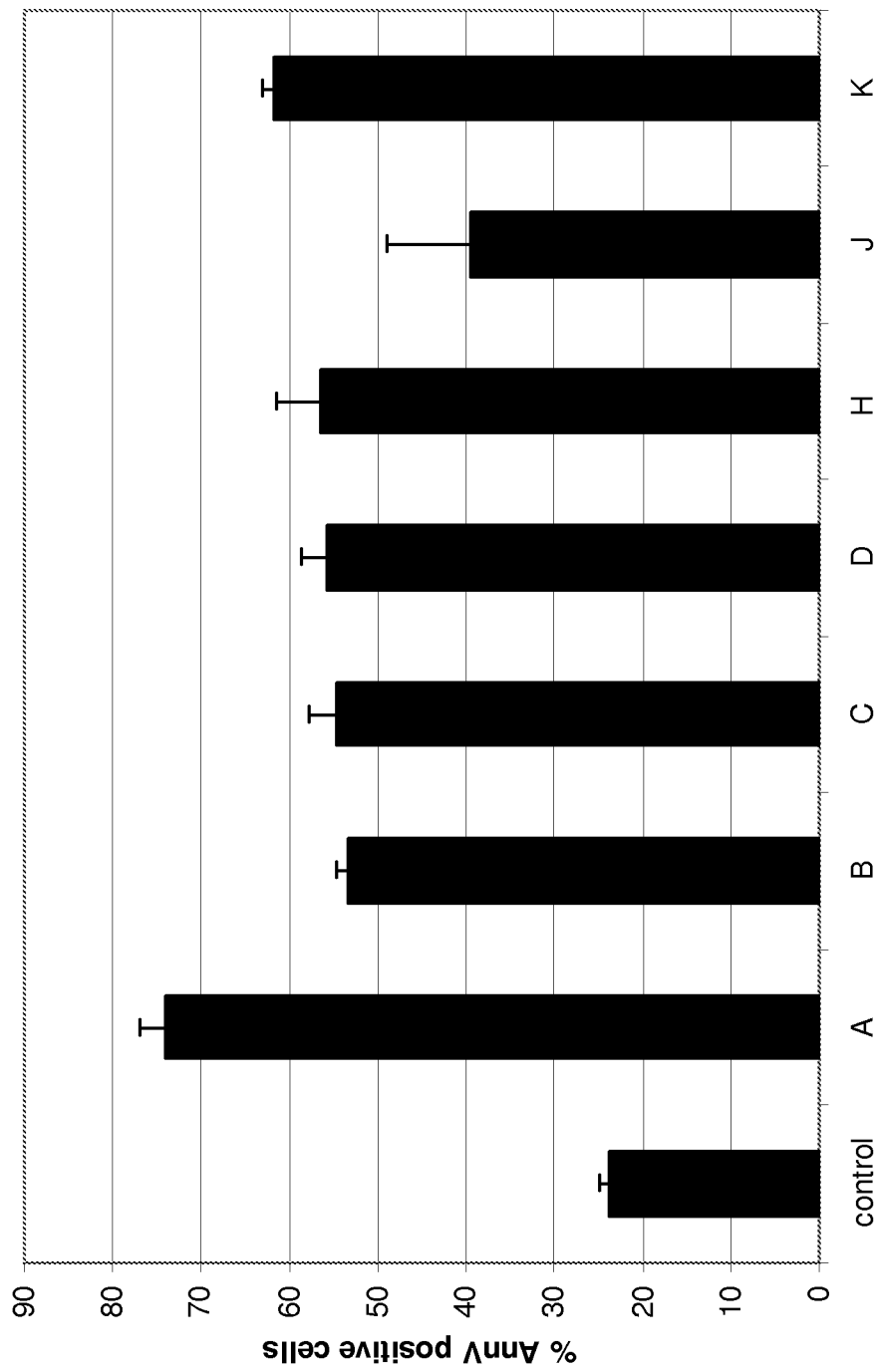
FIG. 6: Pro-apoptotic activity of humanized versions of A0 on Ramos cells

In FIG. 6, the pro-apoptotic effect of various humanized versions of mAb A on Ramos cells are shown. Cells are incubated with antibody at 10 µg/ml for 24 hrs, the total percentage of AnnexinV positive cells (PI positive and PI negative) is displayed. Parental mAb A shows potent pro-apoptotic activity. Surprisingly, humanized versions show a significantly reduced number of AnnexinV positive cells compared to the parental mAb A, indicative for altered pro-apoptotic activity of the humanized antibodies. In conclusion, humanization of MAb A leads to a reduction of its pro-apoptotic activity in this experimental setting.

EXAMPLE 7

ADCC Activity of Fc-Engineered Versions of Chimeric mAb A0

Figure 7:
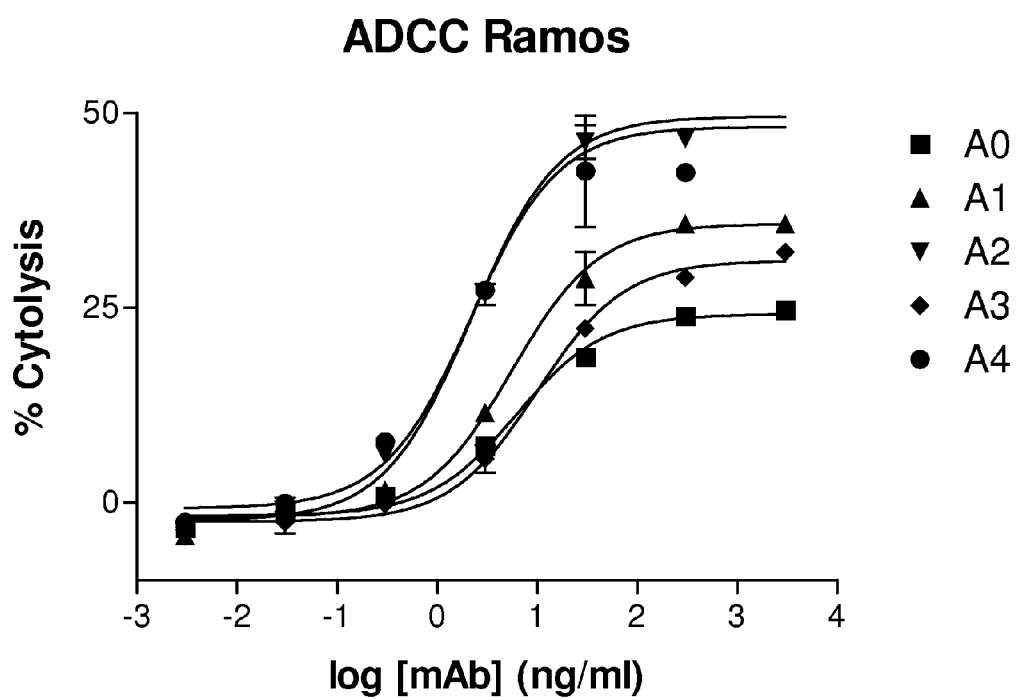
FIG. 7: ADCC activity of Fc-engineered versions of mAb A0 on Ramos cells

ADCC activity of Fc-engineered versions of mAb A0 (designated A1, A2, A3, A4; see Table 2) is assessed using Ramos cells as target cells. ADCC assay is performed as described above (Example 5). The result of the experiment is shown in FIG. 7. Fc-engineered versions of A0 show clearly improved potency and efficacy compared to the parent mAb A0. Certain Fc variants show improvement in maximal lysis of up to 100% compared to the parent mAb and improvement in EC$_{50}$ of up to 10-fold compared to the parent mAb. In conclusion, introduction of specific Fc mutants strongly increases the ADCC activity of chimeric mAb A0.

EXAMPLE 8

ADCC Activity of Fc-Engineered Versions of mAb B0

Figure 8:
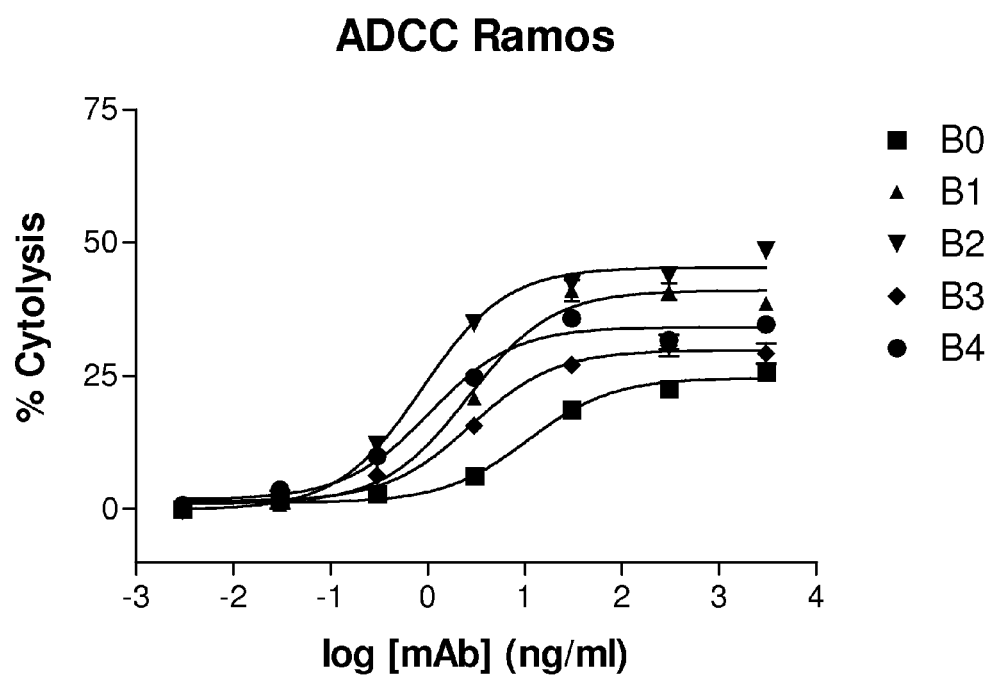
FIG. 8: ADCC activity of Fc-engineered versions of mAb B0 on Ramos cells

ADCC activity of Fc-engineered versions of mAb B0 (designated B1, B2, B3, B4; see Table 2) is assessed using Ramos cells as target cells. ADCC assay is performed as described above (Example 5). Fc-engineered versions of B0 show clearly improved potency and efficacy compared to the parent mAb B0. Certain Fc variants show improvement in maximal lysis of up to 80% compared to the parent mAb and improvement in $EC_{50}$ of up to 20-fold compared to the parent mAb. In conclusion, introduction of specific Fc mutants strongly increases the ADCC activity of humanized mAb B0. The results of the experiments are shown in FIG. 8.

EXAMPLE 9

Pro-Apoptotic Activity of mAbs A0 and B0

Figure 9:
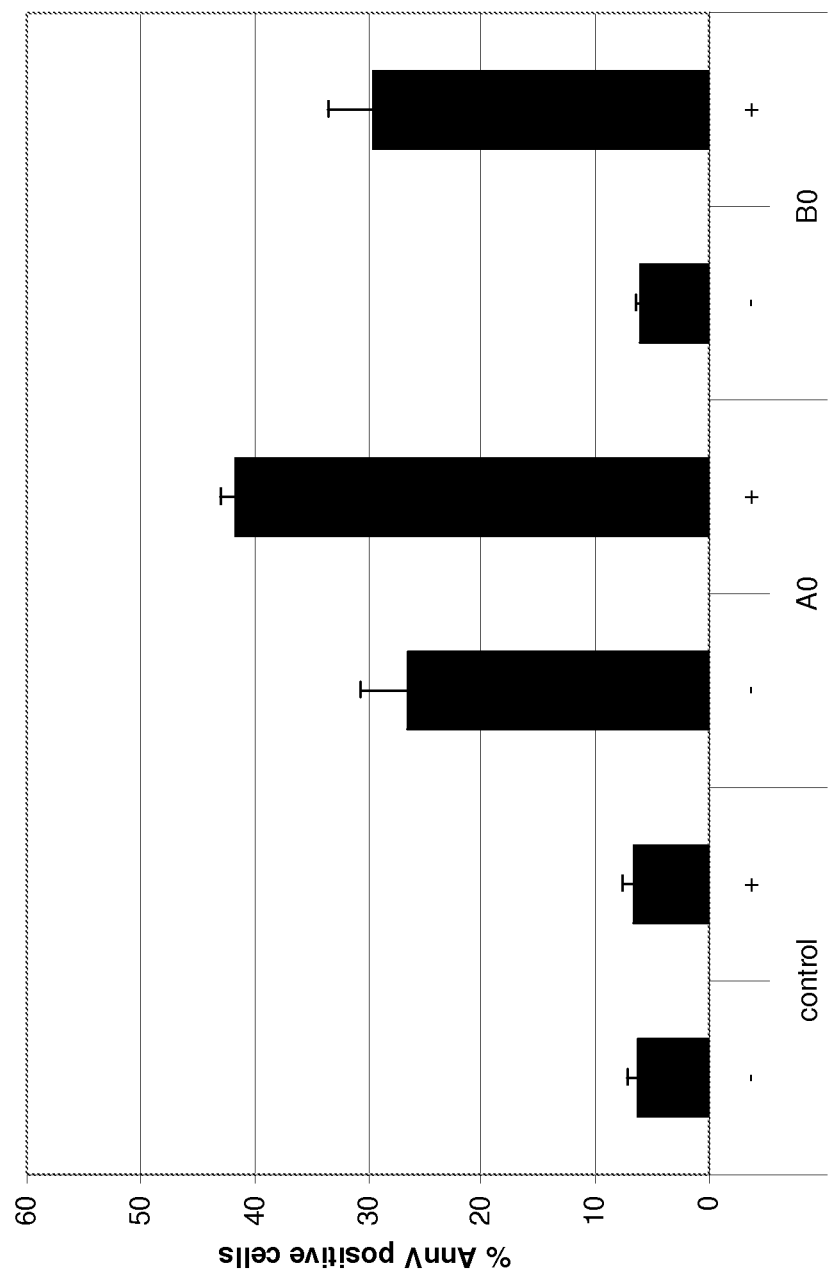
FIG. 9: Pro-apoptotic activity of mAb A0 and B0

The pro-apoptotic activity of mAbs A0 and B0 on Ramos cells before and after cross-linking with anti-IgG mAb is displayed in FIG. 9. The apoptotic assay is performed as described in Example 6, for antibody cross-linking an anti-human IgG antibody (γ-chain specific; Sigma) is added to the antibodies in a ratio of 1:1 and incubated for 15 min at 37° C. prior to adding to the target cells. In FIG. 9 the CD37-specific mAbs are added at a concentration of 1 µg/ml with and without cross-linking Chimeric mAb A0 is a potent inducer of apoptosis even without cross-linking, this effect is significantly enhanced after cross-linking of the mAb. Surprisingly, without cross-linking, the humanized mAb B0 is completely devoid of pro-apoptotic activity, however shows potent pro-apoptotic activity after cross-linking with anti-IgG Ab. In conclusion, this experiment shows that pro-apoptotic activity of a humanized version of mAb A0 can be restored after antibody cross-linking.

EXAMPLE 10

Pro-Apoptotic Activity of Fc-Engineered Versions of mAb A0

Figure 10:
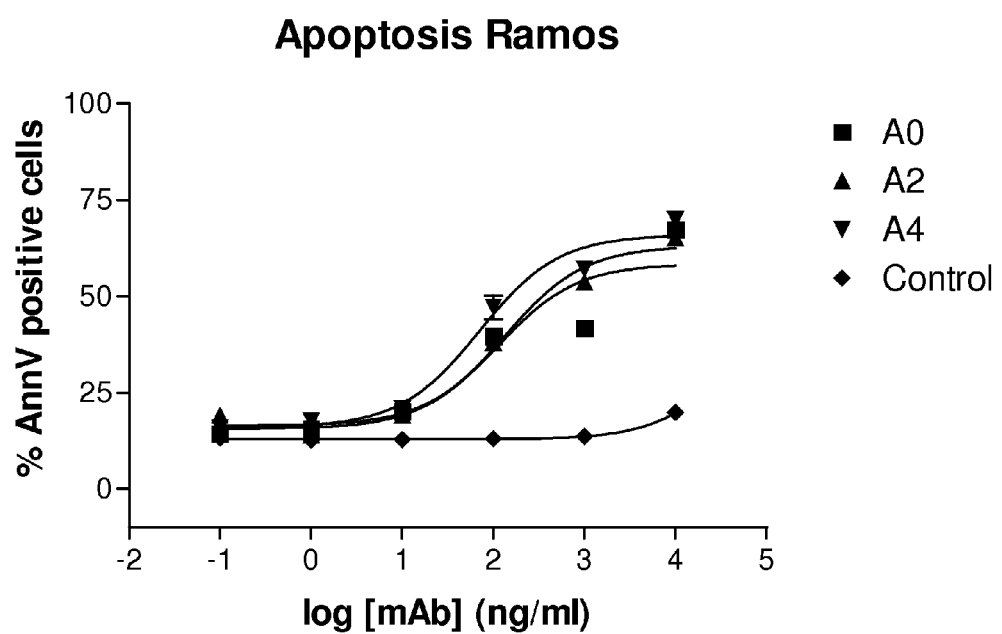
FIG. 10: Pro-apoptotic activity of Fc-engineered versions of mAb A0

The pro-apoptotic activity of Fc-engineered versions of chimeric mAb A0 on Ramos cells is assessed by AnnexinV/PI staining as described in Example 6. Parent1 antibody A0 and Fc-engineered variants A2 and A4 are titrated over a concentration range from 0.1 to 10.000 ng/ml. As can be seen in FIG. 10, all 3 antibodies show similar pro-apoptotic activity. In conclusion, this experiment shows that Fc-engineering of mAb A0 does not alter its pro-apoptotic activity.

EXAMPLE 11 a) B Cell Depleting Activity of Fc-Engineered Antibodies A2 and B2 in a Whole Blood Assay The efficacy and potency of depletion of normal B cells from human blood is assessed using a whole blood assay. In this assay format, the test antibody is added to EDTA-treated samples of human blood from healthy individuals and subsequently, after 3 to 4 hrs incubation at 37° C., the number of B cells is quantitatively measured by a 4-color FACS assay. By comparison to buffer or IgG controls, the degree of B cell depletion by the test agent can be calculated. Due to the presence of human IgG levels and effector cells similar to the situation in human beings in vivo, this assay type is considered of high relevance for predicting the effect of the test antibodies in vivo.

A quantitative FACS assay is used to determine the number of B cells and/or spiked Ramos cells in blood samples derived from healthy individuals. Quantification is performed using BD Trucount tubes which contain a known number of fluorescent beads which serve as internal standard for quantification of the cell population of interest. B cells are identified by 4-colour analysis using 4 different CD markers (CD3/CD14/CD19/CD45) in combination with FSC/SSC analysis.

270 µl fresh blood per well is incubated in a 48 well plate together with 30 µl antibody dilution (in PBS) or PBS (buffer control) in duplicates. Samples are incubated for 4 h at 37° C. and thereafter immediately placed on ice. 33 µl of CD marker master mix is added to Trucount tubes and 50 µl of the blood-antibody mixture is added. Samples are vortexed and incubated for 15 min at room temperature. Thereafter 450 µl of lysis buffer is added, vortexed, and incubated for additional 15 min at room temperature. Samples are placed on ice and immediately subjected to FACS analysis using a BD FACS Canto™ Flow Cytometer. Evaluation of data is performed using the BD FACSDiva software (Version 5.0.2).

Figure 11A:
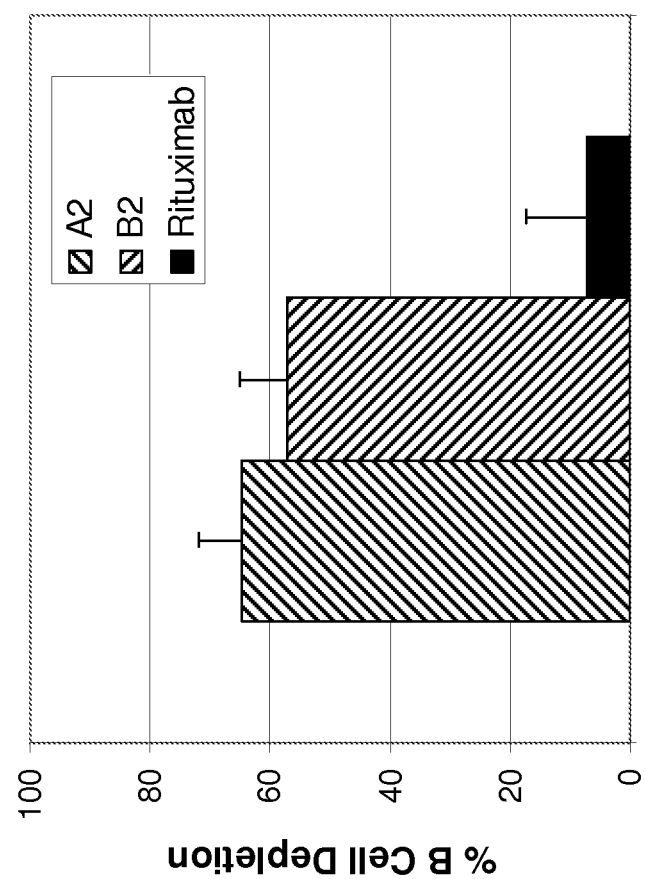
FIG. 11 A: Depletion of normal human B cells in a whole blood assay by Fc-engineered antibodies A2 and B2 in comparison to Rituximab FIG. 11 B: Superior B cell depleting activity of antibodies after Fc-engineering in comparison to Rituximab FIG. 11 C: Antibodies A2 and B2 do not deplete T cells and monocytes in whole blood assays
Figure 11B:
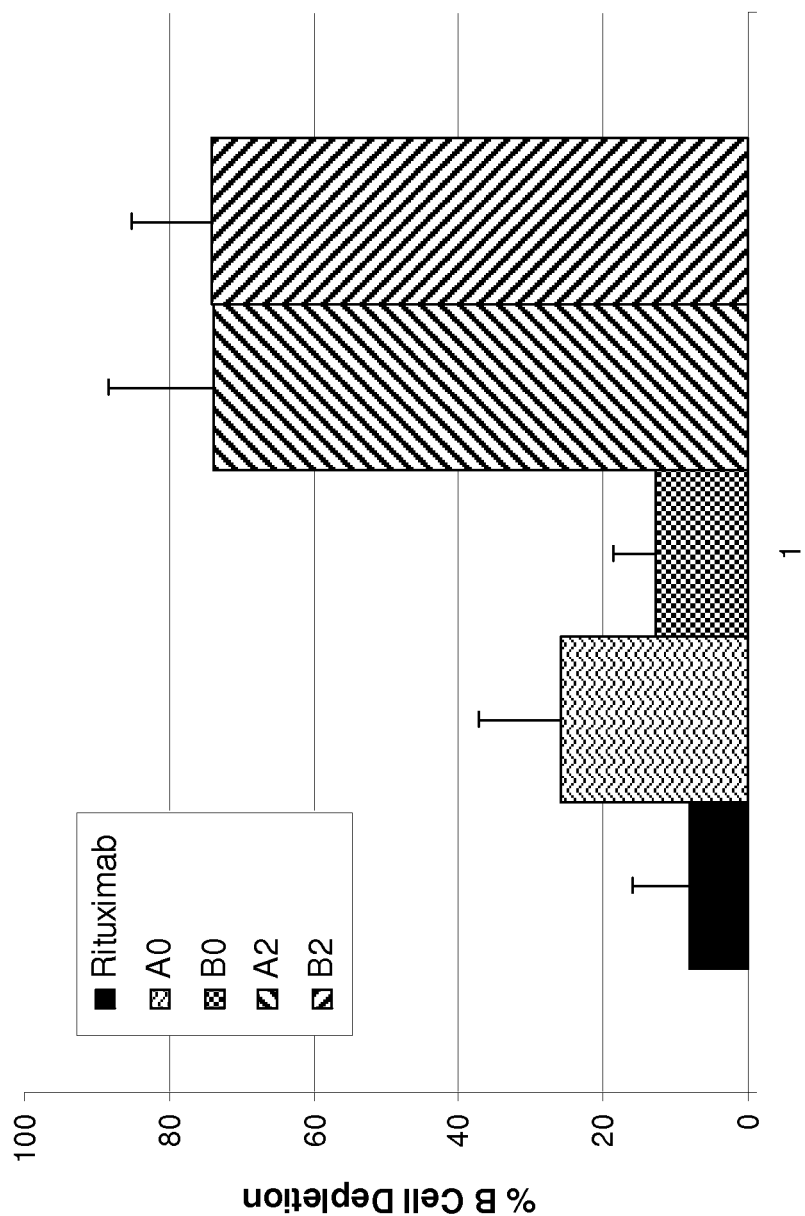

Fc-engineered chimeric and humanized mAbs A2 and B2 show excellent potency on normal B cell depletion with $EC_{50}$ values ranging from 0.15 to 0.35 nM. The degree of normal B cell depletion ranges from 57% to 65%. Rituximab, a registered antibody used for the treatment of B-NHL, is tested in parallel and yields significantly lower depletion of B-cells in this assay format (FIG. 11 A).

b) Fc-Engineering Introduces Superior B Cell Depleting Activity of A0 and B0 Compared to Rituximab The effect of mAbs on B cell depletion in human blood derived from healthy individuals is assessed as described in a). The non Fc-engineered mAbs A0 and B0 show B cell depleting activity in the range from 13% to 26%, similar to Rituximab. Fc-engineering results in a dramatic increase of B cell depleting activity for both mAbs, with a mean percentage of depletion of 75%. This clearly demonstrates the superiority of A2 and B2 compared to Rituximab (FIG. 11 B).

c) Antibodies A2 and B2 do not Deplete T Cells and Monocytes in Whole Blood Assays The effect of A2 and B2 on T lymphocytes (CD3-positive) and monocytes (CD14-positive) is assessed in parallel to the effect on B lymphocytes. No significant change of either T cell numbers or monocyte numbers is observed, whereas a significant reduction of the number of B cells is seen (FIG. 11C). This indicates that A2 and B2 specifically deplete B cells from human blood.

EXAMPLE 12

Fc-Engineering Introduces Superior ADCC Activity Compared to Rituximab

Figure 12:
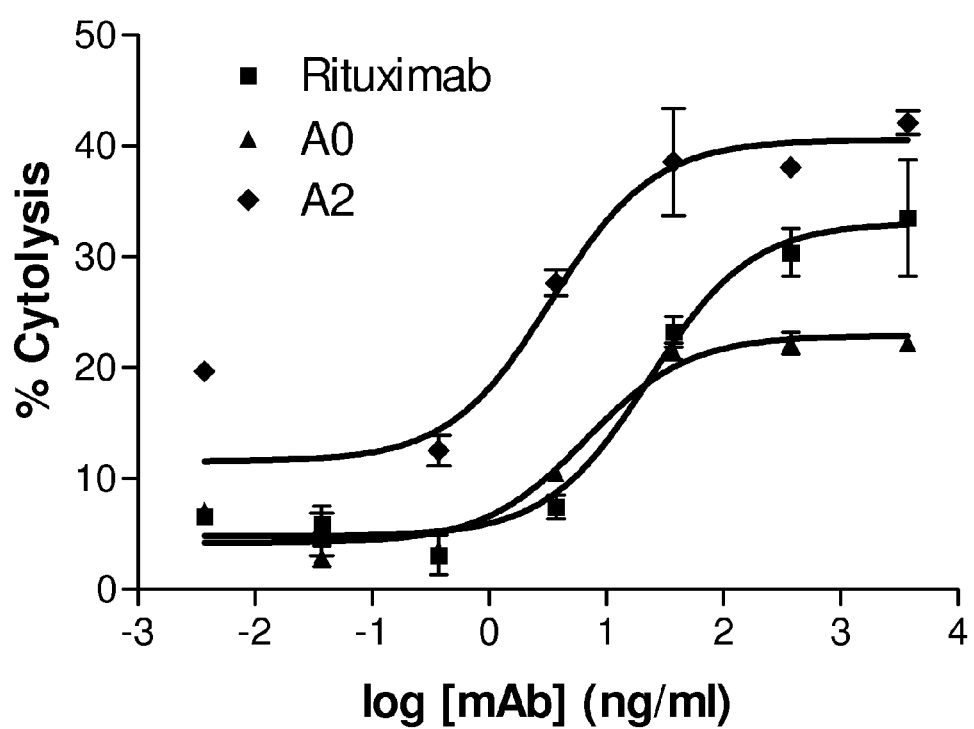
FIG. 12: Superior ADCC activity after Fc-engineering compared to Rituximab

ADCC activity of the Fc-engineered version A2 of mAb A0 is assessed using Ramos cells as target cells. ADCC assay is performed as described above (Example 5). The non Fc-engineered antibody A0 shows a maximal lysis of Ramos target cells which is inferior to Rituximab, an antibody specific for CD20 which is an approved treatment for patients suffering from B cell lymphomas. Surprisingly, Fc-engineering of A0 leads to a clearly improved potency and efficacy of A2 over Rituximab. This indicates, that at similar antigen densities of CD20 and CD37 on Ramos cells the Fc-engineered anti-CD37 mAb A2 shows clearly improved ADCC activity than Rituximab (FIG. 12).

EXAMPLE 13

Figure 13:
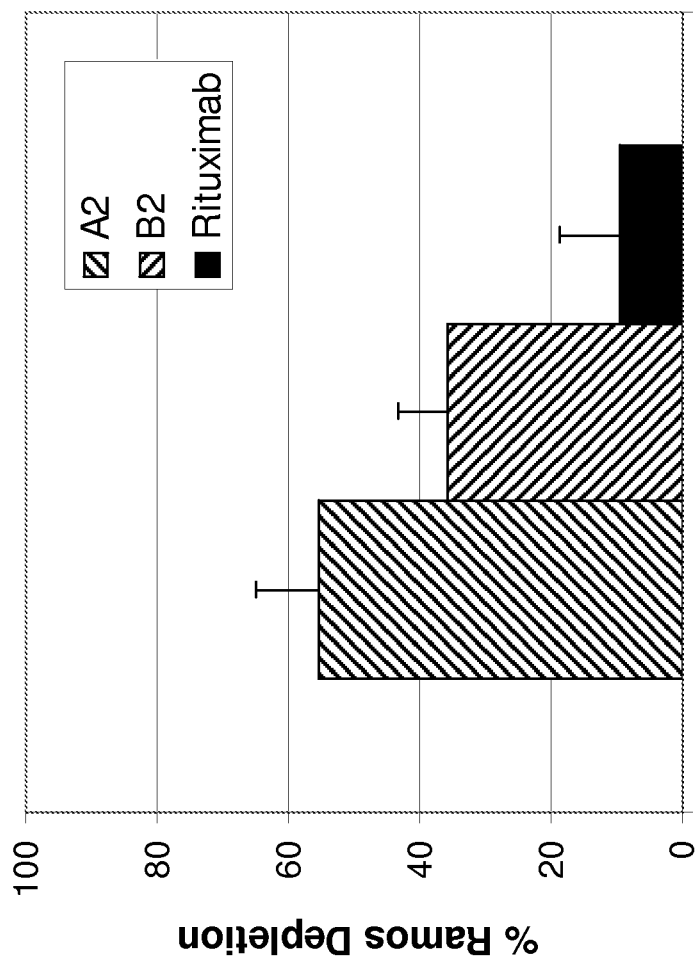
FIG. 13: Depletion of Ramos Burkitt's lymphoma cells in a whole blood assay by Fc-engineered antibodies A2 and B2 in comparison to Rituximab

Lymphoma Cell Depleting Activity of Fc-Engineered Antibodies A2 and B2 in a Whole Blood Assay The efficacy and potency of depletion of Ramos cells, a Burkitt's lymphoma derived cell line from human blood is assessed using a whole blood assay as described in Example 11. In a modification of the assay, Ramos tumor cells are spiked in about a tenfold excess compared to endogenous B cells into the whole blood matrix, and their depletion is also monitored by FACS analysis. Fc-engineered chimeric and humanized mAbs A2 and B2 show good potency on Ramos cell depletion with $EC_{50}$ values ranging from 0.35 to 0.54 nM. The degree of Ramos cell depletion ranges from 36% to 55%. Rituximab, a registered antibody used for the treatment of B-NHL, is tested in parallel and yields significantly lower depletion of Ramos cells in this assay format (FIG. 13).

EXAMPLE 14

In Vivo Efficacy of Fc-Engineered Antibodies A2 and B2 in Disease-Related Model

Figure 14:
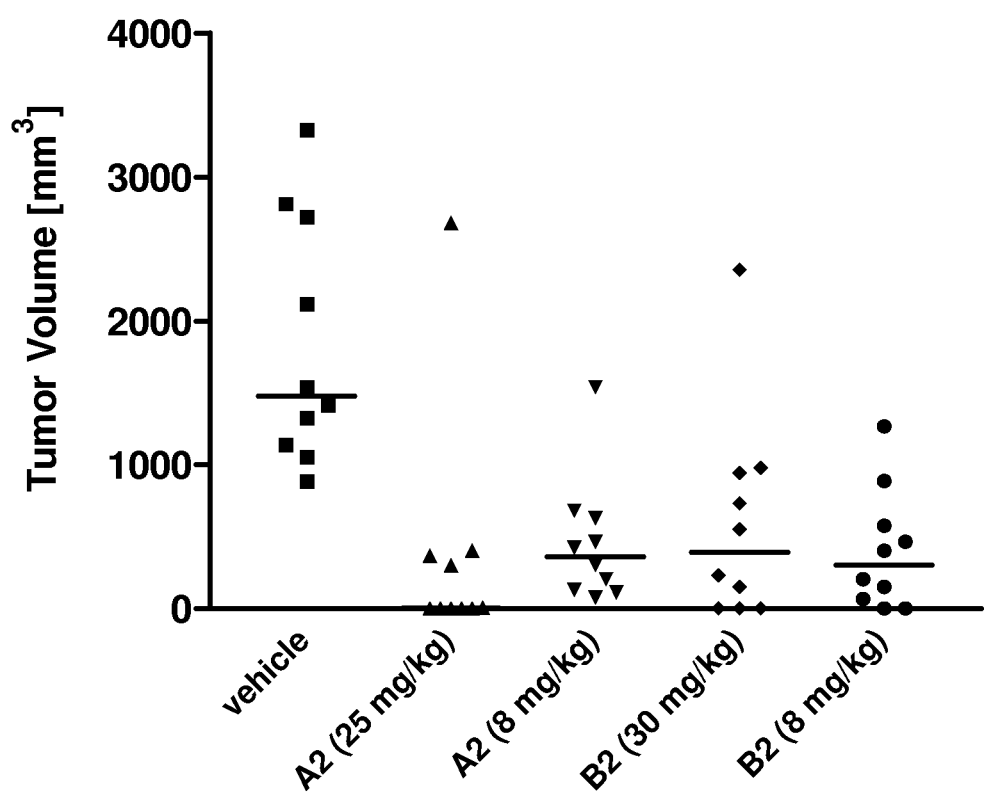
FIG. 14: In vivo tumor growth inhibition of Ramos xenograft tumors in nude mice by Fc-engineered antibodies A2 and B2

The in vivo anti-tumor efficacy of mAbs A2 and B2 is assessed using a Ramos Burkitt's lymphoma model in nude mice. CD37-positive Ramos cells are injected subcutaneously into the flank of the animals and i.v. treatment of the animals started when tumors are established. A twice weekly treatment schedule is chosen (q3/4d), two different doses (8 mg/kg and 25 mg/kg) are tested in parallel. Both mAbs show significant anti-tumor efficacy with T/C values ranging from 0.2% to 26%. No significant difference between the two dose levels and between the two antibodies are observed. However, there is a trend towards better efficacy in the high dose A2 treated animals, with T/C of 0.2% and 5/10 complete tumor regressions. All treatments are well tolerated with no apparent weight loss. In conclusion, mAbs A2 and B2 showed significant anti-tumor efficacy in the Ramos Burkitt's lymphoma model, with maximum activity already obtained at the 8 mg/kg dose level. The activity is comparable to that of rituximab which is tested in parallel. It has to be noted that the in vivo activity observed with the Fc-engineered antibodies A2 and B2 may be underestimated since these mAbs are optimized for interaction with human but not murine effector cells. This optimized interaction, which leads to strongly improved ADCC activity in vitro when using human effector cells (Example 8), is not reflected in the mouse model used. However, the data obtained in this experiment (shown in FIG. 14) provide in vivo proof of concept of CD37 targeting and thus can be used for estimating the therapeutic dose in humans.

EXAMPLE 15

Correlation of Pharmacokinetic and Pharmacodynamic Effect of A2 and B2 in Mice for Estimating the Therapeutic Dose in Humans A correlation between the serum concentrations of A2 and B2 to their pharmacodynamic effect is established in mice using the Ramos tumor xenograft model. These studies demonstrate that a dose of 8 mg/kg A2 and B2 (formulated in a citrate buffer: 25 mM Na-Citrate, 115 mM NaCl, 0.04% Tween 80, pH 6.0) causes significant retardation of tumor growth in this aggressive s.c. (subcutaneous) tumor model using a standard q3 or 4d antibody dosing schedule in mice, thus indicating continued activity throughout the dosing interval. Furthermore, pharmacokinetic data are established for the same dose.

Using this PK/PD association in mice, an estimated human dose can be calculated using published data for the clearance (CL) of humanized antibodies in humans (Lobo et al., 2004).

Full calculation for A2:
Mean $AUC(0-\infty)$ after single dose of 8 mg/kg=6099 µg·h/mL.
Given $AUC(0-\infty)$ in mice=$AUC(ss,\tau)$ in mice, and $AUC(ss,\tau)/\tau=C(ave,ss)$.
$C(ave,ss)$ in mice (for $\tau$=84 hours)=73 µg/mL, which is presumably equivalent to $C(ave,ss)$ in men (for $\tau$=168 h).
Since $AUC(ss,\tau)$ in men=D/CL, and using the humanized antibody clearance (CL) range in humans reported by Lobo et al, 2004: CL=7 mL/h/70 kg to 15 mL/h/70 kg.
For 7 mL/h/70 kg: 168 hr×7=1176 mL×73 µg=86 mg.
For 15 mL/h/70 kg: 168 hr×15=2520 mL×73 µg=184 mg.
Therefore, for A2, the estimated weekly dose for a 70 kg human is in the range of 86 to 184 mg. Using the same assumptions as described above, the calculated estimated human weekly dose for B2 for a 70 kg human is 189 to 404 mg.

EXAMPLE 16

Antibodies A2 and B2 Show ADCC Activity on Multiple Myeloma Cells

Figure 15:
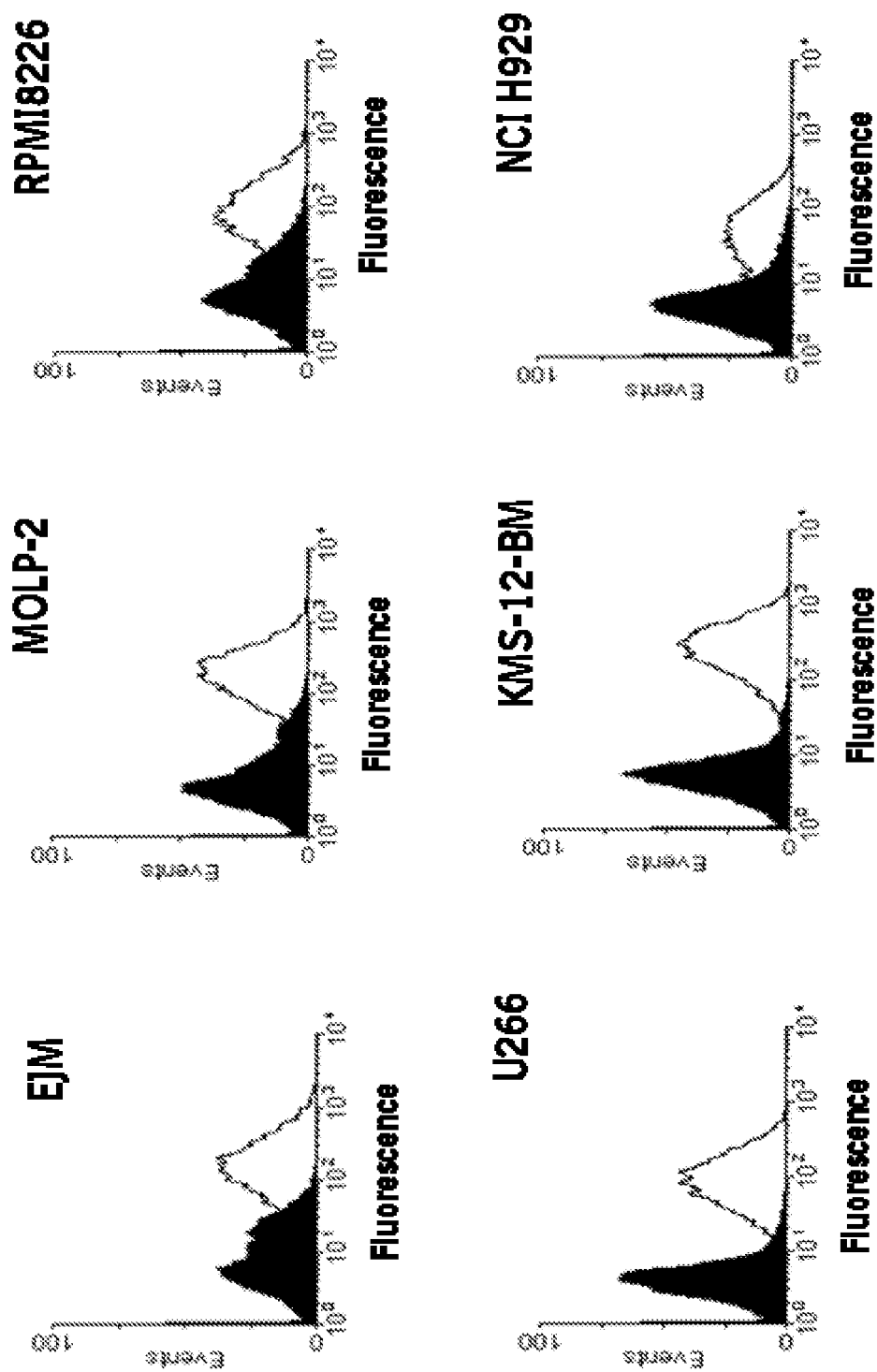
FIG. 15: Expression of CD37 on multiple myeloma cells
Figure 16:
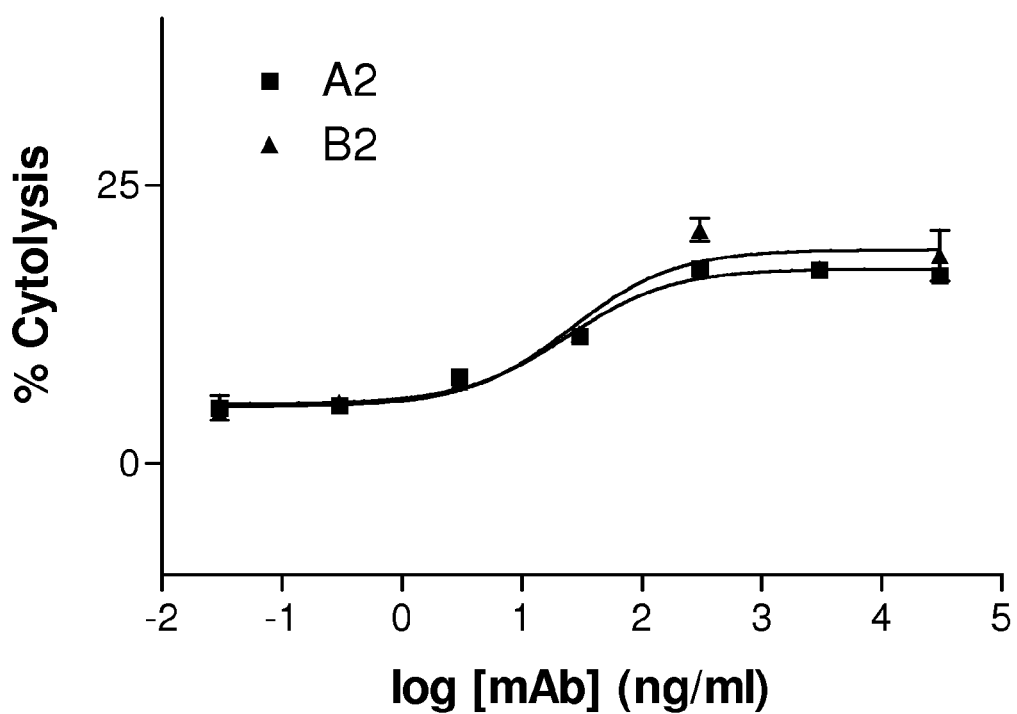
FIG. 16: ADCC activity of antibodies A2 and B2 on multiple myeloma cells

The expression of CD37 on a panel of multiple myeloma cell lines is assessed by FACS analysis using antibodies specific for CD37. Cells are either incubated with a directly fluorescently labeled anti-CD37 antibody or an unlabeled CD37-specific antibody followed by a second fluorescently labeled antibody directed against the primary antibody. The fluorescence activity of the labeled cells is measured with a FACS Canto Flow Cytometer (BD Biosciences) and the fluorescence intensity is recorded as MFI using the FACS Diva Software. 6 out of 11 tested multiple myeloma demonstrate cell surface expression of CD37 (FIG. 15). One cell line (RPMI 8226) is subsequently tested in an ADCC assay as described in Example 5 using the CD37-specific antibodies A2 and B2. Both antibodies demonstrate potent ADCC activity on RPMI 8226 cells with $EC_{50}$ values in the range of 25 ng/ml and a maximal cell lysis of about 20% (FIG. 16). This example demonstrates that CD37-positive multiple myeloma cells are susceptible to ADCC mediated cell lysis using the CD37-specific mAbs A2 and B2.

FIG. 15 shows the FACS analysis of six multiple myeloma derived cell lines for CD37 expression. The open curves indicate reactivity with the CD37-specific antibody, the filled curves represent the negative control antibody.

EXAMPLE 17

Pro-Apoptotic Activity of Antibodies A2 and B2 on Patient-Derived CLL Cells

The pro-apoptotic activity of A2 and B2 is assessed on patient-derived chronic lymphocytic leukemia (CLL) cells. Peripheral blood mononuclear cells (PBMCs) are prepared from a patient with diagnosed CLL, after informed consent according to the declaration of Helsinki has been obtained.

Figure 17:
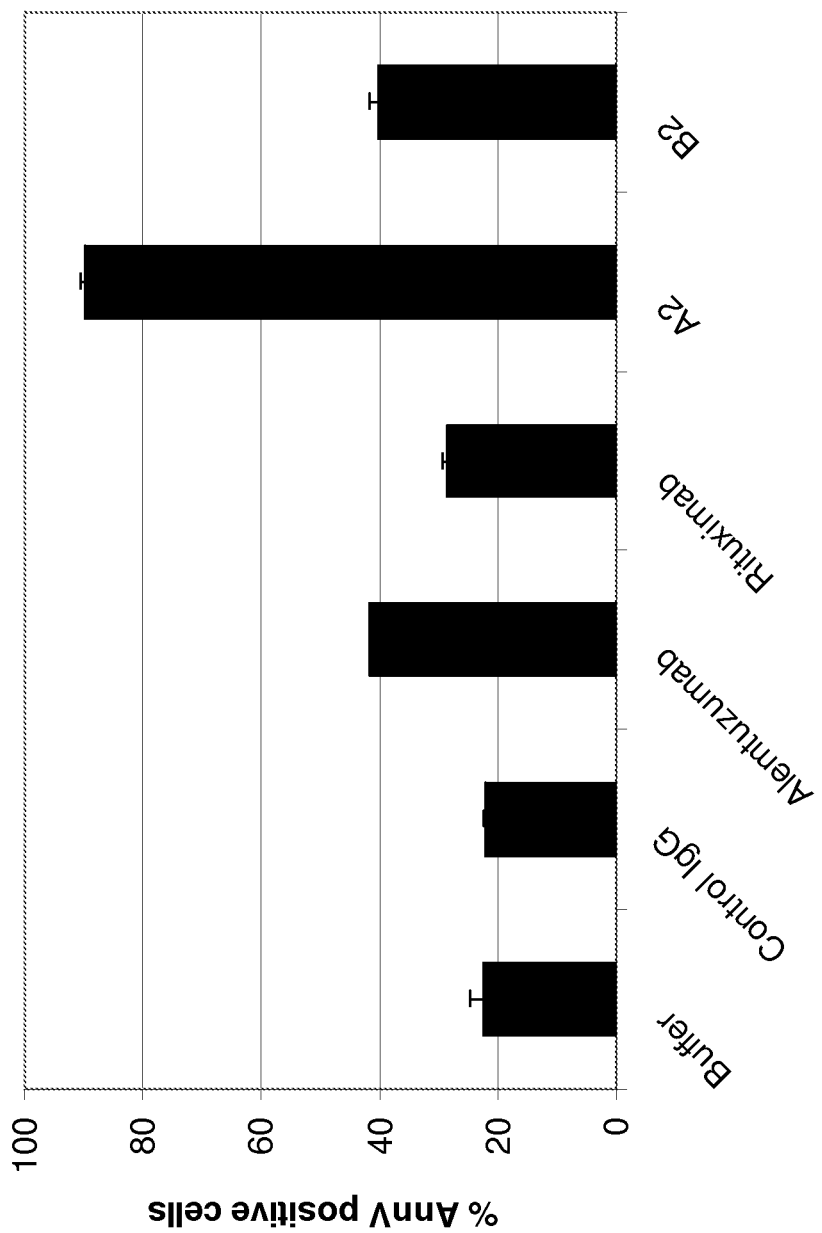
FIG. 17: Pro-apoptotic activity of antibodies A2 and B2 on patient-derived CLL cells

The primary CLL cells are purified from freshly collected blood according to Ficoll-Paque® plus procedure (StemCell Technologies, Meylan, France) and stored at 4° C. in RPMI 1640 culture medium containing 10% heat inactivated human AB serum (Sigma, France) until use. The culture medium for primary CLL cells is RPMI 1640 supplemented with 2 mM L-glutamine and 10% of heat inactivated human AB serum. For experimental use, primary CLL cells are counted in a hemocytometer and their viability is assessed by 0.25% trypan blue exclusion. The viability of CLL samples is more than 90%. Cells are incubated at 37° C. for 24 hours with the antibodies at 30 µg/ml and thereafter the percentage of AnnexinV positive cells is determined as described in Example 6. As shown in FIG. 17, Fc-engineered antibodies A2 and B2 show strong pro-apoptotic activity on the primary CLL cells with about 90% (A2) and 40% (B2) AnnexinV positive cells. Both mAbs are clearly superior to rituximab, a B cell-specific antibody approved for the treatment of B-NHL. Mab A2 demonstrates also clearly superior activity compared to alemtuzumab, an antibody approved for the treatment of B-CLL.

EXAMPLE 18

Generation of a Transgenic Mouse Model in which the Endogenous CD37 Gene is Replaced by its Human Homologue A targeting vector is constructed which contains the coding sequence of human CD37 (BAC (bacterial artificial chromosome) IDs: RP11-433N13, RP11-50I11) flanked by non-translated sequences. This targeting vector (which contains, in addition, loxP sites flanking exons 3-4 and the neo selection marker flanked by frt sites) is then used for homologous recombination, using mouse ES cells and standard technology to replace exons 1-8 of the mouse genomic sequence with the human counterpart sequences, To this end, the C57BL/6N ES cell line is grown on a mitotically inactivated feeder layer comprised of mouse embryonic fibroblasts (MEF) in DMEM High Glucose medium containing 20% FBS (PAN) and 1200 u/mL Leukemia Inhibitory Factor (Millipore ESG 1107). $1\times10^7$ cells and 30 g of linearized DNA vector are electroporated (Biorad Gene Pulser) at 240 V and 500 F. G418 selection (200 g/mL) started on d2. Counterselection with Gancyclovir (2 M) starts on d5 after electroporation. ES clones are isolated on d8 and analyzed by Southern Blotting according to standard procedures, e.g. by the use of radiolabelled DNA probes specific for the target gene after expansion and freezing of clones in liquid nitrogen. Transgenic animals are then generated by standard procedures known in the art, e.g. by blastocyst injection and subsequent generation of chimeric animals. Animals heterozygous and homozygous for human CD37 are obtained by conventional breeding of chimeric and heterozygous animals, respectively. The successful knock-out of the murine CD37 gene and the knock-in of the human CD37 gene is monitored at the protein level using standard procedures, e.g. FACS analysis of peripheral blood lymphocytes or immunohistochemical analysis of tissue sections.

EXAMPLE 19

Generation of Surrogate Antibodies

Monoclonal antibodies specific for macaque CD37 are generated by genetic immunization of mice and rabbits using the complete coding sequence of the macaque CD37 antigen (Acc. No. ENSMMUT00000020744). Specific antibodies are selected using recombinant HEK293 or CHO cells expressing the macaque CD37 antigen, e.g. by standard ELISA or FACS techniques. The variable heavy and light chain coding sequences of these antibodies are retrieved by PCR cloning and used for generation of chimeric antibodies (as described in Example 1) which harbor the VH and VL region derived from the murine or rabbit starting antibody and an Fc portion identical to that of an antibody of the invention, e.g. A2 or B2. The binding and functional properties can be investigated by the use of assay systems which utilize macaque CD37 expressing cells as target cells, e.g. for binding, FACS, Scatchard analysis, ADCC and apoptosis assays. Ultimately, the surrogate antibody is selected by virtue of its B cell depleting activity in Cynomolgus monkey blood in vitro.

EXAMPLE 20

Preparation of Clones for Producing the Antibodies

In order to prepare clones for producing antibodies of the invention, e.g. antibodies A2, A4, B2 or B4, the DNA molecule encoding the complete heavy chain, e.g. with the sequence shown in SEQ ID NO: 27, 31, 35 or 39, respectively, is inserted into the eukaryotic expression vector designated pBI-26, encoding in addition the selection marker dihydrofolate reductase from hamster.

The DNA molecule encoding the complete light chain, depicted in SEQ ID NO: 29, 33, 37 and 41, respectively, is inserted into the eukaryotic expression vector designated pBI-49, encoding in addition the selection marker neomycin phosphotransferase. The DNA sequences of the entire heavy and light chains are sequenced completely.

The hamster cell line CHO-DG44, grown in suspension in chemically defined media, is co-transfected with the eukaryotic expression vectors for the heavy and for the light chain of the antibodies, as described above. Transfected cells are selected in medium without hypoxanthine and thymidine and in the presence of the antibiotic G418. Subsequently, cells are subjected to stepwise selection and amplification using increasing concentrations of methotrexate (MTX). From the 800 nM MTX amplification step, a single cell clone is selected based on growth performance and antibody production in spinner runs, and is cryopreserved in a Safety Cell Bank (SCB).

REFERENCES

American Cancer Society (Cancer Facts & Figures 2005).
Baker and Jones, Curr Opinion in Drug Discovery & Development, 10, 219-227, 2007.
Barbas, et al., Proc. Nat. Acad. Sci, USA 91:3809-3813, 1994.
Barrena et al., Leukemia 19: 1376-1383, 2005.
Belov et al., Cancer Research 61: 4483-4489, 2001.
Boulianne G. L., Hozumi N. and Shulman, M. J., Production of functional chimeric mouse/human antibody. Nature 312: 643, 1984.
Brockhoff G, Hofstaedter F, Knuechel R., Cytometry 1994, 17(1):75-83.
Buchsbaum et al., Cancer Research 52: 6476-6481, 1992.
Chothia and Lesk., J. Mol. Biol. 196: 901-917, 1987.
Coiffier B, et al. Rituximab (anti-CD20 monoclonal antibody) for the treatment of patients with relapsing or refractory aggressive lymphoma: a multicenter phase II study. Blood 1998; 92: 1927-1932.

Coiffier, JCO, 23, 6387-93, 2005.

Edelman et al. Proc Natl Acad Sci USA 63: 78-85, 1969.

Feugier P, et al. Long-term results of the R-CHOP study in the treatment of elderly patients with diffuse large B-cell lymphoma: a study by the Groupe d'Etude des Lymphomes de l'Adulte. J Clin Oncol 2005; 23: 4117-4126.

Foran J M, et al. European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma. J Clin Oncol 2000; 18: 317-324.

Forstpointner R, et al. The addition of rituximab to a combination of fludarabine, cyclophosphamide, mitoxantrone (FCM) significantly increases the response rate and prolongs survival as compared with FCM alone in patients with relapsed and refractory follicular and mantle cell lymphomas: results of a prospective randomized study of the German Low-Grade Lymphoma Study Group. Blood, 2004; 104: 3064-3071.

Francisco et al., Blood, 2003 Aug. 15; 102(4):1458-65.

Frank, et al., Methods Enzymol. 154: 221-249, 1987.

Gait, M. J., Oligonucleotide Synthesis. A Practical Approach. IRL Press, Oxford, UK (1984).

Goldenberg D M and Sharkey R M, Oncogene (2007) 26, 3734-3744. Novel radiolabeled antibody conjugates.

Hainsworth J D. Prolonging remission with rituximab maintenance therapy. Semin Oncol 2004; 31: 17-21.

Hawkins et al., J. Mol. Biol. 254:889-896, 1992.

Hayden and Mandecki. Gene synthesis by serial cloning of oligonucleotides. DNA 7(8): 571-7, 1988.

Hertz T, Yanover C: PepDist: A new framework for protein-peptide binding prediction based on learning peptide distance functions. BMC Bioinform (2006) 7 (Suppl 1):S3-S17.

Hiddemann W, et al. Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study. Group. Blood 2005; 106: 3725-3732 (2005a).

Hiddemann W, et al. Treatment strategies in follicular lymphomas: current status and future perspectives. J Clin Oncol 2005b: 23; 6394-6399.

Howard O M, et al. Rituximab and CHOP induction therapy for newly diagnosed mantle-cell lymphoma: molecular complete responses are not predictive of progression-free survival. J Clin Oncol 2002; 20: 1288-1294.

Ichimura et al., J. Antibiot. (Tokyo), 44, 1045-53, 1991.

Jackson et al., 1995, J. Immunol. 154(7):3310-9.

Johnson S, Bird R E. Construction of single-chain derivatives of monoclonal antibodies and their production in *Escherichia coli*. Methods Enzymol. 203: 88-98, 1991.

Jones T D, Hanlon M, Smith B J, Heise C T, Nayee P D, Sanders D A, Hamilton A, Sweet C, Unitt E, Alexander G, Lo K M et al: The development of a modified human IFN-α2b linked to the Fc portion of human IgG1 as a novel potential therapeutic for the treatment of hepatitis C virus infection. J Interferon Cytokine Res (2004) 24(9): 560-572.

Jones T D, Phillips W J, Smith B J, Bamford C A, Nayee P D, Baglin T P, Gaston J S, Baker M P: Identification and removal of a promiscuous CD4+ T cell epitope from the C1 domain of Factor VIII. J Thromb Haemost (2005) 3(5): 991-1000.

Kabat E. A., Wu T. T., Perry H. M., Gottesman K. S. and Foeller C. Sequences of Proteins of Immunological Interest (5th Ed.). NIH Publication No. 91-3242. U.S. Department of Health and Human Services, Public Health Service, National Institutes of Health, Bethesda, Md. 1991.

Kahl B, et al. Maintenance rituximab following induction chemoimmunotherapy may prolong progression-free survival in mantle cell lymphoma: a pilot study from the Wisconsin Oncology Network. Ann Oncol, 2006; 17: 1418-1423.

Kaminski et al., JCO 10: 1696-1711, 1992.

Kipriyanow and Le Gall, Molecular Biotechnology 26: 39-60, 2004.

Knobeloch et al., Mol Cell Biol 20: 5363-5369, 2000.

van der Kolk L E, Baars J W, Prins M H, van Oers M H. Rituximab treatment results in impaired secondary humoral immune responsiveness. Blood, 2002, Sep. 15; 100(6):2257-9.

McLaughlin P, et al. Rituximab chimeric anti-CD20 monoclonal antibody therapy for relapsed indolent lymphoma: half of patients respond to a four-dose treatment program. J Clin Oncol 1998; 16: 2825-2833.

Lazar et al., Proc Natl Acad Sci USA. 2006 Mar. 14; 103(11):4005-10, 2006.

Ling and MacLennan, pp. 302-335 in Leucocyte Typing III. White Cell Differentiation Antigens, Oxford University Press, 1987.

Link et al., Journal Immunol 137: 3013-3018, 1986.

Lobo et al., J Pharm Sci 2004; 93(11):2645-2668.

Lowman et al., Biochemistry 30(45): 10832-10837, 1991.

Marks et al., Biotechnology 10:779-783, 1992.

Moldenhauer G., et al., 1987. Biochemical characterization and epitope analysis of B lymphocyte-specific surface antigens defined by clustering workshop monoclonal antibodies. In Leukocyte Typing 111. A. McMichael. ed. Oxford University Press, Oxford. p. 378.

Moldenhauer G.: CD37. J. Biol Regul Homeost Agents 2000; 14: 281-83.

Press et al., JCO 7, 1989.

Press O W, et al. Radiolabeled-antibody therapy of B-cell lymphoma with autologous bone marrow support. N Engl J Med 1993; 329: 1219-1224.

Reche P A, Glutting J P, Zhang H, Reinherz E L: Enhancement to the RANKPEP resource for the prediction of peptide binding to MHC molecules using profiles. Immunogenetics (2004), 56(6):405-419.

Remington: The Science and Practice of Pharmacy, 21st edition, Hendrickson R. Ed.

Romaguera J E, et al. High rate of durable remissions after treatment of newly diagnosed aggressive mantle-cell lymphoma with rituximab plus hyper-CVAD alternating with rituximab plus high-dose methotrexate and cytarabine. J Clin Oncol, 2005; 23: 7013-7023.

Sasse et al., J. Antibiot. (Tokyo), 53, 879-85, 2000.

Shier et al., 1995, Gene 169:147-155.

Schwartz-Albiez et al, Journal Immunol 140: 905-914, 1988.

Stemmer et al. Single-step assembly of a gene and entire plasmid from large numbers of oligodeoxyribonucleotides, Gene 164(1): 49-53, 1995.

van Spriel et al., Journal Immunol 172: 2953-2961, 2004.

Suzawa et al., Bioorg. Med. Chem., 8, 2175-84, 2000.

Tangri S, Mothe B R, Eisenbraun J, Sidney J, Southwood S, Briggs K, Zinckgraf J, Bilsel P, Newman M, Chesnut R, LiCalsi C, Sette A: Rationally engineered therapeutic proteins with reduced immunogenicity J Immunol (2005) 174(6):3187-3196.

Thomas D A, et al. Chemoimmunotherapy with hyper-CVAD plus rituximab for the treatment of adult Burkitt and Burkitt-type lymphoma or acute lymphoblastic leukemia. Cancer 2006; 106: 1569-1580.

Ye et al. Gene synthesis and expression in *E. coli* for pump, a human matrix metalloproteinase. Biochem Biophys Res Commun 186(1):143-9, 1992.

Yelton et al., 1995, Immunol. 155:1994-2004.

Zhao et al., Blood 104: Abstract 2515, 2004.

Zhao X B, Lapalombella R, Joshi T, Cheney C, Gowda A, Hayden-Ledbetter M S, Baum P R, Lin T S, Jarjoura D, Lehman A, Kussewitt D, Lee R J, Caligiuri M A, Tridandapani S, Muthusamy N, Byrd J C. Targeting CD37+ lymphoid malignancies with a novel engineered small modular immunopharmaceutical 2007; BLOOD, 1 Oct. 2007, VOLUME 110, NUMBER 7 (Epub ahead of print. Blood. 2007 Apr. 17)

The invention claimed is:

1. A monoclonal antibody that is a chimeric immunoglobulin that binds to human CD37, comprising
 (a) two identical heavy chains, each comprising (i) SEQ ID NO: 2, fused to (ii) SEQ ID NO: 24 or a mutated form of SEQ ID NO: 24, wherein the mutated form has no more than 1, 2 or 3 mutations relative to SEQ ID NO: 24 selected from the group consisting of:
  a substitution at position 332, numbered according to the Kabat EU numbering index, wherein the substitution at position 332 is I332E;
  a substitution a position 236, numbered according to the Kabat EU numbering index, wherein the substitution at position 236 is G236A; and
  a substitution at position 239, numbered according to the Kabat EU numbering index, wherein the substitution at position 239 is S239D;
 and
 (b) two identical light chains, each comprising SEQ ID NO: 4 fused to a human kappa light chain constant region.

2. The monoclonal antibody of claim 1, wherein each heavy chain comprises a sequence selected from the group consisting of
 SEQ ID NO: 2 fused to SEQ ID NO: 24;
 SEQ ID NO: 2 fused to a first mutated form of SEQ ID NO: 24, wherein SEQ ID NO: 24 is modified to have a single substitution at position 332, numbered according to the Kabat EU numbering index, wherein the single substitution is I332E;
 SEQ ID NO: 28;
 SEQ ID NO: 2 fused to a second mutated form of SEQ ID NO: 24, wherein SEQ ID NO: 24 is modified to have two substitutions, at positions 332 and 236, numbered according to the Kabat EU numbering index, wherein the two substitutions are I332E and G236A, respectively; and
 SEQ ID NO: 32.

3. The monoclonal antibody of claim 1, comprising
 (a) two heavy chains, each comprising SEQ ID NO: 2 fused to SEQ ID NO: 24; and two light chains, each comprising SEQ ID NO: 4 fused to SEQ ID NO: 26; or
 (b) two heavy chains, each comprising SEQ ID NO: 2 fused to a first mutated form of SEQ ID NO: 24, wherein SEQ ID NO: 24 is modified to have a single substitution at position 332, numbered according to the Kabat EU numbering index, wherein the single substitution is I332E; and two light chains, each comprising SEQ ID NO: 4 fused to SEQ ID NO: 26; or (c) two heavy chains, each comprising SEQ ID NO: 28; and two light chains, each comprising SEQ ID NO: 30; or (d) two heavy chains, each comprising SEQ ID NO: 2 fused to a second mutated form of SEQ ID NO: 24, wherein SEQ ID NO: 24 is modified to have two substitutions, at positions 332 and 236, numbered according to the Kabat EU numbering index, wherein the two substitutions are I332E and G236A, respectively; and two light chains, each comprising SEQ ID NO: 4 fused to SEQ ID NO: 26; or (e) two heavy chains, each comprising SEQ ID NO: 32; and two light chains, each comprising SEQ ID NO: 34.

4. A monoclonal antibody that is a chimeric immunoglobulin that binds to human CD37, comprising (a) two identical heavy chains, in which the sequence of each heavy chain is SEQ ID NO: 28; and (b) two identical light chains, in which the sequence of each light chain is SEQ ID NO: 30.

5. A pharmaceutical composition comprising the monoclonal antibody of claim 1, and a pharmaceutically acceptable carrier.

6. The pharmaceutical composition of claim 5, further comprising one or more additional therapeutic agents.

7. A method of depleting CD37 expressing B cells from a population of cells, comprising administering to said population of cells in vitro a monoclonal antibody that is a chimeric immunoglobulin that binds to human CD37, comprising (a) two identical heavy chains, each comprising (i) SEQ ID NO: 2, fused to (ii) SEQ ID NO: 24 or a mutated form of SEQ ID NO: 24, wherein the mutated form has no more than 1, 2, or 3 mutations relative to SEQ ID NO: 24 selected from the group consisting of:

a substitution at position 332, numbered according to the Kabat EU numbering index, wherein the substitution at position 332 is I332E;

a substitution at position 236, numbered according to the Kabat EU numbering index, wherein the substitution at position 236 is G236A; and a substitution at position 239, numbered according to the Kabat EU numbering index, wherein the substitution at position 239 is S239D; and (b) two identical light chains, each comprising SEQ ID NO: 4 fused to a human kappa light chain constant region, or a pharmaceutical composition comprising said monoclonal antibody.

8. A method for treating a patient suffering from a CD37 positive malignancy, comprising administering to said patient an effective amount of a monoclonal antibody that is a chimeric immunoglobulin that binds to human CD37, comprising (a) two identical heavy chains, each comprising (i) SEQ ID NO: 2, fused to (ii) SEQ ID NO: 24 or a mutated form of SEQ ID NO: 24, wherein the mutated form has no more than 1, 2, or 3 mutations relative to SEQ ID NO: 24 selected from the group consisting of:

a substitution at position 332, numbered according to the Kabat EU numbering index, wherein the substitution at position 332 is I332E;

a substitution at position 236, numbered according to the Kabat EU numbering index, wherein the substitution at position 236 is G236A; and a substitution at position 239, numbered according to the Kabat EU numbering index, wherein the substitution at position 239 is S239D; and (b) two identical light chains, each comprising SEQ ID NO: 4 fused to a human kappa light chain constant region.

9. A pharmaceutical composition comprising the monoclonal antibody of claim 4, and a pharmaceutically acceptable carrier.

10. The pharmaceutical composition of claim 9, further comprising one or more additional therapeutic agents.

* * * * *

SEQUENCE LISTING

```
<160> NUMBER OF SEQ ID NOS: 42

<210> SEQ ID NO 1
<211> LENGTH: 348
<212> TYPE: DNA
<213> ORGANISM: Mus musculus
<220> FEATURE:
<221> NAME/KEY: CDS
<222> LOCATION: (1)..(348)

<400> SEQUENCE: 1 gcg gtc cag ctg cag cag tct gga cct gag ctg gaa aag cct ggc gct      48
Ala Val Gln Leu Gln Gln Ser Gly Pro Glu Leu Glu Lys Pro Gly Ala
1               5                   10                  15 tca gtg aag att tcc tgc aag gct tct ggt tac tca ttc act ggc tac      96
Ser Val Lys Ile Ser Cys Lys Ala Ser Gly Tyr Ser Phe Thr Gly Tyr
            20                  25                  30 aat atg aac tgg gtg aag cag aat aat gga aag agc ctt gag tgg att     144
Asn Met Asn Trp Val Lys Gln Asn Asn Gly Lys Ser Leu Glu Trp Ile
        35                  40                  45 gga aat att gat cct tat tat ggt ggt act acc tac aac cgg aag ttc     192
Gly Asn Ile Asp Pro Tyr Tyr Gly Gly Thr Thr Tyr Asn Arg Lys Phe
    50                  55                  60 aag ggc aag gcc aca ttg act gta gac aaa tcc tcc agc aca gcc tac     240
Lys Gly Lys Ala Thr Leu Thr Val Asp Lys Ser Ser Ser Thr Ala Tyr
65                  70                  75                  80 atg cag ctc aag agt ctg aca tct gag gac tct gca gtc tat tac tgt     288
Met Gln Leu Lys Ser Leu Thr Ser Glu Asp Ser Ala Val Tyr Tyr Cys
                85                  90                  95 gca aga tcg gtc ggc cct atg gac tac tgg ggt caa gga acc tca gtc     336
Ala Arg Ser Val Gly Pro Met Asp Tyr Trp Gly Gln Gly Thr Ser Val
            100                 105                 110 acc gtc tct tct                                                      348
Thr Val Ser Ser
        115

<210> SEQ ID NO 2
<211> LENGTH: 116
<212> TYPE: PRT
<213> ORGANISM: Mus musculus

<400> SEQUENCE: 2

Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Ser Thr Ala Tyr
```

```
                    65                  70                  75                  80
Met Gln Leu Lys Ser Leu Thr Ser Glu Asp Ser Ala Val Tyr Tyr Cys
                        85                  90                  95

Ala Arg Ser Val Gly Pro Met Asp Tyr Trp Gly Gln Gly Thr Ser Val
                100                 105                 110

Thr Val Ser Ser
        115

<210> SEQ ID NO 3
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 3 gac atc cag atg act cag tct cca gcc tcc cta tct gca tct gtg gga    48
Asp Ile Gln Met Thr Gln Ser Pro Ala Ser Leu Ser Ala Ser Val Gly
1               5                   10                  15 gag act gtc acc atc aca tgt cga aca agt gaa aat gtt tac agt tat    96
Glu Thr Val Thr Ile Thr Cys Arg Thr Ser Glu Asn Val Tyr Ser Tyr
            20                  25                  30 ttg gct tgg tat cag cag aaa cag gga aaa tct cct cag ctc ctg gtc   144
Leu Ala Trp Tyr Gln Gln Lys Gln Gly Lys Ser Pro Gln Leu Leu Val
        35                  40                  45 tct ttt gca aaa acc tta gca gaa ggt gtg cca tca agg ttc agt ggc   192
Ser Phe Ala Lys Thr Leu Ala Glu Gly Val Pro Ser Arg Phe Ser Gly
    50                  55                  60 agt gga tca ggc aca cag ttt tct ctg aag atc agc agc ctg cag cct   240
Ser Gly Ser Gly Thr Gln Phe Ser Leu Lys Ile Ser Ser Leu Gln Pro
65                  70                  75                  80 gaa gat tct gga agt tat ttc tgt caa cat cat tcc gat aat ccg tgg   288
Glu Asp Ser Gly Ser Tyr Phe Cys Gln His His Ser Asp Asn Pro Trp
                85                  90                  95 acg ttc ggt gga ggc acc gaa ctg gag atc aaa cga                   324
Thr Phe Gly Gly Gly Thr Glu Leu Glu Ile Lys Arg
            100                 105

<210> SEQ ID NO 4
<211> LENGTH: 108
<212> TYPE: PRT
<213> ORGANISM: Mus musculus

<400> SEQUENCE: 4

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Arg
            100                 105
```

<210> SEQ ID NO 5
<211> LENGTH: 348
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(348)

<400> SEQUENCE: 5

```
gcc gtg cag ctg gtg cag agc gga gcc gag gtg aag aag ccc ggc agc     48
Ala Val Gln Leu Val Gln Ser Gly Ala Glu Val Lys Lys Pro Gly Ser
1               5                   10                  15 agc gtc aag gtg tcc tgc aag gcc agc ggc tac agc ttc acc ggc tac     96
Ser Val Lys Val Ser Cys Lys Ala Ser Gly Tyr Ser Phe Thr Gly Tyr
            20                  25                  30 aac atg aac tgg gtg cgg cag gcc cca ggc cag gga ctg gaa tgg atg    144
Asn Met Asn Trp Val Arg Gln Ala Pro Gly Gln Gly Leu Glu Trp Met
        35                  40                  45 ggc aac atc gac ccc tac tac ggc ggc acc acc tac aac cgg aag ttc    192
Gly Asn Ile Asp Pro Tyr Tyr Gly Gly Thr Thr Tyr Asn Arg Lys Phe
    50                  55                  60 aag ggc cgg gtg acc ctg acc gtg gac aag agc agc agc acc gcc tac    240
Lys Gly Arg Val Thr Leu Thr Val Asp Lys Ser Ser Ser Thr Ala Tyr
65                  70                  75                  80 atg gaa ctg agc agc ctg cgg agc gag gac acc gcc gtg tac tac tgc    288
Met Glu Leu Ser Ser Leu Arg Ser Glu Asp Thr Ala Val Tyr Tyr Cys
                85                  90                  95 gcc aga tcc gtg ggc ccc atg gac tac tgg ggc cag ggc acc ctg gtc    336
Ala Arg Ser Val Gly Pro Met Asp Tyr Trp Gly Gln Gly Thr Leu Val
            100                 105                 110 acc gtc tct tca                                                    348
Thr Val Ser Ser
        115
```

<210> SEQ ID NO 6
<211> LENGTH: 116
<212> TYPE: PRT
<213> ORGANISM: Artificial
<220> FEATURE:
<223> OTHER INFORMATION: Synthetic Construct

<400> SEQUENCE: 6

```
Ala Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Gly Thr Thr Tyr Asn Arg Lys Phe
    50                  55                  60

Lys Gly Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser
        115
```

<210> SEQ ID NO 7
<211> LENGTH: 348
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(348)

<400> SEQUENCE: 7

```
gcc gtg cag ctg gtc gag tct ggc ggc gga ctg gtg cag cct ggc ggc      48
Ala Val Gln Leu Val Glu Ser Gly Gly Gly Leu Val Gln Pro Gly Gly
1               5                   10                  15 agc ctg aga ctg agc tgc aag gcc agc ggc tac agc ttc acc ggc tac      96
Ser Leu Arg Leu Ser Cys Lys Ala Ser Gly Tyr Ser Phe Thr Gly Tyr
            20                  25                  30 aac atg aac tgg gtg cgg cag gcc cct ggc aag ggc ctg gaa tgg gtg     144
Asn Met Asn Trp Val Arg Gln Ala Pro Gly Lys Gly Leu Glu Trp Val
        35                  40                  45 ggc aac atc gac ccc tac tac ggc ggc acc acc tac aac cgg aag ttc     192
Gly Asn Ile Asp Pro Tyr Tyr Gly Gly Thr Thr Tyr Asn Arg Lys Phe
    50                  55                  60 aag ggc agg gcc acc ctg agc gtg gac aag agc agc agc acc gcc tac     240
Lys Gly Arg Ala Thr Leu Ser Val Asp Lys Ser Ser Ser Thr Ala Tyr
65                  70                  75                  80 ctg cag atg aac agc ctg cgg gcc gag gac acc gcc gtg tac tac tgc     288
Leu Gln Met Asn Ser Leu Arg Ala Glu Asp Thr Ala Val Tyr Tyr Cys
                85                  90                  95 gcc aga tcc gtg ggc ccc atg gac tac tgg ggc cag ggc acc ctg gtc     336
Ala Arg Ser Val Gly Pro Met Asp Tyr Trp Gly Gln Gly Thr Leu Val
            100                 105                 110 acc gtc tct tca                                                     348
Thr Val Ser Ser
        115
```

<210> SEQ ID NO 8
<211> LENGTH: 116
<212> TYPE: PRT
<213> ORGANISM: Artificial
<220> FEATURE:
<223> OTHER INFORMATION: Synthetic Construct

<400> SEQUENCE: 8

```
Ala Val Gln Leu Val Glu Ser Gly Gly Gly Leu Val Gln Pro Gly Gly
1               5                   10                  15

Ser Leu Arg Leu Ser Cys Lys Ala Ser Gly Tyr Ser Phe Thr Gly Tyr
            20                  25                  30

Asn Met Asn Trp Val Arg Gln Ala Pro Gly Lys Gly Leu Glu Trp Val
        35                  40                  45

Gly Asn Ile Asp Pro Tyr Tyr Gly Gly Thr Thr Tyr Asn Arg Lys Phe
    50                  55                  60

Lys Gly Arg Ala Thr Leu Ser Val Asp Lys Ser Ser Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser
        115
```

<210> SEQ ID NO 9
<211> LENGTH: 348
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(348)

<400> SEQUENCE: 9

```
gcc gtg cag ctg gtc gag tct ggc ggc gga ctg gtg cag cct ggc ggc        48
Ala Val Gln Leu Val Glu Ser Gly Gly Gly Leu Val Gln Pro Gly Gly
1               5                   10                  15 agc ctg aga ctg agc tgc aag gcc agc ggc tac agc ttc acc ggc tac        96
Ser Leu Arg Leu Ser Cys Lys Ala Ser Gly Tyr Ser Phe Thr Gly Tyr
            20                  25                  30 aac atg aac tgg gtg cgg cag gcc cct ggc aag ggc ctg gaa tgg gtg       144
Asn Met Asn Trp Val Arg Gln Ala Pro Gly Lys Gly Leu Glu Trp Val
        35                  40                  45 gcc aac atc gac ccc tac tac ggc ggc acc acc tac aac cgg aag gtc       192
Ala Asn Ile Asp Pro Tyr Tyr Gly Gly Thr Thr Tyr Asn Arg Lys Val
    50                  55                  60 aag ggc agg ttc acc atc agc gtg gac aag agc agc agc acc gcc tac       240
Lys Gly Arg Phe Thr Ile Ser Val Asp Lys Ser Ser Ser Thr Ala Tyr
65                  70                  75                  80 ctg cag atg aac agc ctg cgg gcc gag gac acc gcc gtg tac tac tgc       288
Leu Gln Met Asn Ser Leu Arg Ala Glu Asp Thr Ala Val Tyr Tyr Cys
                85                  90                  95 gcc aga tcc gtg ggc ccc atg gac tac tgg ggc cag ggc acc ctg gtc       336
Ala Arg Ser Val Gly Pro Met Asp Tyr Trp Gly Gln Gly Thr Leu Val
            100                 105                 110 acc gtc tct tca                                                       348
Thr Val Ser Ser
            115
```

<210> SEQ ID NO 10
<211> LENGTH: 116
<212> TYPE: PRT
<213> ORGANISM: Artificial
<220> FEATURE:
<223> OTHER INFORMATION: Synthetic Construct

<400> SEQUENCE: 10

```
Ala Val Gln Leu Val Glu Ser Gly Gly Gly Leu Val Gln Pro Gly Gly
1               5                   10                  15

Ser Leu Arg Leu Ser Cys Lys Ala Ser Gly Tyr Ser Phe Thr Gly Tyr
            20                  25                  30

Asn Met Asn Trp Val Arg Gln Ala Pro Gly Lys Gly Leu Glu Trp Val
        35                  40                  45

Ala Asn Ile Asp Pro Tyr Tyr Gly Gly Thr Thr Tyr Asn Arg Lys Val
    50                  55                  60

Lys Gly Arg Phe Thr Ile Ser Val Asp Lys Ser Ser Ser Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110

Thr Val Ser Ser
            115
```

<210> SEQ ID NO 11
<211> LENGTH: 324
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(324)

<400> SEQUENCE: 11

```
gac atc cag atg acc cag agc ccc agc agc ctg agc gcc agc gtg ggc     48
Asp Ile Gln Met Thr Gln Ser Pro Ser Ser Leu Ser Ala Ser Val Gly
1               5                   10                  15 gac cgg gtg acc atc acc tgc cgg acc agc gag aac gtg tac agc tac     96
Asp Arg Val Thr Ile Thr Cys Arg Thr Ser Glu Asn Val Tyr Ser Tyr
            20                  25                  30 ctg gcc tgg tat cag cag aag ccc ggc aag gcc ccc aag ctg ctg gtg    144
Leu Ala Trp Tyr Gln Gln Lys Pro Gly Lys Ala Pro Lys Leu Leu Val
        35                  40                  45 tcc ttc gcc aag acc ctg gcc gag ggc gtg ccc agc cgg ttt agc ggc    192
Ser Phe Ala Lys Thr Leu Ala Glu Gly Val Pro Ser Arg Phe Ser Gly
50                  55                  60 agc ggc tcc ggc acc gac ttc acc ctg acc atc agc agc ctg cag ccc    240
Ser Gly Ser Gly Thr Asp Phe Thr Leu Thr Ile Ser Ser Leu Gln Pro
65                  70                  75                  80 gag gac ttc gcc acc tac ttt tgc cag cac cac agc gac aac ccc tgg    288
Glu Asp Phe Ala Thr Tyr Phe Cys Gln His His Ser Asp Asn Pro Trp
                85                  90                  95 acc ttc ggc cag ggc acc aag gtg gag atc aaa cgt                    324
Thr Phe Gly Gln Gly Thr Lys Val Glu Ile Lys Arg
            100                 105
```

<210> SEQ ID NO 12
<211> LENGTH: 108
<212> TYPE: PRT
<213> ORGANISM: Artificial
<220> FEATURE:
<223> OTHER INFORMATION: Synthetic Construct

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
        35                  40                  45

Ser Phe Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His His Ser Asp Asn Pro Trp
                85                  90                  95

Thr Phe Gly Gln Gly Thr Lys Val Glu Ile Lys Arg
            100                 105
```

<210> SEQ ID NO 13
<211> LENGTH: 324
<212> TYPE: DNA
<213> ORGANISM: Artificial
<220> FEATURE:
<223> OTHER INFORMATION: Humanized murine immunoglobulin sequence

<220> FEATURE:
<221> NAME/KEY: CDS
<222> LOCATION: (1)..(324)

<400> SEQUENCE: 13

```
gac atc gtg atg acc cag agc ccc agc agc ctg agc gcc agc gtg ggc    48
Asp Ile Val Met Thr Gln Ser Pro Ser Ser Leu Ser Ala Ser Val Gly
1               5                   10                  15 gac cgg gtg acc atc acc tgc cgg gtc agc gag aac gtg tac agc tac    96
Asp Arg Val Thr Ile Thr Cys Arg Val Ser Glu Asn Val Tyr Ser Tyr
            20                  25                  30 ctg gcc tgg tat cag cag aag ccc ggc aag gcc ccc aag ctg ctg atc   144
Leu Ala Trp Tyr Gln Gln Lys Pro Gly Lys Ala Pro Lys Leu Leu Ile
        35                  40                  45 tcc ttc gcc aag acc ctg gcc gag ggc gtg ccc agc cgg ttt agc ggc   192
Ser Phe Ala Lys Thr Leu Ala Glu Gly Val Pro Ser Arg Phe Ser Gly
50                  55                  60 agc ggc tcc ggc acc gac ttc acc ctg acc atc agc agc ctg cag ccc   240
Ser Gly Ser Gly Thr Asp Phe Thr Leu Thr Ile Ser Ser Leu Gln Pro
65                  70                  75                  80 gag gac ttc gcc acc tac ttt tgc cag cac cac agc gac aac ccc tgg   288
Glu Asp Phe Ala Thr Tyr Phe Cys Gln His His Ser Asp Asn Pro Trp
                85                  90                  95 acc ttc ggc cag ggc acc aag gtg gag atc aaa cgt                   324
Thr Phe Gly Gln Gly Thr Lys Val Glu Ile Lys Arg
            100                 105
```

<210> SEQ ID NO 14
<211> LENGTH: 108
<212> TYPE: PRT
<213> ORGANISM: Artificial
<220> FEATURE:
<223> OTHER INFORMATION: Synthetic Construct

<400> SEQUENCE: 14

```
Asp Ile Val Met Thr Gln Ser Pro Ser Ser Leu Ser Ala Ser Val Gly
1               5                   10                  15

Asp Arg Val Thr Ile Thr Cys Arg Val Ser Glu Asn Val Tyr Ser Tyr
            20                  25                  30

Leu Ala Trp Tyr Gln Gln Lys Pro Gly Lys Ala Pro Lys Leu Leu Ile
        35                  40                  45

Ser Phe Ala Lys Thr Leu Ala Glu Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His His Ser Asp Asn Pro Trp
                85                  90                  95

Thr Phe Gly Gln Gly Thr Lys Val Glu Ile Lys Arg
            100                 105
```

<210> SEQ ID NO 15
<211> LENGTH: 324
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(324)

<400> SEQUENCE: 15

```
gac atc cag atg acc cag agc ccc agc agc ctg agc gcc agc gtg ggc    48
```

```
Asp Ile Gln Met Thr Gln Ser Pro Ser Ser Leu Ser Ala Ser Val Gly
1               5                   10                  15 gac cgg gtg acc atc acc tgc cgg acc agc gag aac gtg tac agc tac      96
Asp Arg Val Thr Ile Thr Cys Arg Thr Ser Glu Asn Val Tyr Ser Tyr
                20                  25                  30 ctg gcc tgg tat cag cag aag ccc ggc aag gcc ccc aag ctg ctg gtg     144
Leu Ala Trp Tyr Gln Gln Lys Pro Gly Lys Ala Pro Lys Leu Leu Val
            35                  40                  45 tcc ttc gcc aag acc ctg gcc gag ggc gtg ccc agc cgg ttt agc ggc     192
Ser Phe Ala Lys Thr Leu Ala Glu Gly Val Pro Ser Arg Phe Ser Gly
        50                  55                  60 agc ggc tcc ggc acc cag ttc acc ctg acc atc agc agc ctg cag ccc     240
Ser Gly Ser Gly Thr Gln Phe Thr Leu Thr Ile Ser Ser Leu Gln Pro
65                  70                  75                  80 gag gac ttc gcc acc tac ttt tgc cag cac cac agc gac aac ccc tgg     288
Glu Asp Phe Ala Thr Tyr Phe Cys Gln His His Ser Asp Asn Pro Trp
                85                  90                  95 acc ttc ggc gga ggc acc gag ctg gag atc aaa cgt                     324
Thr Phe Gly Gly Gly Thr Glu Leu Glu Ile Lys Arg
                100                 105

<210> SEQ ID NO 16
<211> LENGTH: 108
<212> TYPE: PRT
<213> ORGANISM: Artificial
<220> FEATURE:
<223> OTHER INFORMATION: Synthetic Construct

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
                20                  25                  30

Leu Ala Trp Tyr Gln Gln Lys Pro Gly Lys Ala Pro Lys Leu Leu Val
            35                  40                  45

Ser Phe Ala Lys Thr Leu Ala Glu Gly Val Pro Ser Arg Phe Ser Gly
        50                  55                  60

Ser Gly Ser Gly Thr Gln Phe Thr Leu Thr Ile Ser Ser Leu Gln Pro
65                  70                  75                  80

Glu Asp Phe Ala Thr Tyr Phe Cys Gln His His Ser Asp Asn Pro Trp
                85                  90                  95

Thr Phe Gly Gly Gly Thr Glu Leu Glu Ile Lys Arg
                100                 105

<210> SEQ ID NO 17
<211> LENGTH: 324
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(324)

<400> SEQUENCE: 17 gac atc gtg atg acc cag agc ccc gcc acc ctg agc ctg agc cct ggc      48
Asp Ile Val Met Thr Gln Ser Pro Ala Thr Leu Ser Leu Ser Pro Gly
1               5                   10                  15 gag cgg gcc acc ctg tcc tgc cgg acc agc gag aac gtg tac agc tac      96
Glu Arg Ala Thr Leu Ser Cys Arg Thr Ser Glu Asn Val Tyr Ser Tyr
                20                  25                  30
```

```
ctg gcc tgg tat cag cag aag ccc ggc cag gcc ccc aga ctg ctg gtg      144
Leu Ala Trp Tyr Gln Gln Lys Pro Gly Gln Ala Pro Arg Leu Leu Val
        35                  40                  45 tcc ttc gcc aag acc ctg gcc gag ggc gtg ccc gcc agg ttt agc ggc      192
Ser Phe Ala Lys Thr Leu Ala Glu Gly Val Pro Ala Arg Phe Ser Gly
 50                  55                  60 agc ggc tcc ggc acc gac ttc acc ctg acc atc agc agc ctg gaa ccc      240
Ser Gly Ser Gly Thr Asp Phe Thr Leu Thr Ile Ser Ser Leu Glu Pro
 65                  70                  75                  80 gag gac ttc gcc gtg tac ttc tgc cag cac cac agc gac aac ccc tgg      288
Glu Asp Phe Ala Val Tyr Phe Cys Gln His His Ser Asp Asn Pro Trp
                 85                  90                  95 acc ttc ggc cag ggc acc aag gtg gag atc aaa cgt                      324
Thr Phe Gly Gln Gly Thr Lys Val Glu Ile Lys Arg
                100                 105

<210> SEQ ID NO 18
<211> LENGTH: 108
<212> TYPE: PRT
<213> ORGANISM: Artificial
<220> FEATURE:
<223> OTHER INFORMATION: Synthetic Construct

<400> SEQUENCE: 18

Asp Ile Val Met Thr Gln Ser Pro Ala Thr Leu Ser Leu Ser Pro Gly
1               5                   10                  15

Glu Arg Ala Thr Leu Ser Cys Arg Thr Ser Glu Asn Val Tyr Ser Tyr
            20                  25                  30

Leu Ala Trp Tyr Gln Gln Lys Pro Gly Gln Ala Pro Arg Leu Leu Val
        35                  40                  45

Ser Phe Ala Lys Thr Leu Ala Glu Gly Val Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Phe Cys Gln His His Ser Asp Asn Pro Trp
                 85                  90                  95

Thr Phe Gly Gln Gly Thr Lys Val Glu Ile Lys Arg
                100                 105

<210> SEQ ID NO 19
<211> LENGTH: 324
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(324)

<400> SEQUENCE: 19 gac atc gtg atg acc cag agc ccc gcc acc ctg agc ctg agc cct ggc       48
Asp Ile Val Met Thr Gln Ser Pro Ala Thr Leu Ser Leu Ser Pro Gly
1               5                   10                  15 gag cgg gcc acc ctg tcc tgc cgg gtc agc gag aac gtg tac agc tac       96
Glu Arg Ala Thr Leu Ser Cys Arg Val Ser Glu Asn Val Tyr Ser Tyr
            20                  25                  30 ctg gcc tgg tat cag cag aag ccc ggc cag gcc ccc aga ctg ctg atc      144
Leu Ala Trp Tyr Gln Gln Lys Pro Gly Gln Ala Pro Arg Leu Leu Ile
        35                  40                  45 tcc ttc gcc aag acc ctg gcc gag ggc gtg ccc gcc agg ttt agc ggc      192
Ser Phe Ala Lys Thr Leu Ala Glu Gly Val Pro Ala Arg Phe Ser Gly
 50                  55                  60
```

```
agc ggc tcc ggc acc gac ttc acc ctg acc atc agc agc ctg gaa ccc      240
Ser Gly Ser Gly Thr Asp Phe Thr Leu Thr Ile Ser Ser Leu Glu Pro
 65                  70                  75                  80 gag gac ttc gcc gtg tac ttc tgc cag cac cac agc gac aac ccc tgg      288
Glu Asp Phe Ala Val Tyr Phe Cys Gln His His Ser Asp Asn Pro Trp
                 85                  90                  95 acc ttc ggc cag ggc acc aag gtg gag atc aaa cgt                      324
Thr Phe Gly Gln Gly Thr Lys Val Glu Ile Lys Arg
                100                 105
```

<210> SEQ ID NO 20
<211> LENGTH: 108
<212> TYPE: PRT
<213> ORGANISM: Artificial
<220> FEATURE:
<223> OTHER INFORMATION: Synthetic Construct

<400> SEQUENCE: 20

```
Asp Ile Val Met Thr Gln Ser Pro Ala Thr Leu Ser Leu Ser Pro Gly
  1               5                  10                  15

Glu Arg Ala Thr Leu Ser Cys Arg Val Ser Glu Asn Val Tyr Ser Tyr
                 20                  25                  30

Leu Ala Trp Tyr Gln Gln Lys Pro Gly Gln Ala Pro Arg Leu Leu Ile
             35                  40                  45

Ser Phe Ala Lys Thr Leu Ala Glu Gly Val Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Phe Cys Gln His His Ser Asp Asn Pro Trp
                 85                  90                  95

Thr Phe Gly Gln Gly Thr Lys Val Glu Ile Lys Arg
                100                 105
```

<210> SEQ ID NO 21
<211> LENGTH: 324
<212> TYPE: DNA
<213> ORGANISM: Artificial
<220> FEATURE:
<223> OTHER INFORMATION: Humanized murine immunoglobulin sequence
<220> FEATURE:
<221> NAME/KEY: CDS
<222> LOCATION: (1)..(324)

<400> SEQUENCE: 21

```
gac atc gtg atg acc cag agc ccc gcc acc ctg agc ctg agc cct ggc       48
Asp Ile Val Met Thr Gln Ser Pro Ala Thr Leu Ser Leu Ser Pro Gly
  1               5                  10                  15 gag cgg gcc acc ctg tcc tgc cgg acc agc gag aac gtg tac agc tac       96
Glu Arg Ala Thr Leu Ser Cys Arg Thr Ser Glu Asn Val Tyr Ser Tyr
                 20                  25                  30 ctg gcc tgg tat cag cag aag ccc ggc cag gcc ccc aga ctg ctg gtg      144
Leu Ala Trp Tyr Gln Gln Lys Pro Gly Gln Ala Pro Arg Leu Leu Val
             35                  40                  45 tcc ttc gcc aag acc ctg gcc gag ggc gtg ccc gcc agg ttt agc ggc      192
Ser Phe Ala Lys Thr Leu Ala Glu Gly Val Pro Ala Arg Phe Ser Gly
 50                  55                  60 agc ggc tcc ggc acc cag ttc acc ctg acc atc agc agc ctg gaa ccc      240
Ser Gly Ser Gly Thr Gln Phe Thr Leu Thr Ile Ser Ser Leu Glu Pro
 65                  70                  75                  80 gag gac ttc gcc gtg tac ttc tgc cag cac cac agc gac aac ccc tgg      288
Glu Asp Phe Ala Val Tyr Phe Cys Gln His His Ser Asp Asn Pro Trp
                 85                  90                  95
```

```
                        85                  90                  95
acc ttc ggc gga ggc acc gag ctg gag atc aaa cgt                         324
Thr Phe Gly Gly Gly Thr Glu Leu Glu Ile Lys Arg
                100                 105

<210> SEQ ID NO 22
<211> LENGTH: 108
<212> TYPE: PRT
<213> ORGANISM: Artificial
<220> FEATURE:
<223> OTHER INFORMATION: Synthetic Construct

<400> SEQUENCE: 22

Asp Ile Val Met Thr Gln Ser Pro Ala Thr Leu Ser Leu Ser Pro Gly
1               5                   10                  15

Glu Arg Ala Thr Leu Ser Cys Arg Thr Ser Glu Asn Val Tyr Ser Tyr
            20                  25                  30

Leu Ala Trp Tyr Gln Gln Lys Pro Gly Gln Ala Pro Arg Leu Leu Val
        35                  40                  45

Ser Phe Ala Lys Thr Leu Ala Glu Gly Val Pro Ala Arg Phe Ser Gly
    50                  55                  60

Ser Gly Ser Gly Thr Gln Phe Thr Leu Thr Ile Ser Ser Leu Glu Pro
65                  70                  75                  80

Glu Asp Phe Ala Val Tyr Phe Cys Gln His His Ser Asp Asn Pro Trp
                85                  90                  95

Thr Phe Gly Gly Gly Thr Glu Leu Glu Ile Lys Arg
                100                 105

<210> SEQ ID NO 23
<211> LENGTH: 990
<212> TYPE: DNA
<213> ORGANISM: Homo sapiens
<220> FEATURE:
<221> NAME/KEY: CDS
<222> LOCATION: (1)..(990)

<400> SEQUENCE: 23 gcc tcc acc aag ggc cca tcg gtc ttc ccc ctg gca ccc tcc tcc aag       48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac       96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aga gtt gag ccc aaa tct tgt gac aaa act cac aca tgc cca ccg tgc      336
Arg Val Glu Pro Lys Ser Cys Asp Lys Thr His Thr Cys Pro Pro Cys
                100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
            115                 120                 125
```

```
aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
Val Val Val Asp Val Ser His Glu Asp Pro Glu Val Lys Phe Asn Trp
145                 150                 155                 160 tac gtg gac ggc gtg gag gtg cat aat gcc aag aca aag ccg cgg gag      528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg      576
Glu Gln Tyr Asn Ser Thr Tyr Arg Val Val Ser Val Leu Thr Val Leu
            180                 185                 190 cac cag gac tgg ctg aat ggc aag gag tac aag tgc aag gtc tcc aac      624
His Gln Asp Trp Leu Asn Gly Lys Glu Tyr Lys Cys Lys Val Ser Asn
        195                 200                 205 aaa gcc ctc cca gcc ccc atc gag aaa acc atc tcc aaa gcc aaa ggg      672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag      720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat      768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac      816
Pro Ser Asp Ile Ala Val Glu Trp Glu Ser Asn Gly Gln Pro Glu Asn
                260                 265                 270 aac tac aag acc acg cct ccc gtg ctg gac tcc gac ggc tcc ttc ttc      864
Asn Tyr Lys Thr Thr Pro Pro Val Leu Asp Ser Asp Gly Ser Phe Phe
            275                 280                 285 ctc tat agc aag ctc acc gtg gac aag agc agg tgg cag cag ggg aac      912
Leu Tyr Ser Lys Leu Thr Val Asp Lys Ser Arg Trp Gln Gln Gly Asn
        290                 295                 300 gtc ttc tca tgc tcc gtg atg cat gag gct ctg cac aac cac tac acg      960
Val Phe Ser Cys Ser Val Met His Glu Ala Leu His Asn His Tyr Thr
305                 310                 315                 320 cag aag agc ctc tcc ctg tcc ccg ggt aaa                              990
Gln Lys Ser Leu Ser Leu Ser Pro Gly Lys
                325                 330

<210> SEQ ID NO 24
<211> LENGTH: 330
<212> TYPE: PRT
<213> ORGANISM: Homo sapiens

<400> SEQUENCE: 24

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 25
<211> LENGTH: 318
<212> TYPE: DNA
<213> ORGANISM: Homo sapiens
<220> FEATURE:
<221> NAME/KEY: CDS
<222> LOCATION: (1)..(318)

<400> SEQUENCE: 25 act gtg gct gca cca tct gtc ttc atc ttc ccg cca tct gat gag cag      48
Thr Val Ala Ala Pro Ser Val Phe Ile Phe Pro Pro Ser Asp Glu Gln
1               5                   10                  15 ttg aaa tct gga act gcc tct gtt gtg tgc ctg ctg aat aac ttc tat      96
Leu Lys Ser Gly Thr Ala Ser Val Val Cys Leu Leu Asn Asn Phe Tyr
            20                  25                  30 ccc aga gag gcc aaa gta cag tgg aag gtg gat aac gcc ctc caa tcg     144
Pro Arg Glu Ala Lys Val Gln Trp Lys Val Asp Asn Ala Leu Gln Ser
        35                  40                  45 ggt aac tcc cag gag agt gtc aca gag cag gac agc aag gac agc acc     192
Gly Asn Ser Gln Glu Ser Val Thr Glu Gln Asp Ser Lys Asp Ser Thr
    50                  55                  60 tac agc ctc agc agc acc ctg acg ctg agc aaa gca gac tac gag aaa     240
Tyr Ser Leu Ser Ser Thr Leu Thr Leu Ser Lys Ala Asp Tyr Glu Lys
65                  70                  75                  80 cac aaa gtc tac gcc tgc gaa gtc acc cat cag ggc ctg agc tcg ccc     288
His Lys Val Tyr Ala Cys Glu Val Thr His Gln Gly Leu Ser Ser Pro
                85                  90                  95
```

```
gtc aca aag agc ttc aac agg gga gag tgt                              318
Val Thr Lys Ser Phe Asn Arg Gly Glu Cys
            100                 105

<210> SEQ ID NO 26
<211> LENGTH: 106
<212> TYPE: PRT
<213> ORGANISM: Homo sapiens

<400> SEQUENCE: 26

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 27
<211> LENGTH: 1338
<212> TYPE: DNA
<213> ORGANISM: Artificial
<220> FEATURE:
<223> OTHER INFORMATION: Fc-engineered chimeric immunoglobulin sequence
<220> FEATURE:
<221> NAME/KEY: CDS
<222> LOCATION: (1)..(1338)

<400> SEQUENCE: 27 gcg gtc cag ctg cag cag tct gga cct gag ctg gaa aag cct ggc gct      48
Ala Val Gln Leu Gln Gln Ser Gly Pro Glu Leu Glu Lys Pro Gly Ala
1               5                   10                  15 tca gtg aag att tcc tgc aag gct tct ggt tac tca ttc act ggc tac      96
Ser Val Lys Ile Ser Cys Lys Ala Ser Gly Tyr Ser Phe Thr Gly Tyr
            20                  25                  30 aat atg aac tgg gtg aag cag aat aat gga aag agc ctt gag tgg att     144
Asn Met Asn Trp Val Lys Gln Asn Asn Gly Lys Ser Leu Glu Trp Ile
        35                  40                  45 gga aat att gat cct tat tat ggt ggt act acc tac aac cgg aag ttc     192
Gly Asn Ile Asp Pro Tyr Tyr Gly Gly Thr Thr Tyr Asn Arg Lys Phe
    50                  55                  60 aag ggc aag gcc aca ttg act gta gac aaa tcc tcc agc aca gcc tac     240
Lys Gly Lys Ala Thr Leu Thr Val Asp Lys Ser Ser Ser Thr Ala Tyr
65                  70                  75                  80 atg cag ctc aag agt ctg aca tct gag gac tct gca gtc tat tac tgt     288
Met Gln Leu Lys Ser Leu Thr Ser Glu Asp Ser Ala Val Tyr Tyr Cys
                85                  90                  95 gca aga tcg gtc ggc cct atg gac tac tgg ggt caa gga acc tca gtc     336
Ala Arg Ser Val Gly Pro Met Asp Tyr Trp Gly Gln Gly Thr Ser Val
            100                 105                 110 acc gtc tct tca gcc tcc acc aag ggc cca tcg gtc ttc ccc ctg gca     384
Thr Val Ser Ser Ala Ser Thr Lys Gly Pro Ser Val Phe Pro Leu Ala
        115                 120                 125
```

```
ccc tcc tcc aag agc acc tct ggg ggc aca gcg gcc ctg ggc tgc ctg        432
Pro Ser Ser Lys Ser Thr Ser Gly Gly Thr Ala Ala Leu Gly Cys Leu
130                 135                 140 gtc aag gac tac ttc ccc gaa ccg gtg acg gtg tcg tgg aac tca ggc        480
Val Lys Asp Tyr Phe Pro Glu Pro Val Thr Val Ser Trp Asn Ser Gly
145                 150                 155                 160 gcc ctg acc agc ggc gtg cac acc ttc ccg gct gtc cta cag tcc tca        528
Ala Leu Thr Ser Gly Val His Thr Phe Pro Ala Val Leu Gln Ser Ser
            165                 170                 175 gga ctc tac tcc ctc agc agc gtg gtg acc gtg ccc tcc agc agc ttg        576
Gly Leu Tyr Ser Leu Ser Ser Val Val Thr Val Pro Ser Ser Ser Leu
        180                 185                 190 ggc acc cag acc tac atc tgc aac gtg aat cac aag ccc agc aac acc        624
Gly Thr Gln Thr Tyr Ile Cys Asn Val Asn His Lys Pro Ser Asn Thr
    195                 200                 205 aag gtg gac aag aga gtt gag ccc aaa tct tgt gac aaa act cac aca        672
Lys Val Asp Lys Arg Val Glu Pro Lys Ser Cys Asp Lys Thr His Thr
210                 215                 220 tgc cca ccg tgc cca gca cct gaa ctc ctg ggg gga ccg gac gtc ttc        720
Cys Pro Pro Cys Pro Ala Pro Glu Leu Leu Gly Gly Pro Asp Val Phe
225                 230                 235                 240 ctc ttc ccc cca aaa ccc aag gac acc ctc atg atc tcc cgg acc cct        768
Leu Phe Pro Pro Lys Pro Lys Asp Thr Leu Met Ile Ser Arg Thr Pro
            245                 250                 255 gag gtc aca tgc gtg gtg gtg gac gtg agc cac gaa gac cct gag gtc        816
Glu Val Thr Cys Val Val Val Asp Val Ser His Glu Asp Pro Glu Val
        260                 265                 270 aag ttc aac tgg tac gtg gac ggc gtg gag gtg cat aat gcc aag aca        864
Lys Phe Asn Trp Tyr Val Asp Gly Val Glu Val His Asn Ala Lys Thr
    275                 280                 285 aag ccg cgg gag gag cag tac aac agc acg tac cgt gtg gtc agc gtc        912
Lys Pro Arg Glu Glu Gln Tyr Asn Ser Thr Tyr Arg Val Val Ser Val
290                 295                 300 ctc acc gtc ctg cac cag gac tgg ctg aat ggc aag gag tac aag tgc        960
Leu Thr Val Leu His Gln Asp Trp Leu Asn Gly Lys Glu Tyr Lys Cys
305                 310                 315                 320 aag gtc tcc aac aaa gcc ctc cca gcc ccc gaa gag aaa acc atc tcc       1008
Lys Val Ser Asn Lys Ala Leu Pro Ala Pro Glu Glu Lys Thr Ile Ser
            325                 330                 335 aaa gcc aaa ggg cag ccc cga gaa cca cag gtg tac acc ctg ccc cca       1056
Lys Ala Lys Gly Gln Pro Arg Glu Pro Gln Val Tyr Thr Leu Pro Pro
        340                 345                 350 tcc cgg gag gag atg acc aag aac cag gtc agc ctg acc tgc ctg gtc       1104
Ser Arg Glu Glu Met Thr Lys Asn Gln Val Ser Leu Thr Cys Leu Val
    355                 360                 365 aaa ggc ttc tat ccc agc gac atc gcc gtg gag tgg gag agc aat ggg       1152
Lys Gly Phe Tyr Pro Ser Asp Ile Ala Val Glu Trp Glu Ser Asn Gly
370                 375                 380 cag ccg gag aac aac tac aag acc acg cct ccc gtg ctg gac tcc gac       1200
Gln Pro Glu Asn Asn Tyr Lys Thr Thr Pro Pro Val Leu Asp Ser Asp
385                 390                 395                 400 ggc tcc ttc ttc ctc tat agc aag ctc acc gtg gac aag agc agg tgg       1248
Gly Ser Phe Phe Leu Tyr Ser Lys Leu Thr Val Asp Lys Ser Arg Trp
            405                 410                 415 cag cag ggg aac gtc ttc tca tgc tcc gtg atg cat gag gct ctg cac       1296
Gln Gln Gly Asn Val Phe Ser Cys Ser Val Met His Glu Ala Leu His
        420                 425                 430 aac cac tac acg cag aag agc ctc tcc ctg tcc ccg ggt aaa               1338
Asn His Tyr Thr Gln Lys Ser Leu Ser Leu Ser Pro Gly Lys
    435                 440                 445
```

<210> SEQ ID NO 28
<211> LENGTH: 446
<212> TYPE: PRT
<213> ORGANISM: Artificial
<220> FEATURE:
<223> OTHER INFORMATION: Synthetic Construct

<400> SEQUENCE: 28

```
Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
                85                  90                  95

Ala Arg Ser Val Gly Pro Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Asp Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 29
<211> LENGTH: 642
<212> TYPE: DNA
<213> ORGANISM: Artificial
<220> FEATURE:
<223> OTHER INFORMATION: Chimeric immunoglobulin sequence
<220> FEATURE:
<221> NAME/KEY: CDS
<222> LOCATION: (1)..(642)

<400> SEQUENCE: 29
```

| | | | | | | | | | | | | | | | | |
|---|---|---|---|---|---|---|---|---|---|---|---|---|---|---|---|---|
| gac | atc | cag | atg | act | cag | tct | cca | gcc | tcc | cta | tct | gca | tct | gtg | gga | 48 |
| Asp | Ile | Gln | Met | Thr | Gln | Ser | Pro | Ala | Ser | Leu | Ser | Ala | Ser | Val | Gly | |
| 1 | | | | 5 | | | | | 10 | | | | | 15 | | |
| gag | act | gtc | acc | atc | aca | tgt | cga | aca | agt | gaa | aat | gtt | tac | agt | tat | 96 |
| Glu | Thr | Val | Thr | Ile | Thr | Cys | Arg | Thr | Ser | Glu | Asn | Val | Tyr | Ser | Tyr | |
| | | | 20 | | | | | 25 | | | | | 30 | | | |
| ttg | gct | tgg | tat | cag | cag | aaa | cag | gga | aaa | tct | cct | cag | ctc | ctg | gtc | 144 |
| Leu | Ala | Trp | Tyr | Gln | Gln | Lys | Gln | Gly | Lys | Ser | Pro | Gln | Leu | Leu | Val | |
| | | 35 | | | | | 40 | | | | | 45 | | | | |
| tct | ttt | gca | aaa | acc | tta | gca | gaa | ggt | gtg | cca | tca | agg | ttc | agt | ggc | 192 |
| Ser | Phe | Ala | Lys | Thr | Leu | Ala | Glu | Gly | Val | Pro | Ser | Arg | Phe | Ser | Gly | |
| | 50 | | | | | 55 | | | | | 60 | | | | | |
| agt | gga | tca | ggc | aca | cag | ttt | tct | ctg | aag | atc | agc | agc | ctg | cag | cct | 240 |
| Ser | Gly | Ser | Gly | Thr | Gln | Phe | Ser | Leu | Lys | Ile | Ser | Ser | Leu | Gln | Pro | |
| 65 | | | | | 70 | | | | | 75 | | | | | 80 | |
| gaa | gat | tct | gga | agt | tat | ttc | tgt | caa | cat | cat | tcc | gat | aat | ccg | tgg | 288 |
| Glu | Asp | Ser | Gly | Ser | Tyr | Phe | Cys | Gln | His | His | Ser | Asp | Asn | Pro | Trp | |
| | | | | 85 | | | | | 90 | | | | | 95 | | |
| acg | ttc | ggt | gga | ggc | acc | gaa | ctg | gag | atc | aaa | cga | act | gtg | gct | gca | 336 |
| Thr | Phe | Gly | Gly | Gly | Thr | Glu | Leu | Glu | Ile | Lys | Arg | Thr | Val | Ala | Ala | |
| | | | 100 | | | | | 105 | | | | | 110 | | | |
| cca | tct | gtc | ttc | atc | ttc | ccg | cca | tct | gat | gag | cag | ttg | aaa | tct | gga | 384 |
| Pro | Ser | Val | Phe | Ile | Phe | Pro | Pro | Ser | Asp | Glu | Gln | Leu | Lys | Ser | Gly | |
| | | | 115 | | | | | 120 | | | | | 125 | | | |
| act | gcc | tct | gtt | gtg | tgc | ctg | ctg | aat | aac | ttc | tat | ccc | aga | gag | gcc | 432 |
| Thr | Ala | Ser | Val | Val | Cys | Leu | Leu | Asn | Asn | Phe | Tyr | Pro | Arg | Glu | Ala | |
| | | 130 | | | | | 135 | | | | | 140 | | | | |
| aaa | gta | cag | tgg | aag | gtg | gat | aac | gcc | ctc | caa | tcg | ggt | aac | tcc | cag | 480 |
| Lys | Val | Gln | Trp | Lys | Val | Asp | Asn | Ala | Leu | Gln | Ser | Gly | Asn | Ser | Gln | |
| 145 | | | | | 150 | | | | | 155 | | | | | 160 | |
| gag | agt | gtc | aca | gag | cag | gac | agc | aag | gac | agc | acc | tac | agc | ctc | agc | 528 |
| Glu | Ser | Val | Thr | Glu | Gln | Asp | Ser | Lys | Asp | Ser | Thr | Tyr | Ser | Leu | Ser | |
| | | | 165 | | | | | 170 | | | | | 175 | | | |
| agc | acc | ctg | acg | ctg | agc | aaa | gca | gac | tac | gag | aaa | cac | aaa | gtc | tac | 576 |
| Ser | Thr | Leu | Thr | Leu | Ser | Lys | Ala | Asp | Tyr | Glu | Lys | His | Lys | Val | Tyr | |
| | | | 180 | | | | | 185 | | | | | 190 | | | |
| gcc | tgc | gaa | gtc | acc | cat | cag | ggc | ctg | agc | tcg | ccc | gtc | aca | aag | agc | 624 |
| Ala | Cys | Glu | Val | Thr | His | Gln | Gly | Leu | Ser | Ser | Pro | Val | Thr | Lys | Ser | |

```
                195                 200                 205
ttc aac agg gga gag tgt                                              642
Phe Asn Arg Gly Glu Cys
    210

<210> SEQ ID NO 30
<211> LENGTH: 214
<212> TYPE: PRT
<213> ORGANISM: Artificial
<220> FEATURE:
<223> OTHER INFORMATION: Synthetic Construct

<400> SEQUENCE: 30

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 1338
<212> TYPE: DNA
<213> ORGANISM: Artificial
<220> FEATURE:
<223> OTHER INFORMATION: Fc-engineered chimeric immunoglobulin sequence
<220> FEATURE:
<221> NAME/KEY: CDS
<222> LOCATION: (1)..(1338)

<400> SEQUENCE: 31 gcg gtc cag ctg cag cag tct gga cct gag ctg gaa aag cct ggc gct    48
Ala Val Gln Leu Gln Gln Ser Gly Pro Glu Leu Glu Lys Pro Gly Ala
1               5                   10                  15 tca gtg aag att tcc tgc aag gct tct ggt tac tca ttc act ggc tac    96
Ser Val Lys Ile Ser Cys Lys Ala Ser Gly Tyr Ser Phe Thr Gly Tyr
            20                  25                  30
```

```
aat atg aac tgg gtg aag cag aat aat gga aag agc ctt gag tgg att      144
Asn Met Asn Trp Val Lys Gln Asn Asn Gly Lys Ser Leu Glu Trp Ile
     35                  40                  45 gga aat att gat cct tat tat ggt ggt act acc tac aac cgg aag ttc      192
Gly Asn Ile Asp Pro Tyr Tyr Gly Gly Thr Thr Tyr Asn Arg Lys Phe
 50                  55                  60 aag ggc aag gcc aca ttg act gta gac aaa tcc tcc agc aca gcc tac      240
Lys Gly Lys Ala Thr Leu Thr Val Asp Lys Ser Ser Ser Thr Ala Tyr
 65                  70                  75                  80 atg cag ctc aag agt ctg aca tct gag gac tct gca gtc tat tac tgt      288
Met Gln Leu Lys Ser Leu Thr Ser Glu Asp Ser Ala Val Tyr Tyr Cys
                 85                  90                  95 gca aga tcg gtc ggc cct atg gac tac tgg ggt caa gga acc tca gtc      336
Ala Arg Ser Val Gly Pro Met Asp Tyr Trp Gly Gln Gly Thr Ser Val
             100                 105                 110 acc gtc tct tca gcc tcc acc aag ggc cca tcg gtc ttc ccc ctg gca      384
Thr Val Ser Ser Ala Ser Thr Lys Gly Pro Ser Val Phe Pro Leu Ala
             115                 120                 125 ccc tcc tcc aag agc acc tct ggg ggc aca gcg gcc ctg ggc tgc ctg      432
Pro Ser Ser Lys Ser Thr Ser Gly Gly Thr Ala Ala Leu Gly Cys Leu
130                 135                 140 gtc aag gac tac ttc ccc gaa ccg gtg acg gtg tcg tgg aac tca ggc      480
Val Lys Asp Tyr Phe Pro Glu Pro Val Thr Val Ser Trp Asn Ser Gly
145                 150                 155                 160 gcc ctg acc agc ggc gtg cac acc ttc ccg gct gtc cta cag tcc tca      528
Ala Leu Thr Ser Gly Val His Thr Phe Pro Ala Val Leu Gln Ser Ser
                165                 170                 175 gga ctc tac tcc ctc agc agc gtg gtg acc gtg ccc tcc agc agc ttg      576
Gly Leu Tyr Ser Leu Ser Ser Val Val Thr Val Pro Ser Ser Ser Leu
            180                 185                 190 ggc acc cag acc tac atc tgc aac gtg aat cac aag ccc agc aac acc      624
Gly Thr Gln Thr Tyr Ile Cys Asn Val Asn His Lys Pro Ser Asn Thr
            195                 200                 205 aag gtg gac aag aga gtt gag ccc aaa tct tgt gac aaa act cac aca      672
Lys Val Asp Lys Arg Val Glu Pro Lys Ser Cys Asp Lys Thr His Thr
210                 215                 220 tgc cca ccg tgc cca gca cct gaa ctc ctg gcg gga ccg gat gtc ttc      720
Cys Pro Pro Cys Pro Ala Pro Glu Leu Leu Ala Gly Pro Asp Val Phe
225                 230                 235                 240 ctc ttc ccc cca aaa ccc aag gac acc ctc atg atc tcc cgg acc cct      768
Leu Phe Pro Pro Lys Pro Lys Asp Thr Leu Met Ile Ser Arg Thr Pro
                245                 250                 255 gag gtc aca tgc gtg gtg gtg gac gtg agc cac gaa gac cct gag gtc      816
Glu Val Thr Cys Val Val Val Asp Val Ser His Glu Asp Pro Glu Val
            260                 265                 270 aag ttc aac tgg tac gtg gac ggc gtg gag gtg cat aat gcc aag aca      864
Lys Phe Asn Trp Tyr Val Asp Gly Val Glu Val His Asn Ala Lys Thr
            275                 280                 285 aag ccg cgg gag gag cag tac aac agc acg tac cgt gtg gtc agc gtc      912
Lys Pro Arg Glu Glu Gln Tyr Asn Ser Thr Tyr Arg Val Val Ser Val
            290                 295                 300 ctc acc gtc ctg cac cag gac tgg ctg aat ggc aag gag tac aag tgc      960
Leu Thr Val Leu His Gln Asp Trp Leu Asn Gly Lys Glu Tyr Lys Cys
305                 310                 315                 320 aag gtc tcc aac aaa gcc ctc cca gcc ccc gaa gag aaa acc atc tcc     1008
Lys Val Ser Asn Lys Ala Leu Pro Ala Pro Glu Glu Lys Thr Ile Ser
                325                 330                 335 aaa gcc aaa ggg cag ccc cga gaa cca cag gtg tac acc ctg ccc cca     1056
Lys Ala Lys Gly Gln Pro Arg Glu Pro Gln Val Tyr Thr Leu Pro Pro
            340                 345                 350
```

```
tcc cgg gag gag atg acc aag aac cag gtc agc ctg acc tgc ctg gtc      1104
Ser Arg Glu Glu Met Thr Lys Asn Gln Val Ser Leu Thr Cys Leu Val
        355                 360                 365 aaa ggc ttc tat ccc agc gac atc gcc gtg gag tgg gag agc aat ggg      1152
Lys Gly Phe Tyr Pro Ser Asp Ile Ala Val Glu Trp Glu Ser Asn Gly
    370                 375                 380 cag ccg gag aac aac tac aag acc acg cct ccc gtg ctg gac tcc gac      1200
Gln Pro Glu Asn Asn Tyr Lys Thr Thr Pro Pro Val Leu Asp Ser Asp
385                 390                 395                 400 ggc tcc ttc ttc ctc tat agc aag ctc acc gtg gac aag agc agg tgg      1248
Gly Ser Phe Phe Leu Tyr Ser Lys Leu Thr Val Asp Lys Ser Arg Trp
            405                 410                 415 cag cag ggg aac gtc ttc tca tgc tcc gtg atg cat gag gct ctg cac      1296
Gln Gln Gly Asn Val Phe Ser Cys Ser Val Met His Glu Ala Leu His
        420                 425                 430 aac cac tac acg cag aag agc ctc tcc ctg tcc ccg ggt aaa              1338
Asn His Tyr Thr Gln Lys Ser Leu Ser Leu Ser Pro Gly Lys
    435                 440                 445

<210> SEQ ID NO 32
<211> LENGTH: 446
<212> TYPE: PRT
<213> ORGANISM: Artificial
<220> FEATURE:
<223> OTHER INFORMATION: Synthetic Construct

<400> SEQUENCE: 32

Ala Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Asn Gly Lys Ser Leu Glu Trp Ile
        35                  40                  45

Gly Asn Ile Asp Pro Tyr Tyr Gly Gly Thr Thr Tyr Asn Arg Lys Phe
    50                  55                  60

Lys Gly Lys Ala Thr Leu Thr Val Asp Lys Ser Ser Thr Ala Tyr
65                  70                  75                  80

Met Gln Leu Lys Ser Leu Thr Ser Glu Asp Ser Ala Val Tyr Tyr Cys
            85                  90                  95

Ala Arg Ser Val Gly Pro Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Ala Gly Pro Asp Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Glu Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 33
<211> LENGTH: 642
<212> TYPE: DNA
<213> ORGANISM: Artificial
<220> FEATURE:
<223> OTHER INFORMATION: Chimeric immunoglobulin sequence
<220> FEATURE:
<221> NAME/KEY: CDS
<222> LOCATION: (1)..(642)

<400> SEQUENCE: 33 gac atc cag atg act cag tct cca gcc tcc cta tct gca tct gtg gga      48
Asp Ile Gln Met Thr Gln Ser Pro Ala Ser Leu Ser Ala Ser Val Gly
1               5                   10                  15 gag act gtc acc atc aca tgt cga aca agt gaa aat gtt tac agt tat      96
Glu Thr Val Thr Ile Thr Cys Arg Thr Ser Glu Asn Val Tyr Ser Tyr
            20                  25                  30 ttg gct tgg tat cag cag aaa cag gga aaa tct cct cag ctc ctg gtc     144
Leu Ala Trp Tyr Gln Gln Lys Gln Gly Lys Ser Pro Gln Leu Leu Val
        35                  40                  45 tct ttt gca aaa acc tta gca gaa ggt gtg cca tca agg ttc agt ggc     192
Ser Phe Ala Lys Thr Leu Ala Glu Gly Val Pro Ser Arg Phe Ser Gly
    50                  55                  60 agt gga tca ggc aca cag ttt tct ctg aag atc agc agc ctg cag cct     240
Ser Gly Ser Gly Thr Gln Phe Ser Leu Lys Ile Ser Ser Leu Gln Pro
65                  70                  75                  80 gaa gat tct gga agt tat ttc tgt caa cat cat tcc gat aat ccg tgg     288
Glu Asp Ser Gly Ser Tyr Phe Cys Gln His His Ser Asp Asn Pro Trp
                85                  90                  95 acg ttc ggt gga ggc acc gaa ctg gag atc aaa cga act gtg gct gca     336
Thr Phe Gly Gly Gly Thr Glu Leu Glu Ile Lys Arg Thr Val Ala Ala
```

|  |  |  |  |  |  |  |  |  |  |  |  |  |  |  |  |
|---|---|---|---|---|---|---|---|---|---|---|---|---|---|---|---|
|  |  |  | 100 |  |  |  |  | 105 |  |  |  |  | 110 |  |  |
| cca | tct | gtc | ttc | atc | ttc | ccg | cca | tct | gat | gag | cag | ttg | aaa | tct | gga | 384 |
| Pro | Ser | Val | Phe | Ile | Phe | Pro | Pro | Ser | Asp | Glu | Gln | Leu | Lys | Ser | Gly |
|  |  | 115 |  |  |  |  | 120 |  |  |  |  | 125 |  |  |  |
| act | gcc | tct | gtt | gtg | tgc | ctg | ctg | aat | aac | ttc | tat | ccc | aga | gag | gcc | 432 |
| Thr | Ala | Ser | Val | Val | Cys | Leu | Leu | Asn | Asn | Phe | Tyr | Pro | Arg | Glu | Ala |
|  | 130 |  |  |  |  | 135 |  |  |  |  | 140 |  |  |  |  |
| aaa | gta | cag | tgg | aag | gtg | gat | aac | gcc | ctc | caa | tcg | ggt | aac | tcc | cag | 480 |
| Lys | Val | Gln | Trp | Lys | Val | Asp | Asn | Ala | Leu | Gln | Ser | Gly | Asn | Ser | Gln |
| 145 |  |  |  |  | 150 |  |  |  |  | 155 |  |  |  |  | 160 |
| gag | agt | gtc | aca | gag | cag | gac | agc | aag | gac | agc | acc | tac | agc | ctc | agc | 528 |
| Glu | Ser | Val | Thr | Glu | Gln | Asp | Ser | Lys | Asp | Ser | Thr | Tyr | Ser | Leu | Ser |
|  |  |  | 165 |  |  |  |  | 170 |  |  |  |  | 175 |  |  |
| agc | acc | ctg | acg | ctg | agc | aaa | gca | gac | tac | gag | aaa | cac | aaa | gtc | tac | 576 |
| Ser | Thr | Leu | Thr | Leu | Ser | Lys | Ala | Asp | Tyr | Glu | Lys | His | Lys | Val | Tyr |
|  |  | 180 |  |  |  |  | 185 |  |  |  |  | 190 |  |  |  |
| gcc | tgc | gaa | gtc | acc | cat | cag | ggc | ctg | agc | tcg | ccc | gtc | aca | aag | agc | 624 |
| Ala | Cys | Glu | Val | Thr | His | Gln | Gly | Leu | Ser | Ser | Pro | Val | Thr | Lys | Ser |
|  | 195 |  |  |  |  | 200 |  |  |  |  | 205 |  |  |  |  |
| ttc | aac | agg | gga | gag | tgt |  |  |  |  |  |  |  |  |  |  | 642 |
| Phe | Asn | Arg | Gly | Glu | Cys |
|  | 210 |

<210> SEQ ID NO 34
<211> LENGTH: 214
<212> TYPE: PRT
<213> ORGANISM: Artificial
<220> FEATURE:
<223> OTHER INFORMATION: Synthetic Construct

<400> SEQUENCE: 34

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Val Tyr Ser Tyr
            20                  25                  30

Leu Ala Trp Tyr Gln Gln Lys Gln Gly Lys Ser Pro Gln Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Gln Phe Ser Leu Lys Ile Ser Ser Leu Gln Pro
65                  70                  75                  80

Glu Asp Ser Gly Ser Tyr Phe Cys Gln His His Ser Asp Asn Pro Trp
                85                  90                  95

Thr Phe Gly Gly Gly Thr Glu Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

```
Phe Asn Arg Gly Glu Cys
    210

<210> SEQ ID NO 35
<211> LENGTH: 1338
<212> TYPE: DNA
<213> ORGANISM: Artificial
<220> FEATURE:
<223> OTHER INFORMATION: Fc-engineered humanized immunoglobulin sequence
<220> FEATURE:
<221> NAME/KEY: CDS
<222> LOCATION: (1)..(1338)

<400> SEQUENCE: 35 gcg gtc cag ctg gtg cag agc gga gcc gag gtg aag aag ccc ggc agc      48
Ala Val Gln Leu Val Gln Ser Gly Ala Glu Val Lys Lys Pro Gly Ser
1               5                   10                  15 agc gtc aag gtg tcc tgc aag gcc agc ggc tac agc ttc acc ggc tac      96
Ser Val Lys Val Ser Cys Lys Ala Ser Gly Tyr Ser Phe Thr Gly Tyr
            20                  25                  30 aac atg aac tgg gtg cgg cag gcc cca ggc cag gga ctg gaa tgg atg     144
Asn Met Asn Trp Val Arg Gln Ala Pro Gly Gln Gly Leu Glu Trp Met
        35                  40                  45 ggc aac atc gac ccc tac tac ggc ggc acc acc tac aac cgg aag ttc     192
Gly Asn Ile Asp Pro Tyr Tyr Gly Gly Thr Thr Tyr Asn Arg Lys Phe
    50                  55                  60 aag ggc cgg gtg acc ctg acc gtg gac aag agc agc agc acc gcc tac     240
Lys Gly Arg Val Thr Leu Thr Val Asp Lys Ser Ser Ser Thr Ala Tyr
65                  70                  75                  80 atg gaa ctg agc agc ctg cgg agc gag gac acc gcc gtg tac tac tgc     288
Met Glu Leu Ser Ser Leu Arg Ser Glu Asp Thr Ala Val Tyr Tyr Cys
                85                  90                  95 gcc aga tcc gtg ggc ccc atg gac tac tgg ggc cag ggc acc ctg gtc     336
Ala Arg Ser Val Gly Pro Met Asp Tyr Trp Gly Gln Gly Thr Leu Val
            100                 105                 110 acc gtc tct tca gcc tcc acc aag ggc cca tcg gtc ttc ccc ctg gca     384
Thr Val Ser Ser Ala Ser Thr Lys Gly Pro Ser Val Phe Pro Leu Ala
        115                 120                 125 ccc tcc tcc aag agc acc tct ggg ggc aca gcg gcc ctg ggc tgc ctg     432
Pro Ser Ser Lys Ser Thr Ser Gly Gly Thr Ala Ala Leu Gly Cys Leu
    130                 135                 140 gtc aag gac tac ttc ccc gaa ccg gtg acg gtg tcg tgg aac tca ggc     480
Val Lys Asp Tyr Phe Pro Glu Pro Val Thr Val Ser Trp Asn Ser Gly
145                 150                 155                 160 gcc ctg acc agc ggc gtg cac acc ttc ccg gct gtc cta cag tcc tca     528
Ala Leu Thr Ser Gly Val His Thr Phe Pro Ala Val Leu Gln Ser Ser
                165                 170                 175 gga ctc tac tcc ctc agc agc gtg gtg acc gtg ccc tcc agc agc ttg     576
Gly Leu Tyr Ser Leu Ser Ser Val Val Thr Val Pro Ser Ser Ser Leu
            180                 185                 190 ggc acc cag acc tac atc tgc aac gtg aat cac aag ccc agc aac acc     624
Gly Thr Gln Thr Tyr Ile Cys Asn Val Asn His Lys Pro Ser Asn Thr
        195                 200                 205 aag gtg gac aag aga gtt gag ccc aaa tct tgt gac aaa act cac aca     672
Lys Val Asp Lys Arg Val Glu Pro Lys Ser Cys Asp Lys Thr His Thr
    210                 215                 220 tgc cca ccg tgc cca gca cct gaa ctc ctg ggg gga ccg gac gtc ttc     720
Cys Pro Pro Cys Pro Ala Pro Glu Leu Leu Gly Gly Pro Asp Val Phe
225                 230                 235                 240 ctc ttc ccc cca aaa ccc aag gac acc ctc atg atc tcc cgg acc cct     768
Leu Phe Pro Pro Lys Pro Lys Asp Thr Leu Met Ile Ser Arg Thr Pro
                245                 250                 255
```

```
gag gtc aca tgc gtg gtg gtg gac gtg agc cac gaa gac cct gag gtc      816
Glu Val Thr Cys Val Val Val Asp Val Ser His Glu Asp Pro Glu Val
        260                 265                 270 aag ttc aac tgg tac gtg gac ggc gtg gag gtg cat aat gcc aag aca      864
Lys Phe Asn Trp Tyr Val Asp Gly Val Glu Val His Asn Ala Lys Thr
    275                 280                 285 aag ccg cgg gag gag cag tac aac agc acg tac cgt gtg gtc agc gtc      912
Lys Pro Arg Glu Glu Gln Tyr Asn Ser Thr Tyr Arg Val Val Ser Val
290                 295                 300 ctc acc gtc ctg cac cag gac tgg ctg aat ggc aag gag tac aag tgc      960
Leu Thr Val Leu His Gln Asp Trp Leu Asn Gly Lys Glu Tyr Lys Cys
305                 310                 315                 320 aag gtc tcc aac aaa gcc ctc cca gcc ccc gaa gag aaa acc atc tcc     1008
Lys Val Ser Asn Lys Ala Leu Pro Ala Pro Glu Glu Lys Thr Ile Ser
            325                 330                 335 aaa gcc aaa ggg cag ccc cga gaa cca cag gtg tac acc ctg ccc cca     1056
Lys Ala Lys Gly Gln Pro Arg Glu Pro Gln Val Tyr Thr Leu Pro Pro
        340                 345                 350 tcc cgg gag gag atg acc aag aac cag gtc agc ctg acc tgc ctg gtc     1104
Ser Arg Glu Glu Met Thr Lys Asn Gln Val Ser Leu Thr Cys Leu Val
    355                 360                 365 aaa ggc ttc tat ccc agc gac atc gcc gtg gag tgg gag agc aat ggg     1152
Lys Gly Phe Tyr Pro Ser Asp Ile Ala Val Glu Trp Glu Ser Asn Gly
370                 375                 380 cag ccg gag aac aac tac aag acc acg cct ccc gtg ctg gac tcc gac     1200
Gln Pro Glu Asn Asn Tyr Lys Thr Thr Pro Pro Val Leu Asp Ser Asp
385                 390                 395                 400 ggc tcc ttc ttc ctc tat agc aag ctc acc gtg gac aag agc agg tgg     1248
Gly Ser Phe Phe Leu Tyr Ser Lys Leu Thr Val Asp Lys Ser Arg Trp
            405                 410                 415 cag cag ggg aac gtc ttc tca tgc tcc gtg atg cat gag gct ctg cac     1296
Gln Gln Gly Asn Val Phe Ser Cys Ser Val Met His Glu Ala Leu His
        420                 425                 430 aac cac tac acg cag aag agc ctc tcc ctg tcc ccg ggt aaa             1338
Asn His Tyr Thr Gln Lys Ser Leu Ser Leu Ser Pro Gly Lys
    435                 440                 445

<210> SEQ ID NO 36
<211> LENGTH: 446
<212> TYPE: PRT
<213> ORGANISM: Artificial
<220> FEATURE:
<223> OTHER INFORMATION: Synthetic Construct

<400> SEQUENCE: 36

Ala Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Thr Gly Tyr
            20                  25                  30

Asn Met Asn Trp Val Arg Gln Ala Pro Gly Gln Gly Leu Glu Trp Met
        35                  40                  45

Gly Asn Ile Asp Pro Tyr Tyr Gly Thr Thr Tyr Asn Arg Lys Phe
    50                  55                  60

Lys Gly Arg Val Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Val Gly Pro Met Asp Tyr Trp Gly Gln Gly Thr Leu Val
            100                 105                 110
```

```
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
        130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
210                 215                 220
Cys Pro Pro Cys Pro Ala Pro Glu Leu Leu Gly Gly Pro Asp Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Glu Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 37
<211> LENGTH: 642
<212> TYPE: DNA
<213> ORGANISM: Artificial
<220> FEATURE:
<223> OTHER INFORMATION: Humanized immunoglobulin sequence
<220> FEATURE:
<221> NAME/KEY: CDS
<222> LOCATION: (1)..(642)

<400> SEQUENCE: 37 gac atc cag atg acc cag agc ccc agc agc ctg agc gcc agc gtg ggc        48
Asp Ile Gln Met Thr Gln Ser Pro Ser Ser Leu Ser Ala Ser Val Gly
```

```
                1               5                      10                      15
       gac cgg gtg acc atc acc tgc cgg acc agc gag aac gtg tac agc tac              96
       Asp Arg Val Thr Ile Thr Cys Arg Thr Ser Glu Asn Val Tyr Ser Tyr
                       20                      25                      30 ctg gcc tgg tat cag cag aag ccc ggc aag gcc ccc aag ctg ctg gtg             144
       Leu Ala Trp Tyr Gln Gln Lys Pro Gly Lys Ala Pro Lys Leu Leu Val
                       35                      40                      45 tcc ttc gcc aag acc ctg gcc gag ggc gtg ccc agc cgg ttt agc ggc             192
       Ser Phe Ala Lys Thr Leu Ala Glu Gly Val Pro Ser Arg Phe Ser Gly
                50                      55                      60 agc ggc tcc ggc acc gac ttc acc ctg acc atc agc agc ctg cag ccc             240
       Ser Gly Ser Gly Thr Asp Phe Thr Leu Thr Ile Ser Ser Leu Gln Pro
        65                      70                      75                      80 gag gac ttc gcc acc tac ttt tgc cag cac cac agc gac aac ccc tgg             288
       Glu Asp Phe Ala Thr Tyr Phe Cys Gln His His Ser Asp Asn Pro Trp
                       85                      90                      95 acc ttc ggc cag ggc acc aag gtg gag atc aaa cga act gtg gct gca             336
       Thr Phe Gly Gln Gly Thr Lys Val Glu Ile Lys Arg Thr Val Ala Ala
                       100                     105                     110 cca tct gtc ttc atc ttc ccg cca tct gat gag cag ttg aaa tct gga             384
       Pro Ser Val Phe Ile Phe Pro Pro Ser Asp Glu Gln Leu Lys Ser Gly
                       115                     120                     125 act gcc tct gtt gtg tgc ctg ctg aat aac ttc tat ccc aga gag gcc             432
       Thr Ala Ser Val Val Cys Leu Leu Asn Asn Phe Tyr Pro Arg Glu Ala
               130                     135                     140 aaa gta cag tgg aag gtg gat aac gcc ctc caa tcg ggt aac tcc cag             480
       Lys Val Gln Trp Lys Val Asp Asn Ala Leu Gln Ser Gly Asn Ser Gln
       145                     150                     155                     160 gag agt gtc aca gag cag gac agc aag gac agc acc tac agc ctc agc             528
       Glu Ser Val Thr Glu Gln Asp Ser Lys Asp Ser Thr Tyr Ser Leu Ser
                       165                     170                     175 agc acc ctg acg ctg agc aaa gca gac tac gag aaa cac aaa gtc tac             576
       Ser Thr Leu Thr Leu Ser Lys Ala Asp Tyr Glu Lys His Lys Val Tyr
                       180                     185                     190 gcc tgc gaa gtc acc cat cag ggc ctg agc tcg ccc gtc aca aag agc             624
       Ala Cys Glu Val Thr His Gln Gly Leu Ser Ser Pro Val Thr Lys Ser
                       195                     200                     205 ttc aac agg gga gag tgt                                                     642
       Phe Asn Arg Gly Glu Cys
           210

<210> SEQ ID NO 38
<211> LENGTH: 214
<212> TYPE: PRT
<213> ORGANISM: Artificial
<220> FEATURE:
<223> OTHER INFORMATION: Synthetic Construct

<400> SEQUENCE: 38

Asp Ile Gln Met Thr Gln Ser Pro Ser Ser Leu Ser Ala Ser Val Gly
 1               5                      10                      15

Asp Arg Val Thr Ile Thr Cys Arg Thr Ser Glu Asn Val Tyr Ser Tyr
                20                      25                      30

Leu Ala Trp Tyr Gln Gln Lys Pro Gly Lys Ala Pro Lys Leu Leu Val
            35                      40                      45

Ser Phe Ala Lys Thr Leu Ala Glu Gly Val Pro Ser Arg Phe Ser Gly
        50                      55                      60

Ser Gly Ser Gly Thr Asp Phe Thr Leu Thr Ile Ser Ser Leu Gln Pro
 65                     70                      75                      80
```

```
Glu Asp Phe Ala Thr Tyr Phe Cys Gln His His Ser Asp Asn Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 39
<211> LENGTH: 1338
<212> TYPE: DNA
<213> ORGANISM: Artificial
<220> FEATURE:
<223> OTHER INFORMATION: Fc-engineered humanized immunoglobulin sequence
<220> FEATURE:
<221> NAME/KEY: CDS
<222> LOCATION: (1)..(1338)

<400> SEQUENCE: 39 gcg gtc cag ctg gtg cag agc gga gcc gag gtg aag aag ccc ggc agc        48
Ala Val Gln Leu Val Gln Ser Gly Ala Glu Val Lys Lys Pro Gly Ser
1               5                   10                  15 agc gtc aag gtg tcc tgc aag gcc agc ggc tac agc ttc acc ggc tac        96
Ser Val Lys Val Ser Cys Lys Ala Ser Gly Tyr Ser Phe Thr Gly Tyr
            20                  25                  30 aac atg aac tgg gtg cgg cag gcc cca ggc cag gga ctg gaa tgg atg       144
Asn Met Asn Trp Val Arg Gln Ala Pro Gly Gln Gly Leu Glu Trp Met
        35                  40                  45 ggc aac atc gac ccc tac tac ggc ggc acc acc tac aac cgg aag ttc       192
Gly Asn Ile Asp Pro Tyr Tyr Gly Gly Thr Thr Tyr Asn Arg Lys Phe
    50                  55                  60 aag ggc cgg gtg acc ctg acc gtg gac aag agc agc agc acc gcc tac       240
Lys Gly Arg Val Thr Leu Thr Val Asp Lys Ser Ser Ser Thr Ala Tyr
65                  70                  75                  80 atg gaa ctg agc agc ctg cgg agc gag gac acc gcc gtg tac tac tgc       288
Met Glu Leu Ser Ser Leu Arg Ser Glu Asp Thr Ala Val Tyr Tyr Cys
                85                  90                  95 gcc aga tcc gtg ggc ccc atg gac tac tgg ggc cag ggc acc ctg gtc       336
Ala Arg Ser Val Gly Pro Met Asp Tyr Trp Gly Gln Gly Thr Leu Val
            100                 105                 110 acc gtc tct tca gcc tcc acc aag ggc cca tcg gtc ttc ccc ctg gca       384
Thr Val Ser Ser Ala Ser Thr Lys Gly Pro Ser Val Phe Pro Leu Ala
        115                 120                 125 ccc tcc tcc aag agc acc tct ggg ggc aca gcg gcc ctg ggc tgc ctg       432
Pro Ser Ser Lys Ser Thr Ser Gly Gly Thr Ala Ala Leu Gly Cys Leu
    130                 135                 140 gtc aag gac tac ttc ccc gaa ccg gtg acg gtg tcg tgg aac tca ggc       480
Val Lys Asp Tyr Phe Pro Glu Pro Val Thr Val Ser Trp Asn Ser Gly
145                 150                 155                 160
```

```
gcc ctg acc agc ggc gtg cac acc ttc ccg gct gtc cta cag tcc tca      528
Ala Leu Thr Ser Gly Val His Thr Phe Pro Ala Val Leu Gln Ser Ser
            165                 170                 175 gga ctc tac tcc ctc agc agc gtg gtg acc gtg ccc tcc agc agc ttg      576
Gly Leu Tyr Ser Leu Ser Ser Val Val Thr Val Pro Ser Ser Ser Leu
        180                 185                 190 ggc acc cag acc tac atc tgc aac gtg aat cac aag ccc agc aac acc      624
Gly Thr Gln Thr Tyr Ile Cys Asn Val Asn His Lys Pro Ser Asn Thr
    195                 200                 205 aag gtg gac aag aga gtt gag ccc aaa tct tgt gac aaa act cac aca      672
Lys Val Asp Lys Arg Val Glu Pro Lys Ser Cys Asp Lys Thr His Thr
210                 215                 220 tgc cca ccg tgc cca gca cct gaa ctc ctg gcg gga ccg gat gtc ttc      720
Cys Pro Pro Cys Pro Ala Pro Glu Leu Leu Ala Gly Pro Asp Val Phe
225                 230                 235                 240 ctc ttc ccc cca aaa ccc aag gac acc ctc atg atc tcc cgg acc cct      768
Leu Phe Pro Pro Lys Pro Lys Asp Thr Leu Met Ile Ser Arg Thr Pro
                245                 250                 255 gag gtc aca tgc gtg gtg gtg gac gtg agc cac gaa gac cct gag gtc      816
Glu Val Thr Cys Val Val Val Asp Val Ser His Glu Asp Pro Glu Val
            260                 265                 270 aag ttc aac tgg tac gtg gac ggc gtg gag gtg cat aat gcc aag aca      864
Lys Phe Asn Trp Tyr Val Asp Gly Val Glu Val His Asn Ala Lys Thr
        275                 280                 285 aag ccg cgg gag gag cag tac aac agc acg tac cgt gtg gtc agc gtc      912
Lys Pro Arg Glu Glu Gln Tyr Asn Ser Thr Tyr Arg Val Val Ser Val
    290                 295                 300 ctc acc gtc ctg cac cag gac tgg ctg aat ggc aag gag tac aag tgc      960
Leu Thr Val Leu His Gln Asp Trp Leu Asn Gly Lys Glu Tyr Lys Cys
305                 310                 315                 320 aag gtc tcc aac aaa gcc ctc cca gcc ccc gaa gag aaa acc atc tcc     1008
Lys Val Ser Asn Lys Ala Leu Pro Ala Pro Glu Glu Lys Thr Ile Ser
                325                 330                 335 aaa gcc aaa ggg cag ccc cga gaa cca cag gtg tac acc ctg ccc cca     1056
Lys Ala Lys Gly Gln Pro Arg Glu Pro Gln Val Tyr Thr Leu Pro Pro
            340                 345                 350 tcc cgg gag gag atg acc aag aac cag gtc agc ctg acc tgc ctg gtc     1104
Ser Arg Glu Glu Met Thr Lys Asn Gln Val Ser Leu Thr Cys Leu Val
        355                 360                 365 aaa ggc ttc tat ccc agc gac atc gcc gtg gag tgg gag agc aat ggg     1152
Lys Gly Phe Tyr Pro Ser Asp Ile Ala Val Glu Trp Glu Ser Asn Gly
    370                 375                 380 cag ccg gag aac aac tac aag acc acg cct ccc gtg ctg gac tcc gac     1200
Gln Pro Glu Asn Asn Tyr Lys Thr Thr Pro Pro Val Leu Asp Ser Asp
385                 390                 395                 400 ggc tcc ttc ttc ctc tat agc aag ctc acc gtg gac aag agc agg tgg     1248
Gly Ser Phe Phe Leu Tyr Ser Lys Leu Thr Val Asp Lys Ser Arg Trp
                405                 410                 415 cag cag ggg aac gtc ttc tca tgc tcc gtg atg cat gag gct ctg cac     1296
Gln Gln Gly Asn Val Phe Ser Cys Ser Val Met His Glu Ala Leu His
            420                 425                 430 aac cac tac acg cag aag agc ctc tcc ctg tcc ccg ggt aaa             1338
Asn His Tyr Thr Gln Lys Ser Leu Ser Leu Ser Pro Gly Lys
        435                 440                 445

<210> SEQ ID NO 40
<211> LENGTH: 446
<212> TYPE: PRT
<213> ORGANISM: Artificial
<220> FEATURE:
```

<223> OTHER INFORMATION: Synthetic Construct

<400> SEQUENCE: 40

```
Ala Val Gln Leu Val Gln Ser Gly Ala Glu Val Lys Lys Pro Gly Ser
1               5                   10                  15
Ser Val Lys Val Ser Cys Lys Ala Ser Gly Tyr Ser Phe Thr Gly Tyr
            20                  25                  30
Asn Met Asn Trp Val Arg Gln Ala Pro Gly Gln Gly Leu Glu Trp Met
        35                  40                  45
Gly Asn Ile Asp Pro Tyr Tyr Gly Gly Thr Thr Tyr Asn Arg Lys Phe
    50                  55                  60
Lys Gly Arg Val Thr Leu Thr Val Asp Lys Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Val Gly Pro Met Asp Tyr Trp Gly Gln Gly Thr Leu Val
            100                 105                 110
Thr Val Ser Ser Ala Ser Thr Lys Gly Pro Ser Val Phe Pro Leu Ala
        115                 120                 125
Pro Ser Ser Lys Ser Thr Ser Gly Gly Thr Ala Ala Leu Gly Cys Leu
    130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
            180                 185                 190
Gly Thr Gln Thr Tyr Ile Cys Asn Val Asn His Lys Pro Ser Asn Thr
        195                 200                 205
Lys Val Asp Lys Arg Val Glu Pro Lys Ser Cys Asp Lys Thr His Thr
    210                 215                 220
Cys Pro Pro Cys Pro Ala Pro Glu Leu Leu Ala Gly Pro Asp Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Glu Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Glu Glu Met Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
```

```
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 41
<211> LENGTH: 642
<212> TYPE: DNA
<213> ORGANISM: Artificial
<220> FEATURE:
<223> OTHER INFORMATION: Humanized immunoglobulin sequence
<220> FEATURE:
<221> NAME/KEY: CDS
<222> LOCATION: (1)..(642)

<400> SEQUENCE: 41 gac atc cag atg acc cag agc ccc agc agc ctg agc gcc agc gtg ggc      48
Asp Ile Gln Met Thr Gln Ser Pro Ser Ser Leu Ser Ala Ser Val Gly
1               5                   10                  15 gac cgg gtg acc atc acc tgc cgg acc agc gag aac gtg tac agc tac      96
Asp Arg Val Thr Ile Thr Cys Arg Thr Ser Glu Asn Val Tyr Ser Tyr
            20                  25                  30 ctg gcc tgg tat cag cag aag ccc ggc aag gcc ccc aag ctg ctg gtg     144
Leu Ala Trp Tyr Gln Gln Lys Pro Gly Lys Ala Pro Lys Leu Leu Val
        35                  40                  45 tcc ttc gcc aag acc ctg gcc gag ggc gtg ccc agc cgg ttt agc ggc     192
Ser Phe Ala Lys Thr Leu Ala Glu Gly Val Pro Ser Arg Phe Ser Gly
    50                  55                  60 agc ggc tcc ggc acc gac ttc acc ctg acc atc agc agc ctg cag ccc     240
Ser Gly Ser Gly Thr Asp Phe Thr Leu Thr Ile Ser Ser Leu Gln Pro
65                  70                  75                  80 gag gac ttc gcc acc tac ttt tgc cag cac cac agc gac aac ccc tgg     288
Glu Asp Phe Ala Thr Tyr Phe Cys Gln His His Ser Asp Asn Pro Trp
                85                  90                  95 acc ttc ggc cag ggc acc aag gtg gag atc aaa cga act gtg gct gca     336
Thr Phe Gly Gln Gly Thr Lys Val Glu Ile Lys Arg Thr Val Ala Ala
            100                 105                 110 cca tct gtc ttc atc ttc ccg cca tct gat gag cag ttg aaa tct gga     384
Pro Ser Val Phe Ile Phe Pro Pro Ser Asp Glu Gln Leu Lys Ser Gly
        115                 120                 125 act gcc tct gtt gtg tgc ctg ctg aat aac ttc tat ccc aga gag gcc     432
Thr Ala Ser Val Val Cys Leu Leu Asn Asn Phe Tyr Pro Arg Glu Ala
    130                 135                 140 aaa gta cag tgg aag gtg gat aac gcc ctc caa tcg ggt aac tcc cag     480
Lys Val Gln Trp Lys Val Asp Asn Ala Leu Gln Ser Gly Asn Ser Gln
145                 150                 155                 160 gag agt gtc aca gag cag gac agc aag gac agc acc tac agc ctc agc     528
Glu Ser Val Thr Glu Gln Asp Ser Lys Asp Ser Thr Tyr Ser Leu Ser
                165                 170                 175 agc acc ctg acg ctg agc aaa gca gac tac gag aaa cac aaa gtc tac     576
Ser Thr Leu Thr Leu Ser Lys Ala Asp Tyr Glu Lys His Lys Val Tyr
            180                 185                 190 gcc tgc gaa gtc acc cat cag ggc ctg agc tcg ccc gtc aca aag agc     624
Ala Cys Glu Val Thr His Gln Gly Leu Ser Ser Pro Val Thr Lys Ser
        195                 200                 205 ttc aac agg gga gag tgt                                              642
Phe Asn Arg Gly Glu Cys
    210
```

```
<210> SEQ ID NO 42
<211> LENGTH: 214
<212> TYPE: PRT
<213> ORGANISM: Artificial
<220> FEATURE:
<223> OTHER INFORMATION: Synthetic Construct

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Val Tyr Ser Tyr
            20                  25                  30

Leu Ala Trp Tyr Gln Gln Lys Pro Gly Lys Ala Pro Lys Leu Leu Val
        35                  40                  45

Ser Phe Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His His Ser Asp Asn Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```